United States Patent
Gloss et al.

(10) Patent No.: US 10,568,739 B2
(45) Date of Patent: *Feb. 25, 2020

(54) VALVE DELIVERY TOOL

(71) Applicant: Medtronic, Inc., Minneapolis, MN (US)

(72) Inventors: Michael Gloss, Minneapolis, MN (US); Timothy Groen, Rush City, MN (US); Carolyn Majkrzak, Chanhassen, MN (US); Behrooz Nadian, Maple Grove, MN (US); Matthew Rust, Windsor, CA (US); Timothy Ryan, Shorewood, MN (US); Matthew Weston, Roseville, MN (US); Marc Anderson, Ballybrit (IE); Evelyn Birmingham, Ballybrit (IE); Mark Casley, Ballybrit (IE); Deirdre McGowan Smyth, Ballybrit (IE)

(73) Assignee: Medtronic, Inc., Minneapolis, MN (US)

( * ) Notice: Subject to any disclaimer, the term of this patent is extended or adjusted under 35 U.S.C. 154(b) by 170 days.

This patent is subject to a terminal disclaimer.

(21) Appl. No.: 15/457,454

(22) Filed: Mar. 13, 2017

(65) Prior Publication Data

US 2017/0231755 A1  Aug. 17, 2017

Related U.S. Application Data

(63) Continuation of application No. 14/268,375, filed on May 2, 2014, now Pat. No. 9,629,718.
(Continued)

(51) Int. Cl.
*A61F 2/24* (2006.01)
*A61F 2/95* (2013.01)

(52) U.S. Cl.
CPC ............... *A61F 2/243* (2013.01); *A61F 2/24* (2013.01); *A61F 2/2418* (2013.01);
(Continued)

(58) Field of Classification Search
CPC .............. A61F 2/2427; A61F 2/2496; A61F 2250/0007; A61F 2/2412; A61F 2/2418;
(Continued)

(56) References Cited

U.S. PATENT DOCUMENTS 3,334,629 A  8/1967 Cohn
3,409,013 A  11/1968 Berry
(Continued)

FOREIGN PATENT DOCUMENTS

CN  2007-100074433  1/2007
DE  3640745  6/1987
(Continued)

OTHER PUBLICATIONS

PCT/US2014/036688, PCT International Search Report and Written Opinion, dated Aug. 18, 2014.
(Continued)

*Primary Examiner* — Katrina M Stransky

(57) ABSTRACT

A system includes a medical device for implanting in a valve of a subject, the implantable medical device having a self-expanding frame; and a holder configured to retain the frame of the implantable medical device in a constricted configuration and to control expansion of the frame. The holder has a controllably constrictable and expandable loop, wherein the loop is disposed about at least a portion of the self-expanding frame such that constriction or expansion of the first loop controls constriction or expansion of the frame.

20 Claims, 45 Drawing Sheets

Related U.S. Application Data

(60) Provisional application No. 61/819,488, filed on May 3, 2013, provisional application No. 61/819,492, filed on May 3, 2013, provisional application No. 61/819,490, filed on May 3, 2013, provisional application No. 61/930,905, filed on Jan. 23, 2014.

(52) U.S. Cl.
CPC .......... *A61F 2/2427* (2013.01); *A61F 2/2439* (2013.01); *A61F 2/2496* (2013.01); *A61F 2/2412* (2013.01); *A61F 2/2436* (2013.01); *A61F 2002/9517* (2013.01); *A61F 2002/9522* (2013.01); *A61F 2220/0033* (2013.01); *A61F 2250/0007* (2013.01)

(58) Field of Classification Search
CPC ...... A61F 2002/9517; A61F 2002/9522; A61F 2220/0033; A61F 2/24; A61F 2/2466; A61F 2/18
See application file for complete search history.

(56) References Cited

U.S. PATENT DOCUMENTS

| | | |
|---|---|---|
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,451,936 A | 6/1984 | Carpentier et al. |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,679,556 A | 7/1987 | Lubock et al. |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 7/1993 | Tower |
| 5,232,445 A | 8/1993 | Bonzel |
| 5,236,450 A | 8/1993 | Scott |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Anderson |
| 5,415,633 A | 5/1995 | Lazarus et al. |
| 5,431,676 A | 7/1995 | Dubrul et al. |
| 5,443,446 A | 8/1995 | Shturman |
| 5,443,502 A | 8/1995 | Caudillo et al. |
| 5,449,384 A | 9/1995 | Johnson |
| 5,476,510 A | 12/1995 | Eberhardt et al. |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,578,076 A | 11/1996 | Krueger et al. |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,833,694 A | 11/1998 | Poncet |

(56) References Cited

U.S. PATENT DOCUMENTS

| | | |
|---|---|---|
| 5,840,081 A | 11/1998 | Anderson |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler |
| 5,860,996 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,017,362 A | 1/2000 | Lau |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A * | 3/2000 | Williamson, IV .......................... A61B 17/0469 606/151 |
| 6,051,104 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Anderson |
| 6,171,335 B1 | 1/2001 | Wheatley et al. |
| 6,197,053 B1 | 3/2001 | Cosgrove et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,416,547 B1 | 7/2002 | Erickson et al. |
| 6,425,916 B1 | 7/2002 | Garrison |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhaigh |
| 6,503,272 B2 | 1/2003 | Duerig |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,558,417 B2 | 5/2003 | Peredo |
| 6,558,418 B2 | 5/2003 | Carpentier |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Anderson |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser |
| 6,730,377 B2 | 5/2004 | Wang |
| 6,733,525 B2 | 5/2004 | Yang |
| 6,736,845 B2 | 5/2004 | Marquez et al. |
| 6,736,846 B2 | 5/2004 | Cox |
| 6,752,828 B2 | 6/2004 | Thornton |
| 6,758,855 B2 | 7/2004 | Fulton, III et al. |
| 6,767,362 B2 | 7/2004 | Schreck |
| 6,769,434 B2 | 8/2004 | Liddicoat et al. |
| 6,786,925 B1 | 9/2004 | Schoon |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |

(56) References Cited

U.S. PATENT DOCUMENTS

| | | |
|---|---|---|
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,682,390 B2 | 3/2010 | Seguin |
| 7,780,726 B2 | 8/2010 | Seguin |
| 7,806,919 B2 | 10/2010 | Bloom et al. |
| 9,629,718 B2 * | 4/2017 | Gloss ................. A61F 2/24 |
| 2001/0002445 A1 | 3/2001 | Vesely |
| 2001/0001314 A1 | 5/2001 | Davison et al. |
| 2001/0007956 A1 | 7/2001 | Letac |
| 2001/0010017 A1 | 7/2001 | Letac et al. |
| 2001/0011017 A1 | 7/2001 | Letac |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0013621 A1 | 1/2002 | Stobie et al. |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0133226 A1 | 9/2002 | Marquez et al. |
| 2002/0138138 A1 | 9/2002 | Yang |
| 2002/0105197 A1 | 10/2002 | Garrison |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0060875 A1 | 3/2003 | Wittens |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0059412 A1 | 3/2004 | Lytle et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |

(56) References Cited

U.S. PATENT DOCUMENTS

| | | |
|---|---|---|
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0182486 A1 | 8/2005 | Gabbay |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203615 A1 | 9/2005 | Forster et al. |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240262 A1 | 10/2005 | White |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0161249 A1 | 7/2006 | Realyvasquez et al. |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271081 A1 | 11/2006 | Realyvasquez |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100427 A1* | 5/2007 | Perouse ............... A61F 2/07 623/1.11 |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0112422 A1 | 5/2007 | Dehdashtian |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233223 A1 | 10/2007 | Styrc |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255093 A1 | 11/2007 | Lau et al. |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |

(56) References Cited

U.S. PATENT DOCUMENTS

| | | | |
|---|---|---|---|
| 2008/0154355 A1 | 6/2008 | Benichow et al. | |
| 2008/0154356 A1 | 6/2008 | Obermiller et al. | |
| 2008/0161910 A1 | 7/2008 | Revuelta et al. | |
| 2008/0161911 A1 | 7/2008 | Revuelta et al. | |
| 2008/0183273 A1 | 7/2008 | Mesana et al. | |
| 2008/0188928 A1 | 8/2008 | Salahieh et al. | |
| 2008/0215143 A1 | 9/2008 | Seguin et al. | |
| 2008/0215144 A1 | 9/2008 | Ryan et al. | |
| 2008/0228254 A1 | 9/2008 | Ryan | |
| 2008/0228263 A1 | 9/2008 | Ryan | |
| 2008/0234797 A1 | 9/2008 | Stryc | |
| 2008/0243246 A1 | 10/2008 | Ryan et al. | |
| 2008/0255651 A1 | 10/2008 | Dwork | |
| 2008/0255660 A1 | 10/2008 | Guyenot et al. | |
| 2008/0255661 A1 | 10/2008 | Straubinger et al. | |
| 2008/0262593 A1 | 10/2008 | Ryan et al. | |
| 2008/0269878 A1 | 10/2008 | Iobbi | |
| 2009/0005863 A1 | 1/2009 | Goetz et al. | |
| 2009/0012600 A1 | 1/2009 | Styrc et al. | |
| 2009/0048656 A1 | 2/2009 | Wen | |
| 2009/0054976 A1 | 2/2009 | Tuval et al. | |
| 2009/0069886 A1 | 3/2009 | Suri et al. | |
| 2009/0069887 A1 | 3/2009 | Righini et al. | |
| 2009/0069889 A1 | 3/2009 | Suri et al. | |
| 2009/0082858 A1 | 3/2009 | Nugent et al. | |
| 2009/0085900 A1 | 4/2009 | Weiner | |
| 2009/0099653 A1 | 4/2009 | Suri et al. | |
| 2009/0138079 A1 | 5/2009 | Tuval et al. | |
| 2009/0164004 A1 | 6/2009 | Cohn | |
| 2009/0164006 A1 | 6/2009 | Seguin et al. | |
| 2009/0171447 A1 | 7/2009 | VonSeggesser et al. | |
| 2009/0192585 A1 | 7/2009 | Bloom et al. | |
| 2009/0192586 A1 | 7/2009 | Tabor et al. | |
| 2009/0192591 A1 | 7/2009 | Ryan et al. | |
| 2009/0198316 A1 | 8/2009 | Laske et al. | |
| 2009/0216310 A1 | 8/2009 | Straubinger et al. | |
| 2009/0216312 A1 | 8/2009 | Straubinger et al. | |
| 2009/0216313 A1 | 8/2009 | Straubinger et al. | |
| 2009/0222082 A1 | 9/2009 | Lock et al. | |
| 2009/0234443 A1 | 9/2009 | Ottma et al. | |
| 2009/0240264 A1 | 9/2009 | Tuval et al. | |
| 2009/0240320 A1 | 9/2009 | Tuval | |
| 2009/0287296 A1 | 11/2009 | Manasse | |
| 2010/0004740 A1 | 1/2010 | Seguin et al. | |
| 2010/0030328 A1 | 2/2010 | Seguin et al. | |
| 2010/0036479 A1 | 2/2010 | Hill et al. | |
| 2010/0036485 A1 | 2/2010 | Seguin | |
| 2010/0069852 A1 | 3/2010 | Kelley | |
| 2010/0094411 A1 | 4/2010 | Tuval et al. | |
| 2010/0100167 A1 | 4/2010 | Bortlein et al. | |
| 2010/0100176 A1 | 4/2010 | Elizondo et al. | |
| 2010/0131054 A1 | 5/2010 | Tuval et al. | |
| 2010/0137979 A1 | 6/2010 | Tuval et al. | |
| 2010/0145439 A1 | 6/2010 | Seguin et al. | |
| 2010/0152840 A1 | 6/2010 | Seguin et al. | |
| 2010/0161045 A1 | 6/2010 | Righini | |
| 2010/0168844 A1 | 7/2010 | Toomes et al. | |
| 2010/0198346 A1 | 8/2010 | Keogh et al. | |
| 2010/0234940 A1 | 9/2010 | Dolan | |
| 2010/0249923 A1 | 9/2010 | Alkhatib et al. | |
| 2010/0256723 A1 | 10/2010 | Murray | |
| 2011/0022157 A1 | 1/2011 | Essinger et al. | |
| 2011/0040366 A1 | 2/2011 | Goetz | |
| 2011/0040374 A1* | 2/2011 | Goetz | A61F 2/2418 623/2.11 |
| 2011/0056064 A1 | 3/2011 | Malewicz et al. | |
| 2011/0060404 A1 | 3/2011 | Malewicz et al. | |
| 2011/0106246 A1 | 5/2011 | Malewicz et al. | |
| 2012/0165544 A1 | 6/2012 | Dochnahl et al. | |
| 2012/0271398 A1 | 10/2012 | Essinger et al. | |
| 2012/0277734 A1 | 11/2012 | Goetz | |
| 2013/0046373 A1* | 2/2013 | Cartledge | A61F 2/95 623/1.11 |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 10 074 | 10/2001 |
| DE | 100 49 812 | 4/2002 |
| DE | 100 49 813 | 4/2002 |
| DE | 100 49 815 | 4/2002 |
| EP | 0664107 | 7/1995 |
| EP | 1057460 A1 | 6/2000 |
| EP | 1255510 | 11/2002 |
| EP | 1469797 | 11/2005 |
| EP | 1842508 | 10/2007 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/44313 | 8/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 02/49540 | 6/2002 |
| WO | 03/003943 | 1/2003 |
| WO | 03/003949 | 1/2003 |
| WO | 03/011195 | 2/2003 |
| WO | 04/019825 | 3/2004 |
| WO | 04/082527 | 9/2004 |
| WO | 04/089250 | 10/2004 |
| WO | 05/004753 | 1/2005 |
| WO | 05/046528 | 5/2005 |
| WO | 05/084595 | 9/2005 |
| WO | 06/026371 | 3/2006 |
| WO | 07/002166 | 1/2007 |
| WO | 08/029296 | 3/2008 |
| WO | 08/047354 | 4/2008 |
| WO | 08/138584 | 11/2008 |
| WO | 08/150529 | 12/2008 |
| WO | 09/002548 | 12/2008 |
| WO | 09/029199 | 3/2009 |
| WO | 09/042196 | 4/2009 |
| WO | 09/045338 | 4/2009 |
| WO | 09/061389 | 5/2009 |
| WO | 09/091509 | 7/2009 |
| WO | 09/111241 | 9/2009 |
| WO | 12/032187 | 3/2012 |

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with

(56) References Cited

OTHER PUBLICATIONS

Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004; 25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio Thoracic Surgery, 28:194-198, 2005.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Pavcnik et al., "Aortic and venous valve for percutaneous insertion," Min. Invas. Ther. & Allied Techol. 2000, vol. 9, pp. 287-292.

* cited by examiner

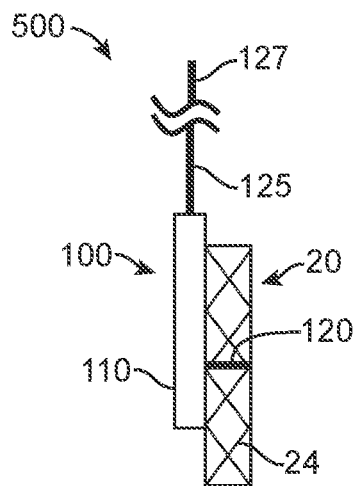
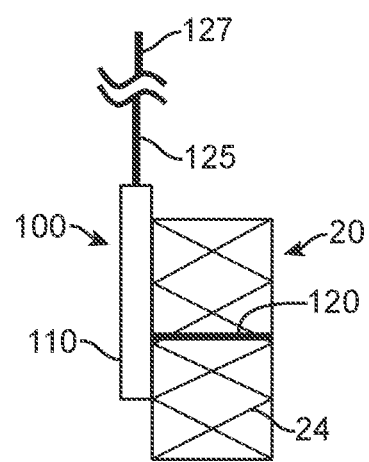
FIG. 1A          FIG. 1B
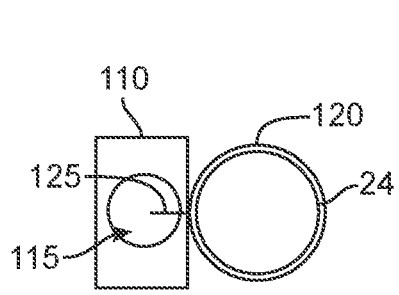
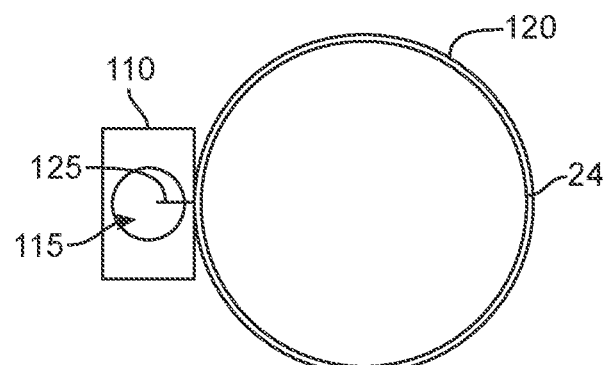
FIG. 2A          FIG. 2B

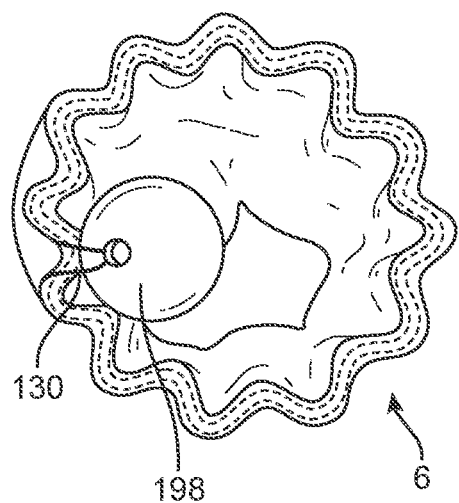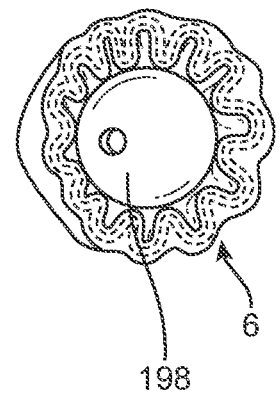
FIG. 36A  FIG. 36B
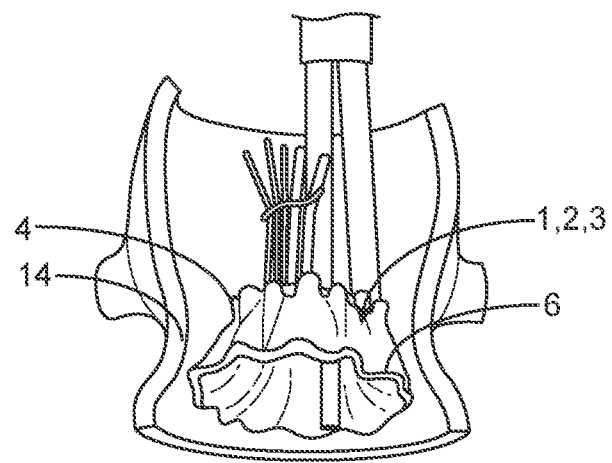
FIG. 37

VALVE DELIVERY TOOL

RELATED APPLICATIONS

The application is a Continuation of and claims the benefit of U.S. patent application Ser. No. 14/268,375, filed May 2, 2104, which claims the benefit of U.S. Provisional Patent Application No. 61/819,488, filed on May 3, 2013; U.S. Provisional Patent Application No. 61/819,492, filed on May 3, 2013; U.S. Provisional Patent Application No. 61/819,490, filed on May 3, 2013; and U.S. Provisional Patent Application No. 61/930,905, filed on Jan. 23, 2014, each of which is hereby incorporated herein in its entirety to the extent that it does not conflict with the disclosure presented herein.

FIELD

The present disclosure relates to, among other things, tools for delivering implantable medical devices having self-expanding frames, such as prosthetic heart valves.

BACKGROUND

A number of self-expanding implantable medical devices, such as prosthetic heart valves that have self-expanding frames, are known. A number of delivery systems and tools to aid in implanting such medical devices are known. However, improved delivery tools or systems or associated devices that can aid in implanting such devices are desired.

SUMMARY OF SOME EMBODIMENTS

In some embodiments, minimally invasive sutureless valve delivery tools are described herein.

In some embodiments, the delivery tools comprise a side mounted holder.

Some embodiments of the delivery tools described herein are easy to use.

In various embodiments, tool described herein allow rapid and simple connection with the valve.

In some embodiments, tools described herein allow a surgeon to visualize the seating of the valve at a patient's annulus.

Various embodiments of the tools described herein allow a surgeon to have solid control over valve positioning while expanding the valve at a desirable rate.

In some embodiments, the tools are configured to allow improved visualization by flaring the skirt during deployment and by using a low profile or side mounted interface between the handle and the valve.

In various embodiments, the tools described herein allow for easy repositioning of the valve. For example, a handle of the tool may be readily reconnected to the valve if the surgeon is not satisfied with valve placement.

Advantages of one or more of the various embodiments presented herein over prior devices for implanting in a valve sinus of a patient, such as prosthetic heart valves, and associated methods will be readily apparent to those of skill in the art based on the following detailed description when read in conjunction with the accompanying drawings.

BRIEF DESCRIPTION OF THE DRAWINGS

FIGS. 1A-B are schematic drawings of side views of an embodiment of a holder and self-expanding implantable medical device, where the device is in a constricted configuration (1A) and an expanded configuration (1B).

FIGS. 2A-B are schematic drawings of top views of an embodiment of a holder and self-expanding implantable medical device, where the device is in a constricted configuration (2A) and an expanded configuration (2B).

FIGS. 36A-B are schematic drawings of an embodiment of a holder having crimp limiting elements and an associated prosthetic valve.

FIG. 37 is a schematic drawing of an embodiment of a holder and an embodiment of a prosthetic valve in a mock-up of a valve sinus.

FIGS. 47A-E are top views of the sizers shown in the perspective views of FIGS. 47F-J, respectively.

Figure 3:
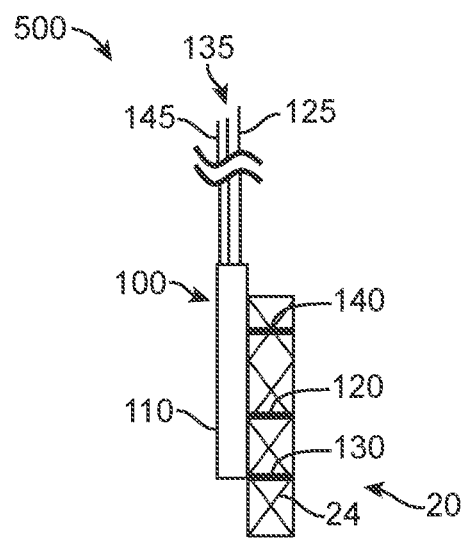
FIG. 3 is a schematic drawing of a side view of an embodiment of a holder and self-expanding implantable medical device.

The schematic drawings in are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

Described herein, among other things, are devices, systems and methods for implanting medical devices having a self-expanding frame in a patient. In some embodiments, the medical devices are configured to be implanted in a valve sinus of a patient. In some embodiments, the medical devices are prosthetic heart valves. In some embodiments, the medical devices are surgical prosthetic heart valves.

Some of the devices and systems described herein are holders for retaining self-expanding medical devices in a constricted configuration and for controlling expansion of the medical device. Delivery tools that can work cooperatively with such holders and that can aid in positioning the self-expanding medical device or controlling expansion of the device are also described.

Methods for implanting devices using such tools and systems are also described, as well as additional tools or devices, such as sizers or crimpers, to facilitate the implant process are also described.

Initially a conceptual overview of holders for retaining a self-expanding medical device in a constricted configuration and for controlling expansion of the device are described herein. Then, anatomical features of a valve of a subject and examples of prosthetic heart valves configured to be implanted in a native valve of a subject are described. Some embodiments of holders and delivery tools useful for implanting heart valves in a native valve are then described. A description of accessory devices that can aid in the implantation of prosthetic heart valves is then provided, followed by a summary of some selected embodiments of holders, systems including holders, and associated implant methods is provided.

FIGS. 1-9 illustrate conceptual overviews of generic systems and devices for delivering a self-expanding medical device to a target location of a patient. FIGS. 10-19 illustrate anatomical features of a valve and examples of prosthetic heart valves. FIGS. 20-42 illustrate some more specific embodiments of systems and devices for implanting self-expanding prosthetic heart valves in a valve of a patient. FIGS. 43-52 illustrate sizers and other accessory devices or tools that can be helpful in implanting a prosthetic heart valve. FIGS. 53-74 illustrate additional embodiments of systems and devices for implanting self-expanding prostheses.

I. Overview of Generic Retaining or Delivering Systems and Devices

Referring to FIGS. 1-2, a system 500 that includes a holder 100 and a medical device 20 is shown. The medical device 20 has a self-expanding frame 24. The medical device 20 may be configured for implantation in a valve of a subject. In embodiments, the medical device 20 is a prosthetic heart valve, such as a sutureless surgical heart valve. The holder 100 is configured to retain the frame 24 of the implantable medical device in a constricted configuration and to control expansion of the frame. In FIGS. 1A (side view) and 2A (top view), the frame 24 is in a constricted configuration, and in FIGS. 1B (side view) and 2B (top view) the frame 24 is in an expanded configuration.

The holder 200 includes a controllably constrictable and expandable loop 120. As used herein, "constrictable and expandable loop" means that the size of an opening defined by the loop may be made smaller (constricted) or larger (expanded). The loop 120 is disposed about at least a portion of the self-expanding frame 24 such that constriction or expansion of the loop controls constriction or expansion of the frame. For purposes of the present disclosure "control of constriction or expansion of the frame" includes control of constriction or expansion of at least a portion of the frame.

The extent to which the frame may be constricted by the holder or a system including the holder can be limited, because some frames may be damaged if crimped to a diameter that is too small. Any suitable crimp limiting mechanism may be used. For example, a crimp limiter that limits the extent to which a loop may be constricted may be employed. By way of further example, a crimp limited that limits the extent that a frame can be constricted by be employed. Some examples of crimp limiters are described below in more detail with regard to more specific embodiments.

In some embodiments (e.g., as depicted in FIGS. 1-2), the loop 120 is formed from a portion of a cord 125. A portion of the cord 125 extends through a conduit 115 in extension member 110 of the holder such that an end 127 of the cord 125 extends beyond the extension member 110. Maintenance of tension on the cord 125 retains the loop 120 in a relatively constricted state (e.g., FIGS. 1A and 2A). Release of some tension on the cord 125 allows the loop 120 to expand as the frame 24 of the implantable medical device 20 self-expands (e.g., FIGS. 1B and 2B).

Referring now to FIG. 3, a side view of an embodiment of a system 500 including a holder 100 and an implantable medical device 20 having a self-expandable frame 24 is shown. The embodiment shown in FIG. 3 is similar to the embodiment shown in FIG. 1A, with like numbers referring to like components. In the embodiment depicted in FIG. 3, the holder 100 include three loops 120, 130, 140 for controlling the expansion of the frame 24 of the device (e.g., as described above with regard to loop 120 in FIGS. 1-2). The loops 120, 130, 140 may each be independently constrictable and expandable or one or more of the loops may be dependently contstrictable or expandable (e.g., constriction of one loop results in constriction of another loop). When used with devices where a constriction of the frame in one location (e.g., around the circumference in the middle of the frame) is not sufficient to prevent expansion of other portions of the frame (e.g., expansion of the top or bottom), more than one loop may be advantageously employed.

As shown in the embodiment depicted in FIG. 3, each loop 120, 130, 140 is part of a cord 125, 135 145. The cords 125, 135 145 extend through one or more conduits (not shown) of extension member 110. In some embodiments, all of the loops extend through the same conduit. In some embodiments, each cord extends through a separate conduit. In some embodiments, cords of loops that are dependently constrictable and expandable extend through the same conduit.

It will be understood that a holder may include any suitable number of loops, such as one (as depicted in FIGS. 1-2), two, three (e.g., as depicted in FIG. 3), four, five or more. Any one or more of the loops may be independently or dependently constrictable and expandable. In some embodiments, at least one loop is independently constrictable and expandable relative to at least one other loop.

Figures 4A, 4B:
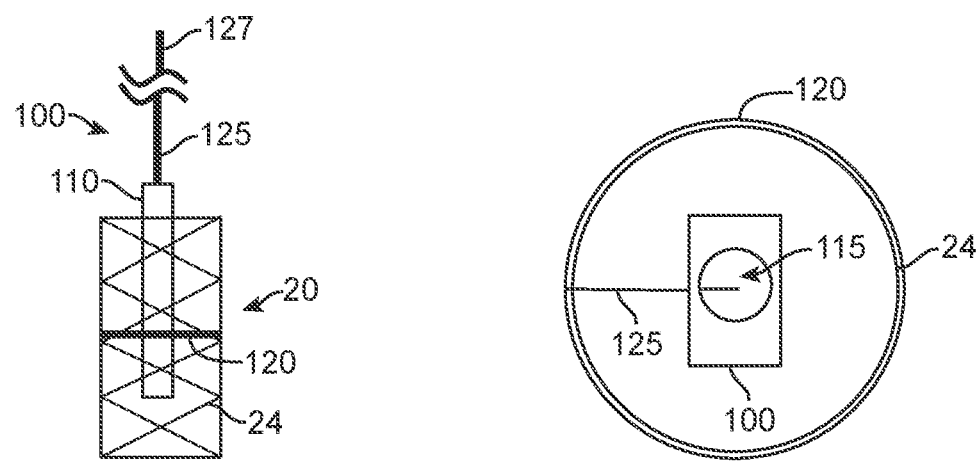
FIGS. 4A-B are schematic drawings of a side view (4A) and a top view (4B) of an embodiment of a holder and self-expanding implantable medical device.

Referring now FIGS. 4A-B, a side view of an embodiment of system including a holder 100 and device 20 having an expandable frame 24 is shown. The system depicted in FIGS. 4A and 4B is similar to the embodiment depicted in FIGS. 1A and 1B (with like numbers referring to like components) except that extension 110 of holder is positioned at least partially within a central opening of frame 24. Extension 110 may be aligned with the longitudinal axis of the frame 24 as depicted. Alternatively, extension 110 may be offset from the longitudinal axis of the frame, may deviate from the axis by an angle, or the like. For example, in the embodiment depicted in FIG. 1A, the extension is offset from, and parallel to, the longitudinal axis of the frame 24.

As shown in FIG. 4B, when a portion of the extension 110 from which the loop 120 or cord 125 that forms the loop is positioned within a central opening of frame 24, a portion of the loop or cord extends from with the central opening of the frame to an edge of the frame so that the loop 120 may restrain at least a portion of the frame 24.

A holder may have any suitable number of extensions, such as one, two, three, four, five, or more. In some embodiments, a holder has one extension for each loop or cord. In some embodiments, a holder has more extensions than loops or cords, with more than one cord running through at least one extension. As discussed above, each extension may have any suitable number of conduits. In some embodiments, an extension has a sufficient number of conduits such that each cord that runs through the extension runs through a separate conduit. In some embodiments, more than one cord extends through a given conduit of an extension.

Figure 5:
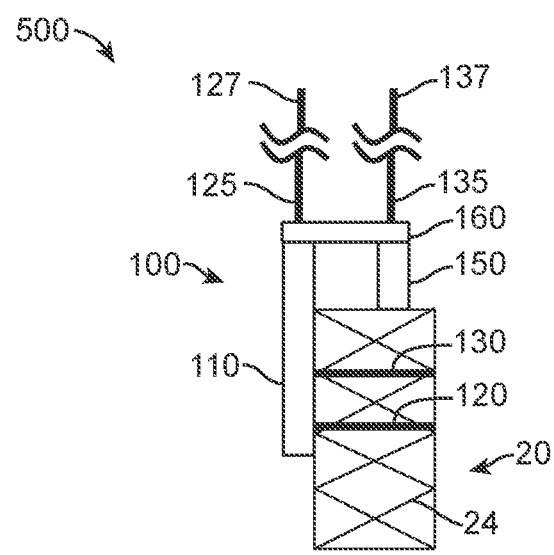
FIG. 5 is a schematic drawing of a side view of an embodiment of a holder and self-expanding implantable medical device.

Referring now to FIG. 5, an embodiment of a system 500 including a holder 100 and an implantable medical device 20 having a self-expanding frame 24 is shown. The depicted holder 100 has a first extension member 110 and a second extension member 150. The extension members 110, 150 are offset from, and substantially parallel to, the longitudinal axis of the frame 24 and are positioned external to the frame. Alternatively, the extension members may be positioned such that at least a portion is within a central opening of the frame or such that one is within the frame and another is external to the frame. As discussed above, any given extension member may be aligned with the longitudinal axis of the frame, offset from the longitudinal axis of the frame, parallel to the longitudinal axis, extend at an angle from the longitudinal axis, or the like.

In the embodiment depicted in FIG. 5, the first loop 120 is a part of a first cord 125 that extends through a conduit of the first extension member 110 such that an end 127 of the cord 125 extends beyond the first extension member 110. The second loop 130 is a part of a second cord 135 that extends through a conduit of the second extension member 150 such that an end 137 of the cord 135 extends beyond the second extension member 110. The holder 110 includes an adaptor 160 through which a portion of the first 125 and second 135 cords extend. The adaptor 160 may be a separate component from, or part of the same component as, one or both of the extensions 120, 150. The adaptor 160 preferably retains the relative positions of the first 120 and second 150 extension members. The adaptor 160 may also be configured to cooperatively mate with a shaft of a delivery device, which will be discussed below in various embodiments.

Figure 6:
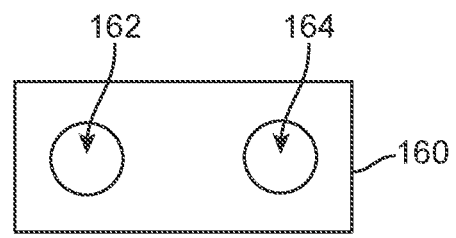
FIG. 6 is a schematic drawing of a top view of an embodiment of an adaptor of a holder.

Referring now to FIG. 6, a top view of the adaptor 160 depicted in FIG. 5 is shown. The adaptor 160 has a first lumen 162 and a second lumen 164 that extend through the adaptor 160. With reference to both FIGS. 5 and 6, the first cord 125 extends through the first lumen 162 of the adaptor 160 and the second cord 135 extends through the second lumen 164 of the adaptor.

An adaptor may have any number of lumens through which the cords may extend. In some embodiments, an adaptor has a single lumen through which all the cords extend. In some embodiments, an adaptor has a sufficient number of lumens for each cord to extend through a separate lumen. In some embodiments, more than one cord extends through a lumen of an adaptor.

Figure 7:
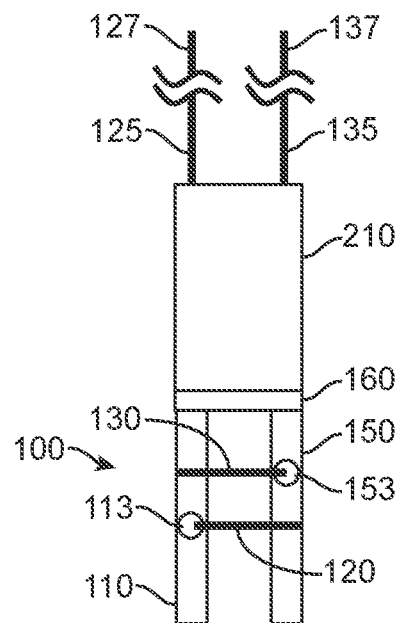
FIGS. 7-9 are schematic drawings of side views of embodiments of delivery systems, or components thereof.

Referring now to FIG. 7, a holder 100 and shaft 210 are depicted. The holder is similar to the holder depicted in FIG. 6, with similar numerical identifiers referring to similar components. The holder 100 in FIG. 7 includes a first loop 120 as a part of a first cord 125 having an end 127, a second loop 130 as a part of a second cord 135 having an end 137, a first extension member 110, a second extension member 150, and an adaptor 160. The first extension member 110 includes an opening 113 through which the first loop 120 or cord 125 exits, and the second extension member 150 includes an opening 153 through which the second loop 130 or cord 135 exits. It will be understood that openings 113, 153 may be positioned in at any suitable location of the extension members 110, 150 and the locations depicted in FIG. 7 is merely for purposes of example. The first 125 and second 135 cords extend through the extension members adaptor and shaft such that an end 127, 137 of the cords extends beyond the shaft 210. The end portions 127, 137 of the cords 125, 135 are configured to be coupled to one or more actuation mechanisms (not shown) that are configured to control constriction and expansion of the loops 120, 130. The shaft 210 may include one or more lumens through which the cords may extend.

A shaft may have any suitable number of lumens. In some embodiments, a shaft has a single lumen through which all the cords extend. In some embodiments, a shaft has a sufficient number of lumens for each cord to extend through a separate lumen. In some embodiments, more than one cord extends through a lumen of a shaft.

Figure 8:
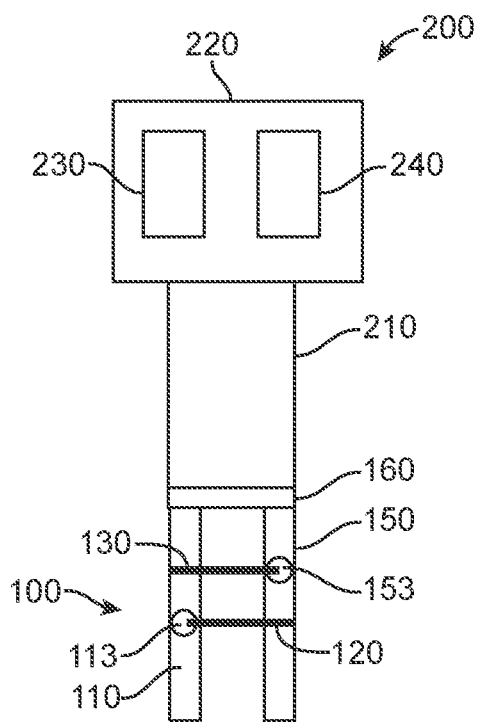

Referring now to FIG. 8, an embodiment of a holder 100 and delivery tool or system 200 are shown. The embodiment depicted in FIG. 8 is similar to the embodiment depicted in FIG. 7, with like numbers referring to like components. In FIG. 8, the delivery tool 200 includes a handle 220 having actuation elements 230, 240 operably coupled to a tension apparatus configured to control constriction and expansion of loops 120, 130. Handle 220 is attached to shaft 210 or handle 220 and shaft 210 may be formed as a single component. The shaft 210 and handle 220 are sufficiently rigid or have sufficiently rigid components to allow a user to grasp the handle or shaft and direct a self-expanding medical device to a desired implant location. In the depicted embodiments, the handle has two actuation elements 230, 240 (each independently coupled to a separate tension apparatus) so that one actuation element may control one loop and the other actuation element may control the other loop.

In some embodiments, more than one loop can be controlled by a single actuation element.

Figure 9:
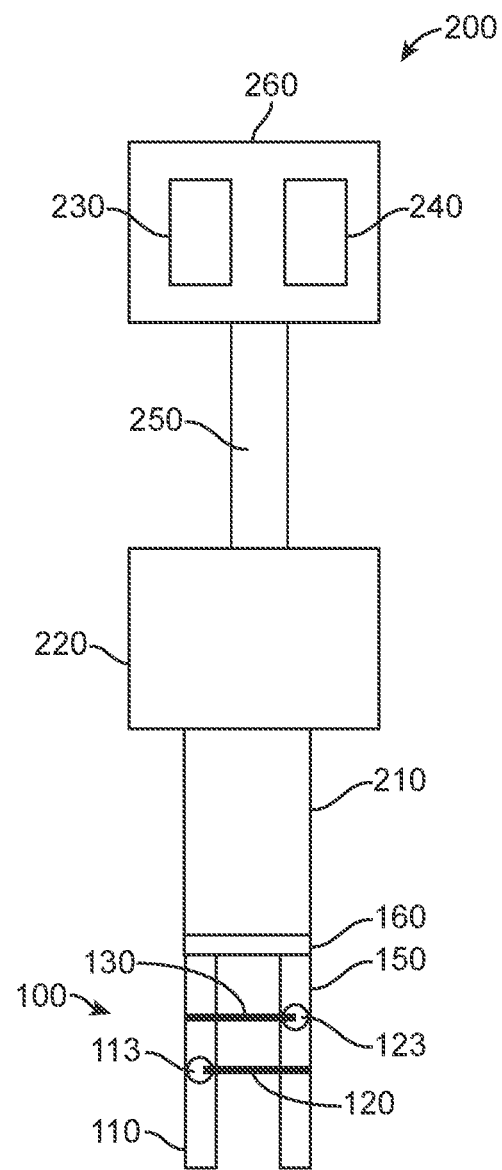

Referring now to FIG. 9, an embodiment of a holder 100 and delivery tool or system 200 are shown. The embodiment depicted in FIG. 9 is similar to the embodiment depicted in FIGS. 7 and 8, with like numbers referring to like components. In FIG. 9, the delivery tool 200 includes a control unit 260 attached to handle 220 via a tether 250. The control unit 260 includes actuation elements 230, 240 (operably coupled to tension apparatus that may be housed in, for example, the handle or the control unit) for controlling constriction and expansion of loops 120, 130. A tool 200 as depicted in FIG. 9 allows for one to position the self-expanding medical device (which would be retained by holder 100) with one hand and to control constriction and expansion of loops 120, 130 via actuation elements 230, 240 with another hand. Alternatively, one person could position the device at the proper implant location by grasping the shaft 210 or handle 220 and another could control the loops 120,130 via actuation elements 230, 240 of control unit 260. In some embodiments, the cords (not shown in FIG. 9) are coupled with actuation elements 230, 240 in the control unit 260. In some embodiments, the cords are coupled with a portion of an actuation assembly that is a part of the handle or shaft, which portions of the actuation assembly are controlled via actuation elements actuation elements 230, 240 in the control unit 260.

The discussion above with regard to FIGS. 1-9 is intended to be generic with regard to devices that may be implanted and holders and delivery tools for implanting the devices. It will be understood that the aspects, components, or both the aspects or components depicted in or discussed with regard to FIGS. 1-9 are interchangeable. For example, a discussion above with regard to FIG. 1A may also apply to a discussion with regard to FIG. 9 as appropriate, and vice-versa.

In some embodiments, a device implantable using a holder or delivery system as described herein is a self-expanding device or a device having a self-expanding component that is configured to be implanted in a native valve of a subject. In various embodiments, the device comprises a frame having an annular portion configured to be aligned with the annulus of the native valve. In some embodiments, the device to be implanted is a prosthetic heart valve.

The frame, in some embodiments, is expandable from a collapsed configuration to an expanded configuration in a controlled manner using a holder or delivery system as described herein. In the expanded configuration in some of such embodiments, the annular portion of the frame is configured to engage the annulus of the native valve. The frame may be configured to be at least partially collapsed from the expanded configuration to an at least partially collapsed configuration using a holder or delivery system described herein such that the frame can be repositioned during an implant procedure if the frame is not properly aligned with the annulus of the native valve.

In some embodiments, the frame has a flange positioned superior to the annular portion when implanted, wherein the flange is compressible and expandable. The flange may be a part of a concave-shaped portion configured to anchor the device around the annulus. In some embodiments, at least one loop of a holder is positioned around at least a portion of the flange to control expansion of the flange during an implant procedure.

II. Anatomical Features of a Valve and Examples of Prosthetic Heart Valves

Prior to describing specific embodiments of holders and delivery systems that may be advantageously employed for delivering prosthetic heart valves to a heart valve of a patient, a general description of heart valve device components and heart valve anatomy is provided with regard to FIGS. 10-19.

Figure 10A:
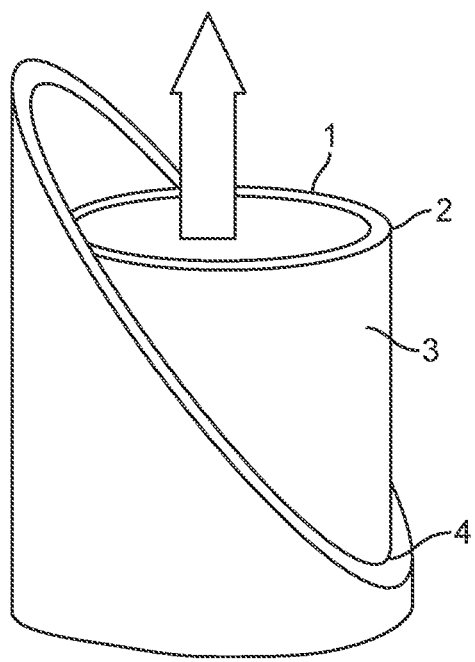
FIG. 10A is a schematic drawing of an exemplary valve in an open position during peak flow.
Figure 10B:
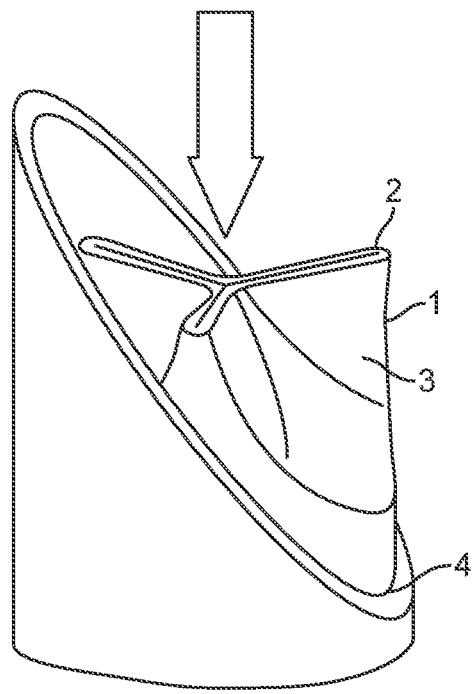
FIG. 10B is a schematic drawing of the valve of FIG. 10A in a closed position to prevent backflow of the fluid across the valve.

FIGS. 10A and 10B generally illustrate one exemplary embodiment of a heart valve 1. As illustrated in FIG. 10, valve 1 includes a distal outflow end 2, a plurality of leaflets 3, and a proximal inflow end 4. A typical valve functions similar to a collapsible tube in that it opens widely during systole or in response to muscular contraction to enable unobstructed forward flow across the valvular orifice, as illustrated in FIG. 10A. In contrast, as forward flow decelerates at the end of systole or contraction, the walls of the tube are forced centrally between the sites of attachment to the vessel wall and the valve closes completely as illustrated in FIG. 10B.

Figure 11A:
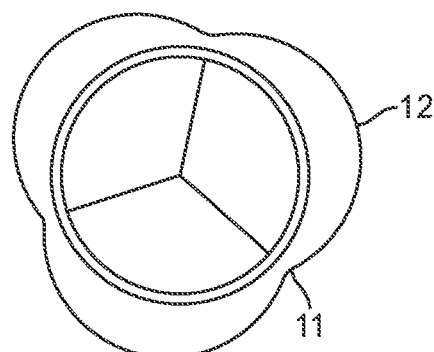
FIG. 11A is a schematic drawing of a top view illustrating the anatomy of a typical aortic valve.
Figure 11B:
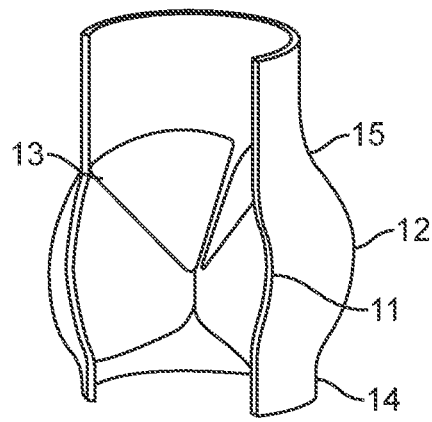
FIG. 11B is a schematic drawing of a cross-sectional view of the aortic valve of FIG. 11A.
Figure 11C:
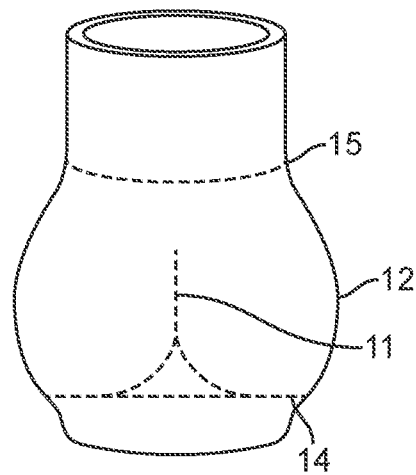
FIG. 11C is a schematic perspective view of the aortic valve of FIG. 11A showing the inflow end, outflow end, and commissural posts in phantom lines.

FIGS. 11A, 11B, and 11C illustrate the anatomy of a typical aortic valve. In particular, FIG. 11A shows a top view of a closed valve with three valve sinuses, FIG. 11B shows a perspective sectional view of the closed valve, and FIG. 11C shows a view from outside the vessel wall.

One consideration in the design of valve replacement systems and devices is the architecture of the valve to be replaced. For example, mitral and tricuspid heart valves do not have valve sinuses whereas aortic and pulmonic heart valves have valve sinuses. Valve sinuses 12 are dilations of the vessel wall that surround the natural valve leaflets. Typically in the aortic valve, each natural valve leaflet has a separate sinus bulge 12 or cavity that allows for maximal opening of the leaflet at peak flow without permitting contact between the leaflet and the vessel wall. As illustrated in FIGS. 11A, 11B, and 11C, the extent of the sinus 12 is generally defined by the commissures 11, vessel wall 13, inflow end 14, and outflow end 15. The proximal intersection between the sinus cavities define the commissures 11.

FIGS. 11B and 11C also show the narrowing diameter of the sinuses at both inflow end 14 and outflow end 15, thus forming the inflow and outflow annuli of the sinus region. Thus, the valve sinuses form a natural compartment to support the operation of the valve by preventing contact between the leaflets and the vessel wall, which, in turn, may lead to adherence of the leaflets and/or result in detrimental wear and tear of the leaflets. The valve sinuses are also designed to share the stress conditions imposed on the valve leaflets during closure when fluid pressure on the closed leaflets is greatest. The valve sinuses further create favorable fluid dynamics through currents that soften an otherwise abrupt closure of the leaflets under conditions of high backflow pressure. Lastly, the sinuses ensure constant flow to any vessels located within the sinus cavities.

Figure 12:
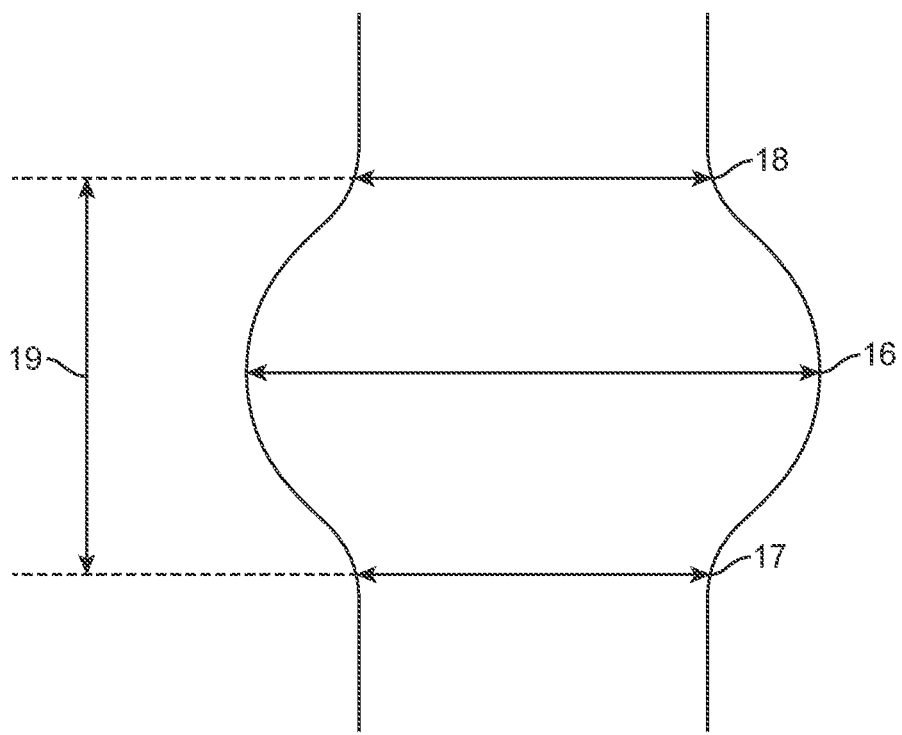
FIG. 12 is a schematic representation of the geometry and relative dimensions of the valve sinus region.

FIG. 12 is a schematic representation of the geometry and relative dimensions of the valve sinus region. As shown in FIG. 12, the valve sinus region is characterized by certain relative dimensions which remain substantially constant regardless of the actual size of the sinuses. Generally, the diameter of the sinus is at its largest at the center of the sinus cavities 16, while there is pronounced narrowing of the sinus region at both the inflow annulus 17 near the inflow end 14 and the outflow annulus 18 near the outflow end 15. Furthermore, the height of the sinus 19 (i.e. the distance between inflow annulus 17 and outflow annulus 18) remains substantially proportional to its overall dimensions. It is thus apparent that the sinus region forms an anatomical compartment with certain constant features that are uniquely adapted to house a valve. The systems and devices disclosed herein may be designed to utilize these anatomical features of the native sinus region for replacement valve function and positioning.

Figure 13:
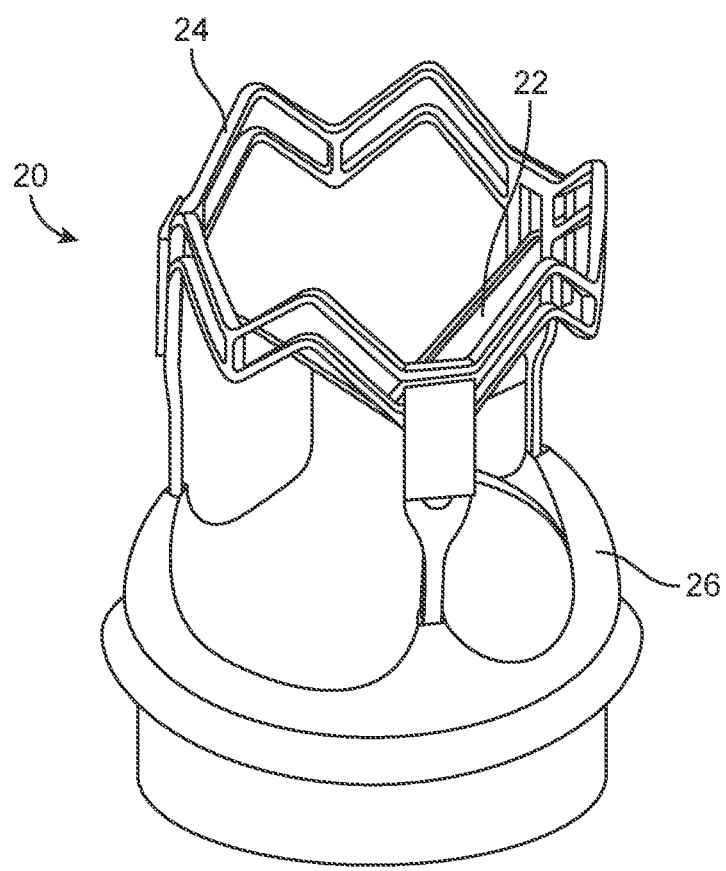
FIG. 13 is a schematic perspective view of a valve replacement system, which includes a replacement valve, a valve support structure (or "frame"), and a valve cuff.

FIG. 13 is a perspective view of a valve replacement system 20 described in more detail in US Published Patent Application No. 2010/0168844 (which application is hereby incorporated by reference in its entirety to the extent that it does not conflict with the disclosure presented herein), which contains general features of the valves described in more detail below. Such valves, as well as the valve depicted in FIG. 4, include replacement valve 22, valve support structure or frame 24, and valve cuff 26. Replacement valve 22 may be attached to frame 24 such that replacement valve 22 resides within the support structure. Valve support structure 24 may be, for example, an expandable and collapsible stent-like frame structure adapted to be delivered to an implantation site such as a native heart valve. Frame 24 may be either self-expanding or non-self-expanding, and may be delivered to the target site via any suitable delivery means as will be appreciated by one skilled in the art. Valve cuff 26 is attachable to the inflow end of replacement valve 22, and may be structured to reduce paravalvular leakage around the valve, as well as to reduce migration and increase stability of replacement valve 22 after implantation at the implantation site.

Replacement valve 22 illustrated in FIG. 13 is a tri-leaflet valve. For purposes of example and not limitation, the following discussion will reference only valve 22, it being understood that any stented or stentless replacement valve is contemplated. Similarly, although valve frame 24 is shown as structured to receive a tri-leaflet valve, those skilled in the art will appreciate that replacement valves having a number of leaflets other than three will correspondingly require a different valve support structure.

Figure 14:
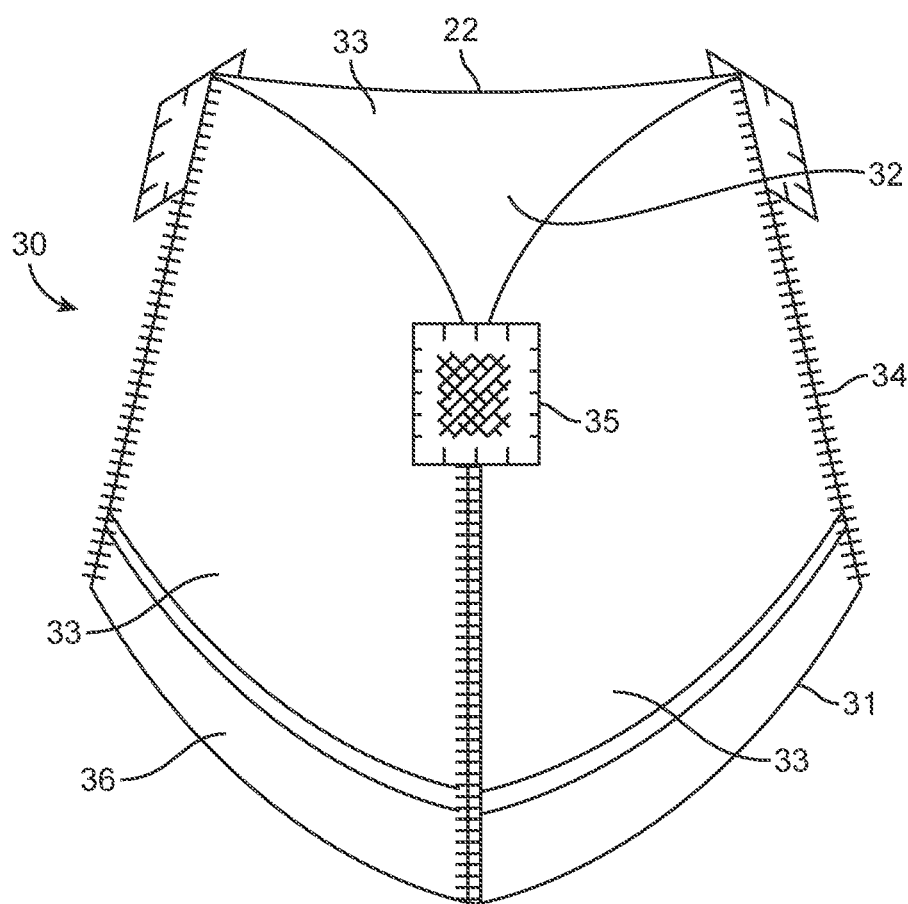
FIG. 14 is a schematic perspective view of the replacement valve of FIG. 13.

FIG. 14 is a perspective view of replacement valve 22, which represents one exemplary embodiment of a tri-leaflet replacement valve useable with valve replacement systems 20 described herein. Replacement valve 22 includes valve body 30 having proximal inflow end 31 and a distal outflow end 32. Valve body 30 includes a plurality of valve tissue leaflets 33 joined by seams 34, wherein each seam 34 is formed by a junction of two leaflets 33. A commissural tab region 35 extends from each seam 34 at the distal end of valve body 30. Inflow end 31 of valve body 30 includes a peripheral edge that may be scalloped or straight. In addition, inflow end 31 of valve body 30 may further comprise reinforcement structure 36 that may be stitched or otherwise attached thereto.

The valve replacement systems and devices described herein are not limited, however, to the specific valve illustrated in FIG. 14. For example, although the proximal inflow end 31 of valve body 30 is shown in FIG. 14 with a scalloped peripheral edge, other shapes and configurations are contemplated and within the intended scope of the present disclosure.

Valve leaflets 33 may be constructed of any suitable material, including but not limited to polymeric materials, metallic materials, and/or tissue-engineered materials. For example, bovine, porcine, equine, ovine, and/or other suitable animal tissues may be used to construct valve leaflets. In some embodiments, valve leaflets may be constructed of or formed from material obtained from, for example, heart valves, aortic roots, aortic walls, aortic leaflets, pericardial tissue, blood vessels, intestinal submucosal tissue, umbilical tissue and the like from humans or animals. In some embodiments, valve leaflets may be constructed of expanded polytetrafluoroethylene (ePTFE), equine pericardium, bovine pericardium, or native porcine valve leaflets similar to currently available bioprosthetic aortic valves. Other materials may prove suitable as will be appreciated by one skilled in the art.

Figure 15:
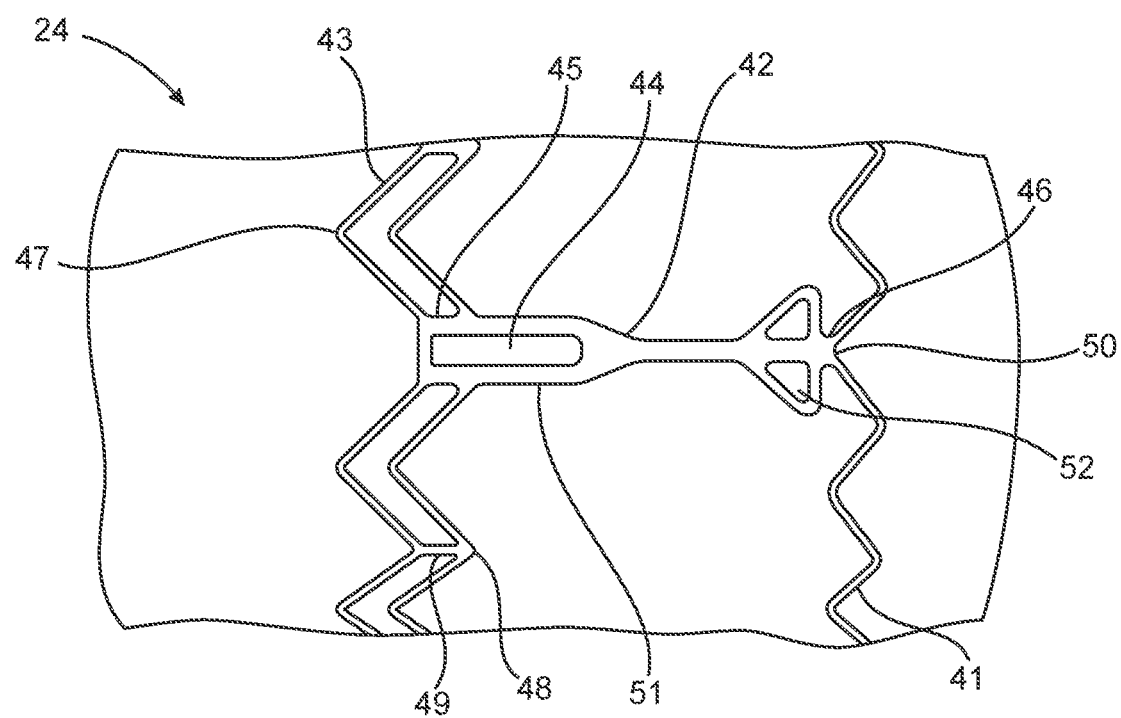
FIG. 15 is a schematic side view of the valve support structure of FIG. 13 disposed inside a vessel.

FIG. 15 is a side view of valve support structure 24, which represents one exemplary embodiment of a typical support structure useable with valve replacement system 20 in accordance with the teaching presented herein. In general, valve support structure 24 is designed as a collapsible and expandable anchoring structure that may be adapted to support valve 22 distally along commissural tab region 35 and proximally along the proximal inflow end 31. As shown in FIG. 15, valve 22 and valve cuff 26 have been detached from valve frame 24 so as to focus on the structure and features of the support structure.

In some embodiments, valve frame 24 has a generally tubular configuration within which replacement valve 22 may be secured, and includes inflow rim 41, support posts 42 and outflow rim 43. Replacement valve 22 may be secured at the proximal inflow end 31 by attachment to inflow rim 41 of support structure 24 and at the distal outflow end 32 via commissural tabs 35 that are threaded through axially extending slots 44, which are formed in support posts 42 that extend longitudinally from inflow rim 41 to outflow rim 43 of valve support structure 24. Thus, distal ends 45 of support posts 42 contact outflow rim 43 of valve support structure 24, whereas proximal ends 46 of support posts 42 contact inflow rim 41 of valve support structure 24.

In the embodiment shown in FIG. 15, outflow rim 43 of support structure 24 is depicted as comprising a plurality of rings that extend between support posts 42 generally at or above the axially extending slots 44 that reside therein. The plurality of rings of outflow rim 43 are configured in an undulating or zigzag pattern forming peaks 47 and valleys 48, wherein the individual rings remain substantially parallel to one another. The plurality of rings of outflow rim 43 may include a vertical connector element 49 positioned at the center of valleys 48 formed by the undulating or zigzag pattern. Vertical connector element 49 is designed to stabilize frame 24 and to prevent distortion of the valve during compression and expansion of the frame. Vertical element 49 extends longitudinally in the axial direction of the cylindrical valve support structure 24.

In the embodiment of valve support structure 24 illustrated in FIG. 15, outflow rim 43 is formed with two rings, while inflow rim 41 is formed with a single ring that extends between support posts 42. However, the number of rings is not important, and numerous other configurations are contemplated.

Both inflow rim 41 and outflow rim 43 of valve support structure 24 are formed with an undulating or zigzag configuration. In various embodiments of valve support structures, inflow rim 41 may have a shorter or longer wavelength (i.e., circumferential dimension from peak to peak) and/or a lesser or greater wave height (i.e., axial dimension from peak to peak) than outflow rim 43. The wavelengths and wave heights of inflow rim 41 and outflow rim 43 may be selected to ensure uniform compression and expansion of valve support structure 24 without substantial distortion. The wavelength of inflow rim 41 is further selected to support the geometry of the inflow end of the valve attached thereto, such as the scalloped inflow end 31 of replacement valve 22 shown in FIG. 14. Notably, as shown in FIG. 15, the undulating or zigzag pattern that forms inflow rim 41 of valve support structure 24 is configured such that proximal ends 46 of vertical support posts 42 are connected to peaks 50 of inflow rim 41. Similarly, the undulating or zigzag pattern that forms outflow rim 43 of support structure 24 is configured such that distal ends 45 of support posts 42 are connected to valleys 48 of outflow rim 43. Locating distal ends 45 of support posts 42 at valleys 48 of outflow rim 43 may prevent the longitudinal extension of outflow rim 43 in the direction of replacement valve 22 secured within the lumen of valve support structure 24 upon compression of the replacement valve assembly 20. As a result, most, if not all, contact between replacement valve 22 and valve support structure 24 is eliminated. Likewise, locating proximal ends 46 of support posts 42 at peaks 50 of inflow rim 41 may prevent longitudinal extension of inflow rim 41 in the direction of the valve tissue. Thus, compression of replacement valve 22 and valve support structure 24 does not lead to distortion of or injury to the valve.

FIG. 15 further shows that support posts 42 are configured generally in the shape of a paddle with axial slot 44 extending internally within blade 51 of the paddle. Blade 51 of the paddle is oriented toward outflow rim 43 of support structure 24 and connects to outflow rim 43 at a valley 48 of the undulating or zigzag pattern of outflow rim 43. An important function of support posts 42 is the stabilization of valve 22 in general, and in particular the prevention of any longitudinal extension at points of valve attachment to preclude valve stretching or distortion upon compression of replacement valve system 20. Blades 51 of the paddle-shaped support posts 42 may be designed to accommodate commissural tabs 35 of valve 22.

Support posts 42 further comprise triangular shaped elements 52 extending on each side of proximal end 46 of the support post. Triangular shaped elements 52 may be designed to serve as attachments sites for valve cuff 26 and may be designed in different shapes without losing their function. Thus, the particular design of elements 52 shown in FIG. 15 is not critical to the attachment of valve cuff 26, and numerous other designs and shapes are contemplated and within the intended scope of the present disclosure.

The number of support posts 42 generally ranges from two to four, and generally depends on the number of commissures and leaflets present in the replacement valve 22. Thus, valve support structure 24 may comprise three support posts for a tri-leaflet replacement valve 22. Support posts 32 of valve frame 24 may be structured to generally coincide with the natural commissures of the native valve being replaced.

Valve frame 24 may be formed from any suitable material including, but not limited to, stainless steel or nitinol. The particular material selected for valve support structure 24 may be determined based upon whether the support structure is self-expanding or non-self-expanding. For example, preferable materials for self-expanding support structures include shape memory materials, such as nitinol.

Figure 16:
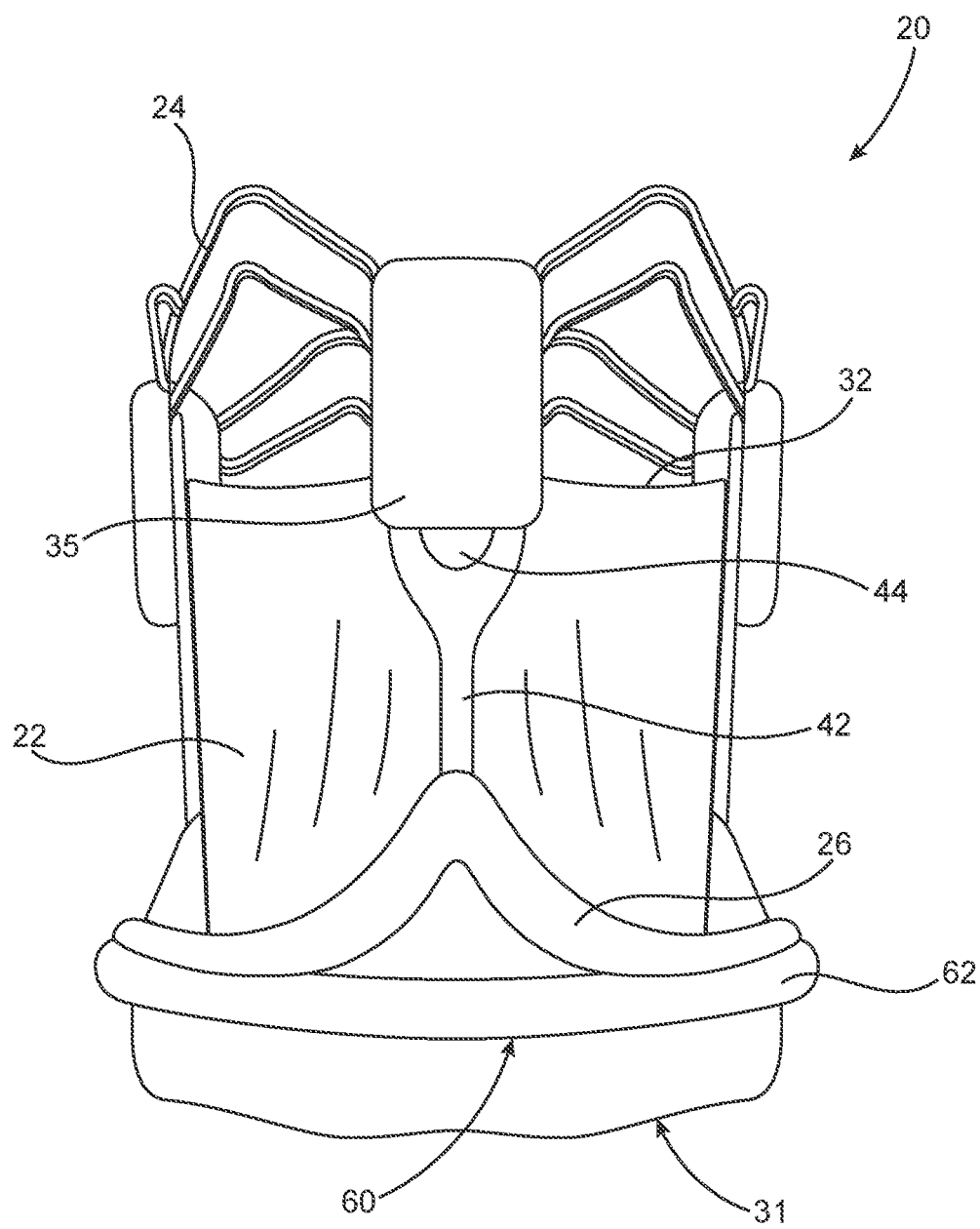
FIG. 16 is a schematic side view of the replacement valve system of FIG. 13.

FIG. 16 is a side view illustrating replacement valve device 20 of FIG. 13, which once again includes replacement valve 22, valve support frame 24, and valve cuff 26. As shown in the embodiment depicted in FIG. 16, valve 22 is secured at the proximal inflow end 31 by attachment to inflow rim 41 of valve frame 24 and at the distal outflow end 32 via commissural tabs 35 that are threaded through axially extending slots 44 formed in support posts 42. Notably, as can be seen in the embodiment shown in FIG. 16, outflow rim 43 of frame 24 is structured to be longitudinally displaced from the distal outflow end 32 of valve leaflets 33 that reside within the lumen of the tubular valve frame 24. Thus, contact between valve leaflets 33 and frame 24 is avoided.

The positioning of replacement valve 22 internally to frame 24 with only commissural mounting tabs 35 of replacement valve 22 contacting support posts 42 at the distal outflow end 32 of the valve, while the proximal inflow end 31 of the valve is separated from inflow rim 41 of valve support structure 24 by valve cuff 26, ensures that no part of replacement valve 22 is contacted by frame 24 during operation of valve 22, thereby eliminating wear on valve 22 that may be otherwise result from contact with mechanical elements.

As shown in FIG. 16, valve cuff 26 generally includes skirt 60 and flange 62. As illustrated in FIG. 16, skirt 60 may be structured to cover the outer surface of valve support structure 24, such as along the proximal inflow end 31. In particular, skirt 60 of valve cuff 26 wraps around the entire circumference of replacement valve 22 and frame 24 near the proximal inflow end 31 and inflow rim 41, respectively. Furthermore, as shown in FIG. 16, skirt 60 may have a generally scalloped configuration so as to substantially align with the scallops found in or around the native valve implantation site and with the scalloped configuration of replacement valve 22. However, one skilled in the art will appreciate that valve cuffs with non-scalloped skirts are also contemplated and within the intended scope of the present disclosure.

Skirt 60 of valve cuff 26 is designed to provide numerous benefits when used in conjunction with a replacement valve such as replacement valve 22. First, skirt 60 functions to protect the proximal inflow end 31 of replacement valve 22 from irregularities of a valve annulus such that, for example, calcification remnants or valve remnants left behind after a native valve removal procedure do not come into contact with any portion of replacement valve 22. If otherwise allowed to contact replacement valve 22, these remnants impose a risk of damage to the valve. Second, when positioned adjacent a native valve annulus, skirt 60 provides another source of valve sealing, and also assists valve cuff 26 to conform to irregularities of the native valve annulus. Third, once valve cuff 26 is positioned adjacent a native valve annulus, skirt 60 allows tissue ingrowth into the valve cuff. Such tissue ingrowth not only improves the seal provided by valve cuff 26, but also helps to anchor the valve cuff to the native valve annulus and minimize migration of replacement valve system 20 after implantation. Skirt 60 of valve cuff 26 may provide addition benefits other than those previously discussed as will be appreciated by those skilled in the art.

As illustrated in FIG. 16, flange 62 of valve cuff 26 is coupled to skirt 60 and is structured to protrude from replacement valve device 20 around the entire circumference of the valve. Once replacement valve system 20 is delivered to an implantation site and deployed, valve support structure 24 exerts a radial force within valve cuff 26 which pushes flange 62 against native tissue at the implantation site, thereby creating a seal to prevent paravalvular leakage and migration of replacement valve device 20 within the aorta. For example, in embodiments where valve support structure 24 is formed from a memory shaped metal, the radial force may result from the support structure "springing" back to expanded form after deployment at the implantation site.

Flange 62 of valve cuff 26 is structured for forming a seal between the proximal inflow end 31 of replacement valve 22 and the annulus of the native valve site. In some embodiments, if one or more native valve structures are removed from a patient's body prior to implantation of the replacement valve device 20, irregularities may exist around the annulus of the native valve site. These irregularities may be the result of, for example, natural calcifications or valve remnants left over from extraction of the native valve. Irregularities around the annulus can be problematic because they can contribute to paravalvular leakage.

In the past when irregularities were present, it was difficult to maintain a tight seal between the native valve annulus and the replacement valve. However, flange 62 of valve cuff 26 is structured to conform to irregularities around the native valve annulus, thus improving the seal between replacement valve 22 and the native valve annulus. As a result, paravalvular leakage around the replacement valve may be reduced or eliminated.

Figure 17:
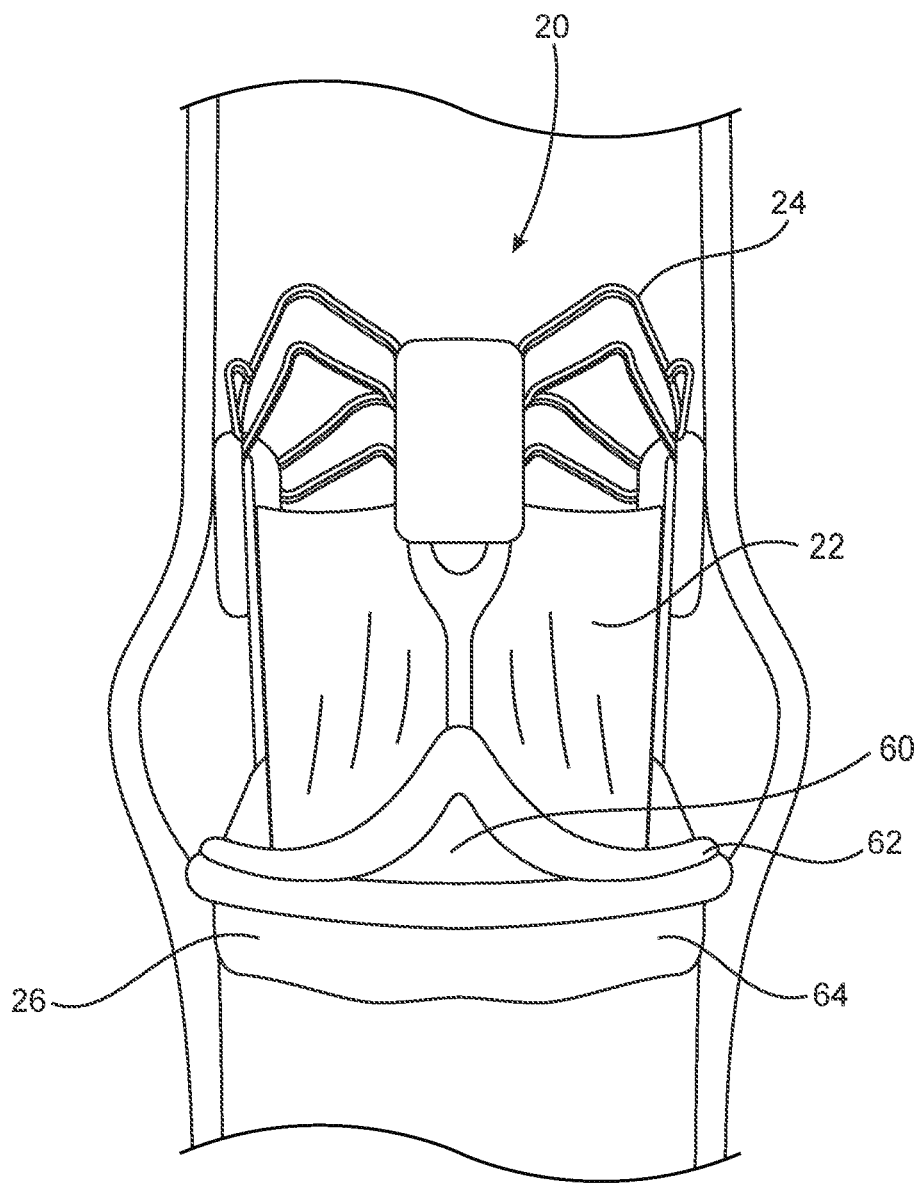
FIG. 17 is a schematic view of the replacement valve system of FIGS. 13 and 16 positioned within an aorta.

FIG. 17 is a view of replacement valve system 20 positioned within an aortic valve, which includes native valve annulus 64. As shown in FIG. 17, valve frame 24 has expanded within the native valve annulus 64, thereby forcing flange 62 of valve cuff 26 against native valve annulus 64 to form a tight seal between replacement valve 22 and the native valve annulus 64 so as to prevent or at least minimize paravalvular leakage and migration of replacement valve 22 from the implantation site. Thus, with flange 62 in contact with native annulus 64, valve cuff 26 acts as a gasket to seal the junction between replacement valve system 20 and the native valve annulus 64.

In one embodiment, an adhesive may be applied to valve cuff 26 prior to implantation within a native valve annulus. For example, any suitable biocompatible adhesive may be applied to the outer surfaces of skirt 60 and flange 62 to help seal valve cuff 26 to the surrounding tissue of the valve annulus. While not a necessary component, biocompatible adhesives may help to provide a tighter seal in order to further reduce paravalvular leakage.

In other embodiments, the flange 62 valve cuff 26 may be constructed with a memory shaped or deformable material disposed within the flange that helps to create a tight seal with the native valve annulus. In particular, the memory shaped or deformable material may be structured to expand once valve cuff 26 is properly positioned at the implantation site. This type of valve cuff flange may be utilized regardless of whether the valve support structure is of the self-expanding or non-self-expanding type.

In some embodiments, both skirt 60 and flange 62 of valve cuff 26 can be formed from a cloth or fabric material. The fabric may comprise any suitable material including, but not limited to, woven polyester such as polyethylene terepthalate, polytetrafluoroethylene (PTFE), or other biocompatible material.

In one exemplary embodiment of assembling valve replacement system 20, skirt 60 and flange 62 are formed as separate components that are coupled together in order to form valve cuff 26. In particular, skirt 60 may initially be positioned around and coupled to valve support frame 24 in any suitable manner, such as by suturing. For example, each skirt attachment portion 63 may be wrapped around a corresponding support post 42 of valve frame 24. Skirt attachment portions 63 may then, for example, be sutured to triangular shaped attachment sites 52 near the proximal ends 46 of each of the support posts 42. Then, flange 62 may be positioned at the desired position around skirt 60 and coupled to the skirt by any suitable means, such as by suturing. Next, replacement valve 22 may be positioned within the inner lumen of frame 24, inserting commissural tab portions 35 of replacement valve 22 through corresponding axially extending slots 44 in support posts 42. Skirt 60 of valve cuff 26, which is positioned circumferentially around inflow rim 41 of frame 24, may then be wrapped around the proximal inflow end 31 of replacement valve 22 and attached to the valve with, for example, sutures. Once attached, skirt 60 and flange 62 are structured to create tight, gasket-like sealing surfaces between replacement valve 22 and the native valve annulus. The foregoing represents only one exemplary embodiment of a method of assembling a valve replacement system in accordance with the present disclosure. Thus, modifications may be made to the number and order of steps as will be appreciate by one skilled in the art.

Figure 18A:
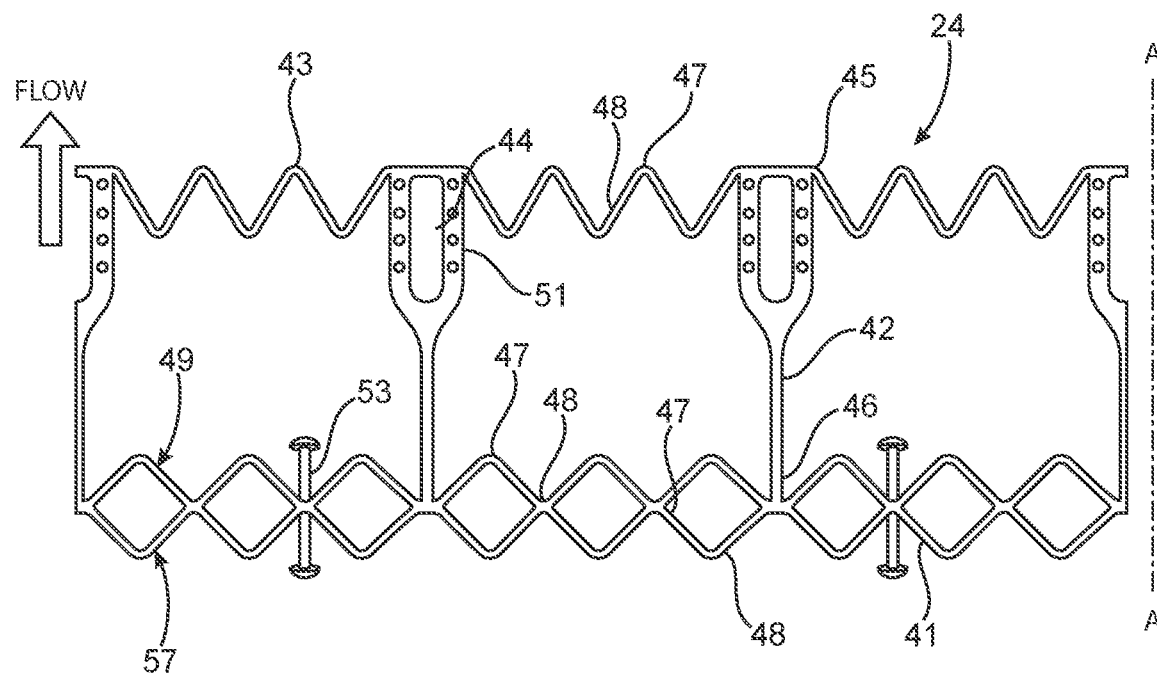
FIG. 18A is a schematic drawing of an embodiment of a support frame cut along line A-A and laid flat.

Referring now to FIG. 18A, a frame 24 of a prosthetic valve may include a concave landing zone, e.g., as described in U.S. Patent Application Publication No. 2010/0100176, entitled ANCHORING STRUCTURE WITH CONCAVE LANDING ZONE, which published patent application is hereby incorporated herein in its entirety to the extent that it does not conflict with the disclosure presented herein. The frame 24 in FIG. 18A is illustrated as cut along line A-A and laid flat. The frame 24 in FIG. 18A represents one exemplary embodiment of a typical anchoring or support structure useable with valve replacement system 20 described herein. In general, frame 24 is designed as a collapsible and expandable anchoring structure adapted to support a valve distally along commissural region and proximally along the proximal inflow end. As shown in FIG. 18A, valve has been detached from support frame 24 so as to focus on the structure and features of the support structure.

Frame 24 has a generally tubular configuration within which a replacement valve may be secured, and includes inflow rim 41, support posts 42 and outflow rim 43. A replacement valve may be secured at the proximal inflow end 31 by attachment to inflow rim 41 of support frame 24 and at the distal outflow end 32 via commissural tabs 35 that are threaded through axially extending slots 44, which are formed in support posts 42 that extend longitudinally from inflow rim 41 to outflow rim 43 of valve support structure 24. Thus, distal ends 45 of support posts 42 contact outflow rim 43 of valve support structure 24, whereas proximal ends 46 of support posts 42 contact inflow rim 41 of frame 24.

As shown in FIG. 18A outflow rim 43 of support frame 24 is depicted as comprising a single wire ring or rail that extends between support posts 42 generally at or above the axially extending slots 44 that reside therein. The outflow rim 43 is configured in an undulating or sinusoidal wave pattern forming peaks 47 and troughs 48. However, the number of rings is not important, and numerous other configurations are contemplated and may be utilized such as single, double and triple configurations of varying patterns. Inflow rim 41 is depicted as comprising a double wire ring or rail that includes a distal inflow wire ring 49 and a proximal inflow wire ring 51. Distal inflow wire ring 49 and proximal inflow wire ring 51 are configured in an undulating or sinusoidal wave pattern forming peaks 47 and troughs 48. As can be seen, the double wire rail is configured so that a peak of proximal inflow wire ring 51 connects with a trough of distal inflow wire ring 51 thus forming a diamond pattern although any number of desired shapes may be achieved such as pentagonal, hexagonal, rectangular, etc., all of which are within the scope of the disclosure presented herein.

The inflow rim 41 optionally includes finger-like elements 53 positioned at which distal and proximal inflow wire rings 49, 51 connect and extend in an axial direction therefrom. Finger-like elements 53 are designed to lend additional support to fabric that may cover inflow rim 41 to anchor the fabric and permit tissue ingrowth.

In the embodiment of support frame 24 illustrated in FIG. 18A, outflow rim 43 is formed with a single ring, while inflow rim 41 is formed with a double ring that extends between support posts 42. However, the number of rings may vary, and numerous other configurations are contemplated.

Both inflow rim 41 and outflow rim 43 of frame 24 may be formed with an undulating or sinusoidal wave-like configurations. In various embodiments of valve support structures, inflow rim 41 may have a shorter or longer wavelength (i.e., circumferential dimension from peak to peak) or a lesser or greater wave height (i.e., axial dimension from peak to peak) than outflow rim 43. The wavelengths and wave heights of inflow rim 41 and outflow rim 43 may be selected to ensure uniform compression and expansion of support frame 24 without substantial distortion. The wavelength of inflow rim 41 may be further selected to support the geometry of the inflow end of the valve attached thereto, such as the scalloped inflow end 31 of replacement valve 22 shown in FIG. 18. Notably, as shown in FIG. 18A, the undulating or sinusoidal wave pattern that forms inflow rim 41 of frame 24 may be configured such that proximal ends 46 of vertical support posts 42 are connected to troughs 48 of inflow rim 41. Similarly, the undulating or sinusoidal wave-like pattern that forms outflow rim 43 of support structure 24 may be configured such that distal ends 45 of support posts 42 are connected at a peak 47 of outflow rim 43. This arrangement allows the distal inflow wire ring and proximal inflow wire ring to move together when the valve is in its radially compressed state prior to delivery thus preventing possible damage to the bioprosthetic heart valve.

In the embodiment depicted in FIG. 18A the distal ends 45 of support posts 42 are configured generally in the shape of a paddle with axial slot 44 extending internally within blade 51 of the paddle. Blade 51 of the paddle is oriented toward outflow rim 43 of support structure 24 and connects to outflow rim 43 at a peak of the undulating sinusoidal wave-like pattern of outflow rim 43. Support posts 42 stabilize a valve in general, and in particular the prevention of longitudinal extension at points of valve attachment to preclude valve stretching or distortion upon compression of replacement valve system. Blades 51 of the paddle-shaped support posts 42 are also designed to accommodate commissural tabs of a valve.

The number of support posts 42, if present, generally ranges from two to four, depending on the number of commissural posts present in the valve sinus. Thus, in some embodiments, valve support structure 24 comprises three support posts for a tri-leaflet replacement valve with a native valve that features three natural commissures. Support posts 42, if present, of frame 24 may be structured to generally coincide with the natural commissures of a native valve.

Figure 18B:
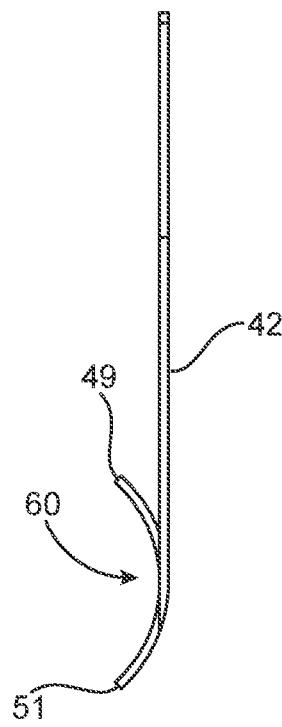
FIG. 18B is a schematic drawing of a cross-sectional view illustrating the concave landing zone of the frame of FIG. 18A.

Turning now to FIG. 18B a cross-sectional view of the inflow rim 41 is depicted which illustrates the concave landing zone 60. As can be seen, peaks 47 of the distal inflow ring 49 and troughs 48 of the proximal inflow ring 51 flare outwardly so that inflow rim 41 forms a C-shape in cross section upon deployment. This cross-sectional area 61 of the inflow rim 41, or in other words the concave portion of the frame, directly corresponds to the native annulus. The frame of the inflow rim engages the native annulus, with the flared rails 47, 48 lying above and below the annulus. Upon deployment, the radial force exerted by the self-expanding frame holds the valve in position.

The concave landing zone 61 substantially prevents paravalvular leakage. Paravalvular leakage may be reduced by ensuring the inflow rim 41 is substantially secured proximally and distally of the annulus, hence forming a tight seal. Concave landing zone 60 allows the surgeon to easily place the bioprosthetic heart valve in the annulus thus minimizing patient time spent in surgery.

Figure 19:
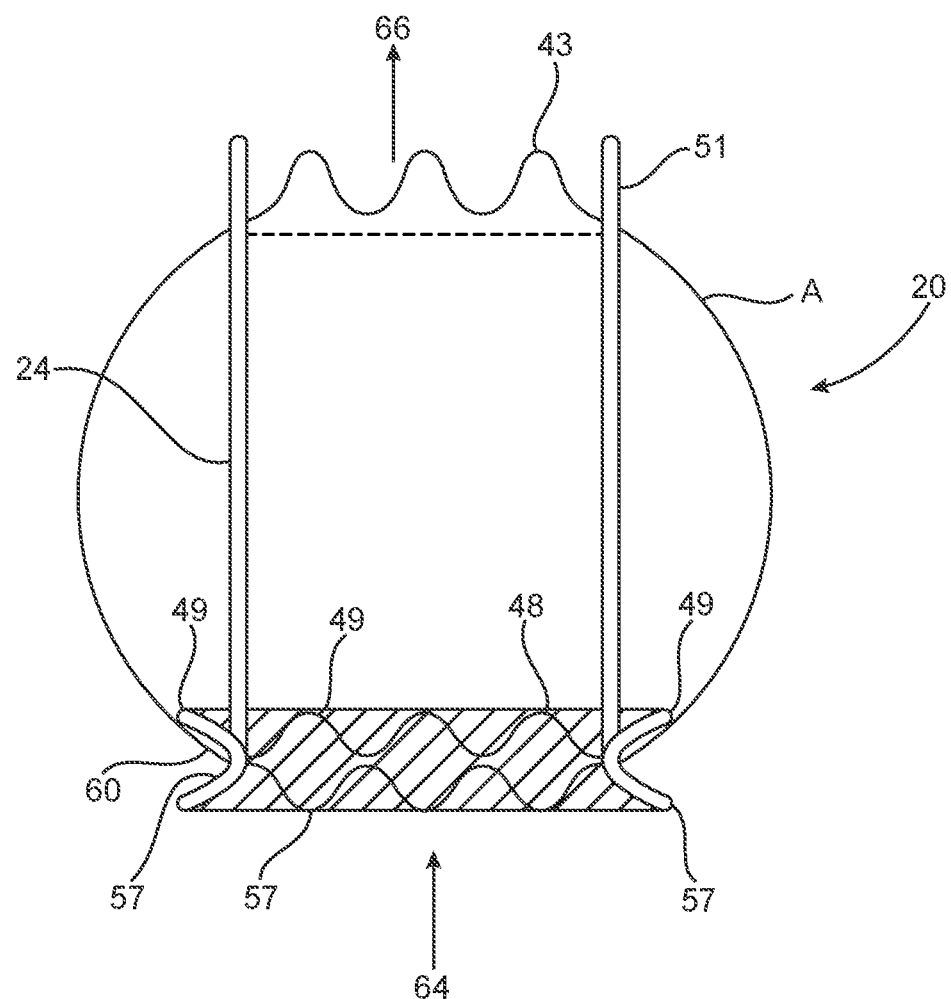
FIG. 19 is a schematic drawing of an embodiment of a valve replacement system positioned in an aorta.

FIG. 19 is a view of replacement valve system 20 positioned within a native valve anatomical structure, which includes inflow annulus 64 and outflow annulus 66. As shown in FIG. 10, the tubular anchoring structure 24 of FIG. 18A has expanded within the sinus cavities of native valve location, thereby forcing inflow rim 41 against inflow annulus 64 of the native valve anatomy to form a tight seal between replacement valve system 20 and native valve anatomy. More specifically, upon deployment inflow rim 41 assumes a substantially C-shaped in cross section concave landing zone 60 as can be seen in FIGS. 18B and 10. Distal inflow ring 49 abuts the distal side of the annulus while proximal inflow ring 51 abuts the proximal side of the native annulus. The concave landing zone 60 prevents or minimizes paravalvular leakage and migration of replacement valve system 20 from the implantation site. Thus, with inflow ring 41 in contact with inflow annulus 64, the concave landing zone 60 acts as a gasket to seal the junction between replacement valve system 20 and native anatomy. Typically, inflow ring 41 is covered with fabric to stimulate tissue ingrowth over time and secure the replacement heart valve in position. The fabric may comprise any suitable material including, but not limited to, woven polyester, polyester velour, polyethylene terephthalate, polytetrafluoroethylene (PTFE), or other biocompatible material. The valve assembly may be compressed in ice, loaded into a delivery system, and deployed into the aortic valve position. The self-expanding characteristic of the anchoring structure provides the radial strength required to hold the valve in position after implant.

Although the above disclosure focused on a tri-leaflet replacement valve device 20, valve cuffs in accordance with the present disclosure may be used in conjunction with any type of replacement valve of generally similar structure, including but not limited to the heart valves disclosed in U.S. application Ser. No. 10/680,071, U.S. application Ser. No. 11/471,092, and U.S. application Ser. No. 11/489,663, all incorporated herein in their entirety to the extent that they do no conflict with the disclosure presented herein. Therefore, the valve cuff concepts disclosed herein may be applied to valve cuffs structured to function with many other types of replacement valves having any number of leaflets without departing from the spirit and scope of the present disclosure.

Furthermore, although the above disclosure focuses on frame 24 having an inflow rim 41, an outflow rim 43, and three support posts 42, this particular valve support structure was described merely for purposes of example and not limitation. Thus, valve cuffs in accordance with the present disclosure may be used in conjunction with any generally tubular, stent-like valve support structure, as will be appreciated by one skilled in the art.

Additional designs of prosthetic heart valves that may be employed with the delivery systems and associated devices described herein include those designs disclosed in U.S. Provisional Patent Application No. 61/819,486 filed on May 3, 2013, and those disclosed in U.S. patent application Ser. No. 14/268,494, now U.S. Pat. No. 9,375,311, entitled PROSTHETIC VALVES AND ASSOCIATED APPARATUSES, SYSTEMS AND METHODS, filed on the same day as the present application, which patent applications are each hereby incorporated herein by reference in their respective entireties to the extent that they do not conflict with the disclosure presented herein. Heart valves may have markings to facilitate implant and provide visual feedback regarding implant depth or orientation such as described in, for example, (i) U.S. Provisional Patent Application No. 61/930,851, filed on Jan. 23, 2014; (ii) U.S. Provisional Patent Application No. 61/819,486 filed on May 3, 2013; and (iii) U.S. patent application Ser. No. 14/268,303, entitled MEDICAL DEVICES FOR IMPLANTING IN A VALVE AND ASSOCIATED METHODS, filed on the same day as the present application, each of which patent applications are hereby incorporated herein by reference in their respective entireties to the extent that they do not conflict with the disclosure presented herein In embodiments, replacement valve systems described herein are sutureless valve systems. Of course, sutures may be used with such systems. Advantages to sutureless replacement valve systems include shorter implant procedure times and less invasive implantation. Some disadvantages or perceived disadvantages with current sutureless valve systems include potential increased risk of paravalvular leakage (PVL) and potential lack of durability. The designs presented herein preferably address one or more of the disadvantages or perceived disadvantages of current sutureless valve designs.

III. Systems and Devices for Retention or Delivery of Prosthetic Heart Valves

Various embodiments of a holder and delivery system for a valve replacement system are described below. In some embodiments, the holders and delivery systems provide a solution to inaccurate placement or insufficient visibility often associated with valve delivery systems, particularly delivery systems for delivering sutureless prosthetic valves.

Of importance to the implantation process is the valve replacement system and delivery system packing configurations. In some embodiments, the valve is packaged with a holder, one or more cords (which may include cinch sutures forming loops and tethers), and an adapter to manage the cords and to prevent tangling. In some embodiments, the delivery system is packaged separately with a crimping funnel and any other accessories.

In FIGS. 20-42 and 53-74 below, a number of embodiments of heart valves, holders and delivery systems are described. In many aspects the components presented in, or discussed with regard to, FIGS. 20-42 and 53-74 are similar to those presented in, or discussed above with regard to, FIGS. 1-9, with like numbers referring to similar components. Use of different numbers in the figures does not necessarily mean that the labeled systems, devices, or components are dissimilar or cannot be the same.

Figure 20B:
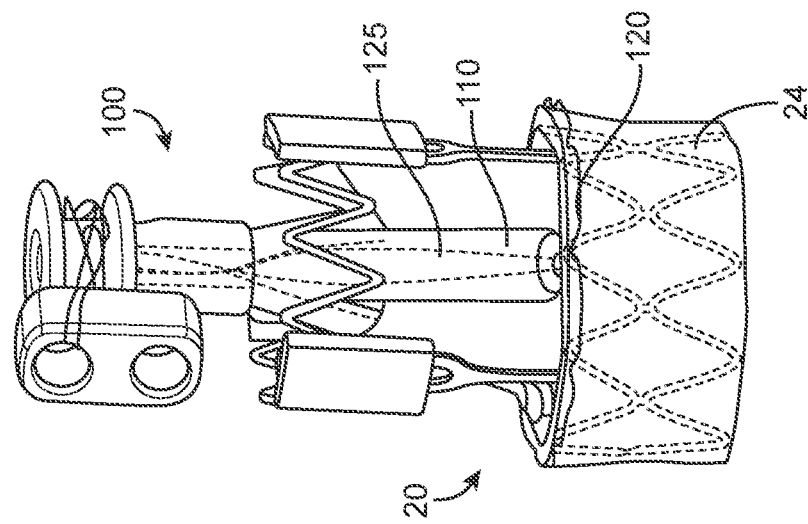
FIGS. 20A-B are schematic drawings of side views of an embodiment of a holder and prosthetic valve, where the prosthetic valve is in an expanded configuration (20A) and a constricted configuration (20B).
Figure 20A:
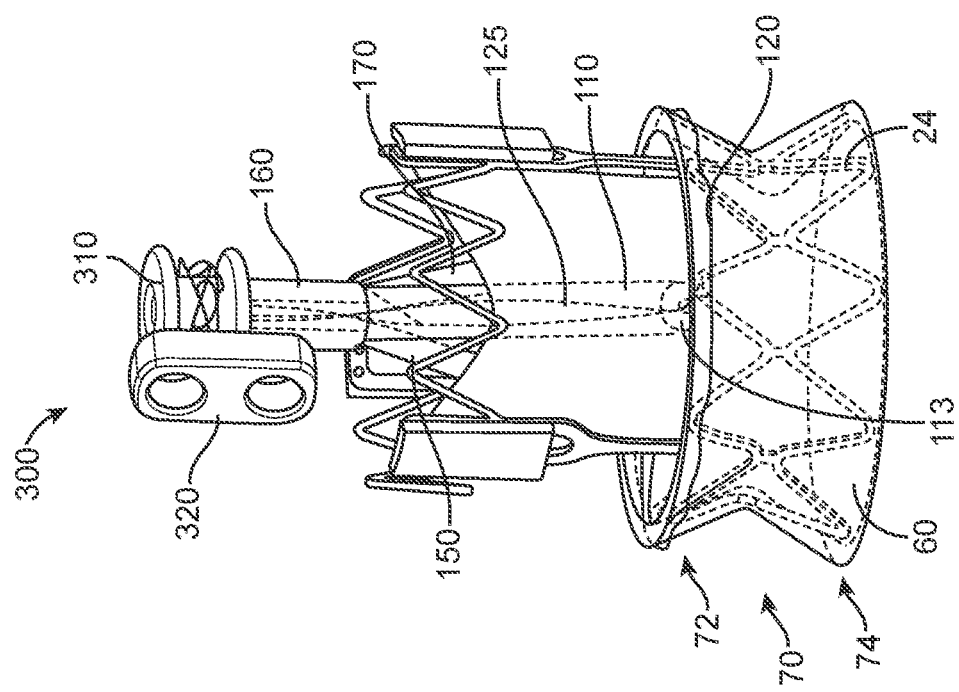

Referring now to FIGS. 20A-B, an embodiment of a holder 100 and a prosthetic heart valve 20 having a self-expanding frame 24 is shown. In the depicted embodiment, the holder has three extensions 110, 150, 170 that extend from adapter 160 into a central opening of the device 20. At the distal end portions of the extensions, conduits (e.g., conduit 113 of extension 110) are formed through the extensions for management of cords (e.g., cord 125). In the depicted embodiment, there is one cord for each extension. While not readily apparent from the drawings, each cord (e.g., cord 125) is disposed around about one-third of the circumference of an upper portion 72 of the inflow region 70 of the prosthetic heart valve device 20. Together, the three cords extend substantially around the upper portion 72 of the inflow region 70. In such embodiments, all of the cords are preferably dependently controlled such that the loops (e.g., loop 120 of first cord 125) are constricted or expanded together via tension. While not depicted, it will be understood that a single loop may extend around the upper inflow portion 72 or that other loops may extend around at least a portion of other regions such as the lower portion 74 of the inflow region 70 or an outflow portion of the device or frame.

In some embodiments, a cord positioned around an inflow region of a prosthetic valve may pass through a skirt one or more times. Passing a cord through the skirt may result in undesirable puckering of the skirt. With smaller bites (passing in and out of the skirt at shorter intervals) results in less puckering. In various embodiments, a cord passes in and out of a skirt at an interval of 2 mm or less. Preferably, the bites occur at locations of flared structures of the frame to prevent the cord from sliding down when the valve is warmed.

In some embodiments, a cord is positioned around an outflow portion of a prosthetic valve in a manner such that the cord does not slide off of the top of the valve. In some embodiments, the cord is passed through one or more fabric pieces that are assembled to the valve outflow region (e.g., at the commissures). In some embodiments, hooks or flared portions are formed into the outflow end of the frame to capture the cord.

In FIG. 20A, the device 20 is shown in an expanded configuration. As shown the inflow region 70 is concave when the frame 24 is expanded with the upper 74 and lower 72 portions of the inflow region 70 forming flanges configured to engage and help seal (along with skirt 60) the device about an annulus of a valve sinus. In FIG. 20B the device is shown in a constricted configuration.

A cord management assembly 300 is also depicted in FIGS. 20A-B. The cord management system 300 includes a spool 310 around which the cords are wrapped and a block 320 to which the cords may be attached.

Nearly any embodiment described herein can include a cord management assembly, such as the assembly depicted in FIGS. 20A and 20B. Inclusion of a cord management assembly can serve to manage cords during shipping and/or crimping prior to connecting the holder to the delivery system. In embodiments, the tether management component comprises a coil around which the tether sutures are wound and to which the tether connection adapter is mounted. This may allow for the prosthetic valve to be crimped without the user managing a bird's nest of cords. The cord management assembly may, in some embodiments, be discarded when the prosthetic valve is ready to be connected to the delivery system.

Referring now to FIGS. 21A-D, an embodiment of a holder 100, prosthetic heart valve 20 and delivery system (or portions thereof) are shown at various stages of an implant procedure. The holder 100 and prosthetic heart valve 20 are the same as depicted in FIGS. 20A-B, with like numbers referring to like components.

Figure 21A:
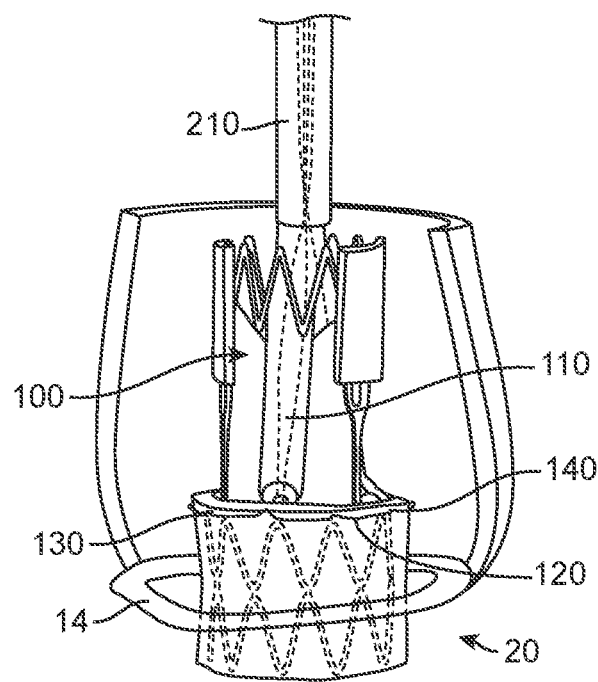
FIGS. 21A-D are schematic side views showing a some steps of an embodiment of a procedure for implanting an embodiment of a prosthetic valve with an embodiment of a holder in a valve sinus of a patient.

As shown in FIG. 21A, a shaft 210 of a delivery system is coupled to the adaptor of the holder 100. The prosthetic heart valve device 20 is inserted into a native valve until an appropriate portion of the inflow region of the device 20 is aligned with the annulus 14 of the native valve via holder 100 and delivery system. The valve device 20 is inserted in a constricted (e.g., crimped) configuration. Tension is placed on cords forming loops 120, 130, 140 to retain the upper inflow portion 74 in a constricted configuration.

Figure 21B:
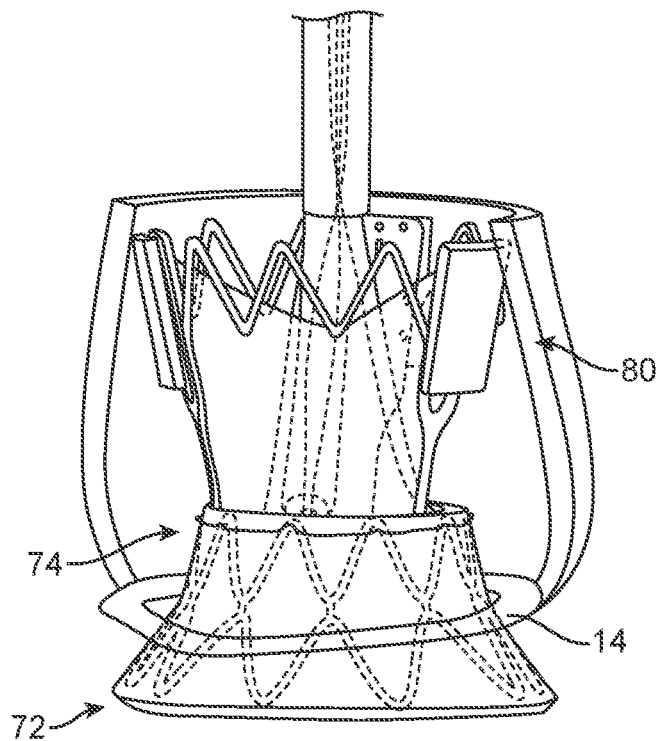
Figure 21C:
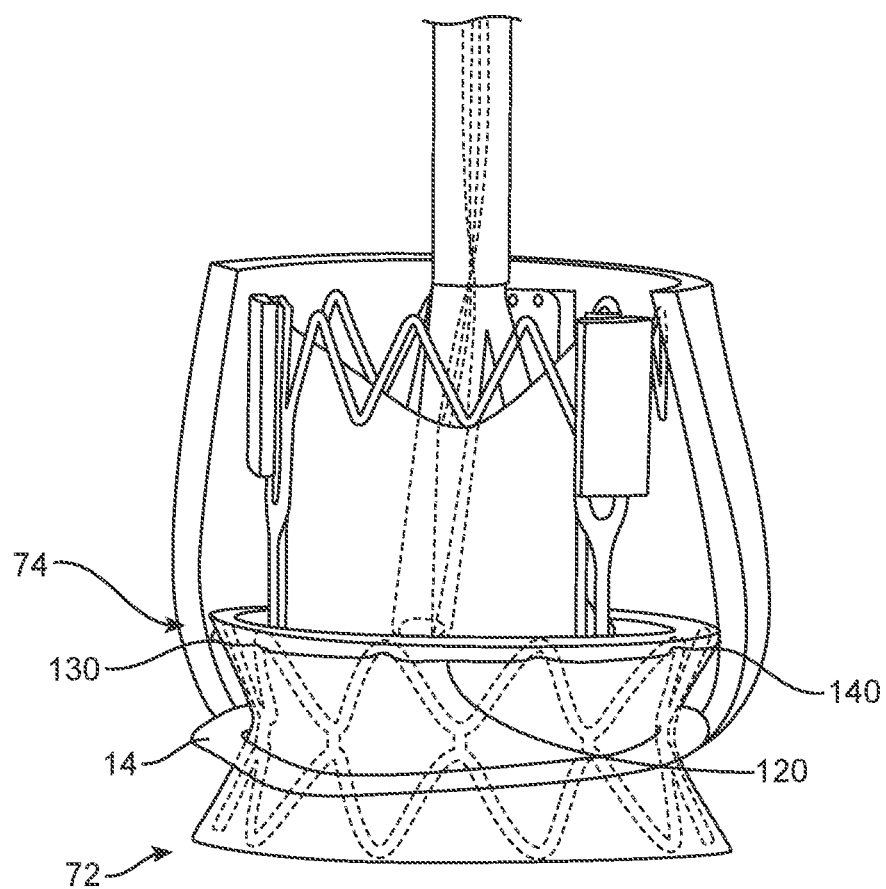
Figure 21D:
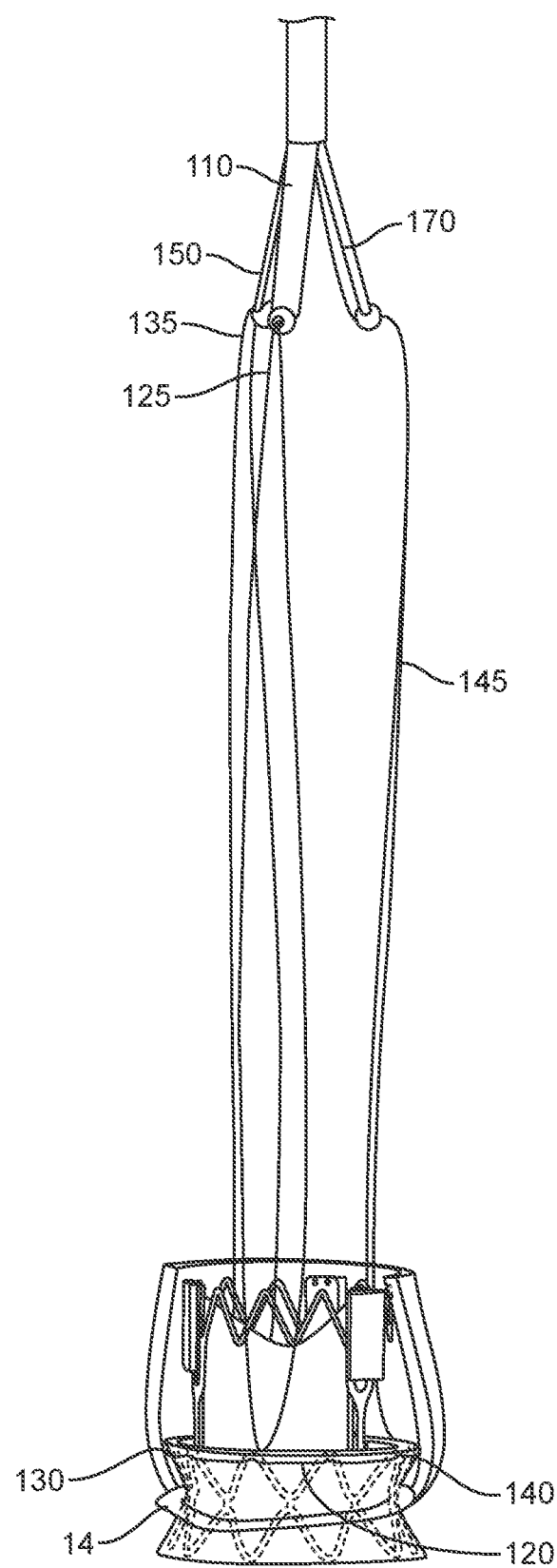

As shown in FIG. 21B, while tension is retained on cords forming loops to constrict upper inflow portion 74 other portions (e.g., lower portion 72 of inflow region and outflow region 80) are expanded or allowed to expand. In some embodiments, the frame is expanded by heating the frame; e.g., with warm water or saline. If the device 20 is inserted to an appropriate depth, expansion of the lower portion 72 of the inflow region should prevent withdrawal of the device 20 past the annulus 14. If the device 20 appears to be properly positioned or is moved to be properly positioned after expansion of the lower portion 72 of the inflow region, the upper portion 74 of the inflow region may be allowed to expand by loosening tension of the cords to allow the loops 120, 130, 140, and thus the upper inflow portion 74, to expand (FIG. 21C). With expansion of upper inflow portion 74 and lower inflow portion 72, the device 20 securely engages the native valve annulus. With the upper inflow portion 74 expanded, the holder, or a portion thereof, (e.g., the extensions 110, 150, 170 and adaptor are removed over the cords 125, 135, 145 as depicted in FIG. 21D) may be removed from the surgical zone while the loops 120, 130, 140 remain loosely around the frame so that proper positioning of the prosthetic heart valve can be confirmed. If the positioning is confirmed, the cords 125, 135, 145 may be cut and the cords (and loops) removed. If the prosthetic heart valve is determined to be improperly positioned, the delivery tool and holder may be advanced over the cords towards the prosthetic valve and the upper inflow region may be constricted by increasing tension on the cords to restrict the upper inflow portion, and the prosthetic valve may be repositioned as needed or desired.

A cord that forms a loop for retaining the prosthetic valve in a constricted configuration may be made of any suitable material and may engage the prosthetic valve in any suitable manner. In embodiments, the cords are formed from surgical suture material. The cords, among other things, can function to crimp the valve upper inflow cuff, hold the valve firmly to the holder when tensioned, and/or maintain a tether with the valve even after the holder or delivery system have been removed from the surgical cavity. A cord may be one long suture routed through the valve in one or more (e.g., three) instances; one or more (e.g., three) sutures routed through the valve once each; or a combination thereof. As a result of either condition, there are multiple (e.g., six) suture arms that exit the valve. In the case of three sutures, each tether suture can encapsulate ⅓, ⅔, 360° or more of the valve circumference. In such cases, all of the functions of the tether can be achieved with ⅓rd circumferential encapsulation. Accordingly, it may be desirable to limit each suture to ⅓rd encapsulation as additional encapsulation may lead to greater suture removal forces at the end of the procedure. High tether suture removal forces can lead to valve dislodgement. Accordingly, in some embodiments, small diameter sutures with high strength may be preferred [(e.g., 3-0 ultra-high molecular weight polyethylene (UHMWPE)]. Of course other sutures (e.g., 2-0 Polypropylene, 2-0 Nylon, 4-0 UHMWPE, or the like) or other suitable material may be used. The loops may be routed through the lower inflow cuff, central inflow cuff, the outflow rail & tabs, or combinations thereof.

Figure 22A:
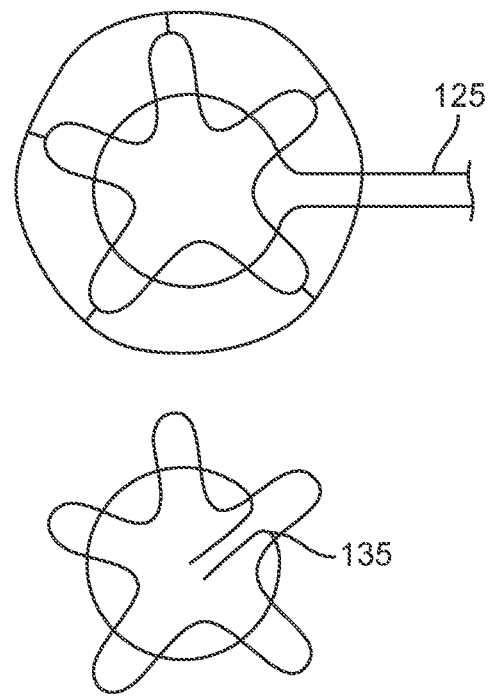
FIGS. 22A-B are schematic top views of embodiments of suture styles for looping one or more cords around at least a portion of a prosthetic valve.
Figure 22B:
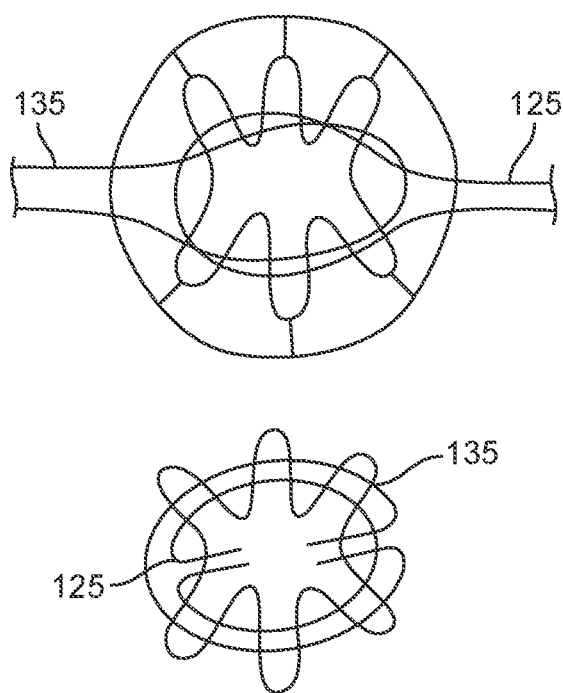
Figure 23:
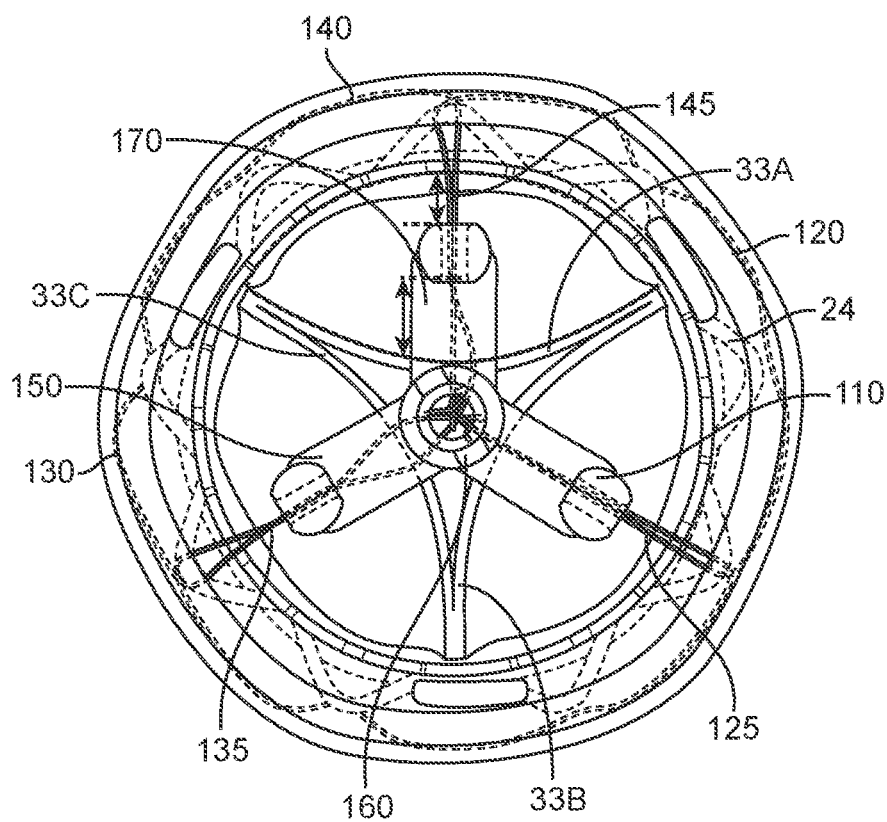
FIG. 23 is a schematic bottom view of an embodiment of a holder positioned relative to an embodiment of a prosthetic valve.

A version using two cords 125, 135 to surround a periphery of a prosthetic heart valve frame portion is shown in FIGS. 22A-B. The cords may be of different color (e.g., blue and red). The cords may be configured in an asymmetric gathering manner, such as a purse string manner (FIG. 22A), a symmetric gathering manner, such as a superior purse string manner (FIG. 22B), or any other suitable manner.

Regardless of the number of cords or suture style, the holder may include one or more extensions forming one or more conduits for the cords. The conduits may run the length of the extension or through only a portion of the extension. For example, as shown in the embodiment depicted in FIGS. 20-21, a conduit may be formed at a distal end portion of an extension. The conduits may route one, two, or more arms of a cord, depending on the style of the loop. In the embodiment depicted in FIGS. 20-21, each of the three extensions routes two arms of the cord to each of the three lobes of the prosthetic valve. In the embodiments depicted in FIGS. 20-21, the three extensions (110, 150, 170) are preferably separated at 120° each.

In such embodiments, the extentions preferably flare out enough to clear leaflets of the prosthetic valve upon holder removal or reinsertion from the valve, but not flare out so much that they snag on the outflow rail. An illustration is provided in FIG. 23, where two arms of a first cord 125 in inserted through a distal conduit of a first extension 110, two arms of a second cord 135 in inserted through a distal conduit of a second extension 150, and two arms of a third cord 145 in inserted through a distal conduit of a third extension 170. In the embodiment depicted in FIG. 23, the extensions are separated at 120° and are inserted into valve in an orientation to avoid contact with the three valve leaflets 33A, 33B, 33C. In the embodiment depicted in FIG. 23, each of loops 120, 130, 140 of the cords extends about 120° around an upper inflow portion of frame 24 of the prosthetic valve. In addition, the depicted embodiments shown each of the cords extending through a single lumen of adaptor 160.

Figure 24:
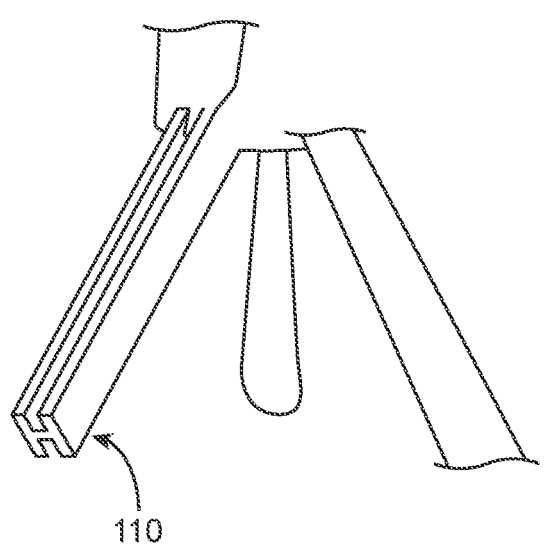
FIG. 24 is a schematic side view drawing illustrating an embodiment of an extension of a holder.

Preferably holder extensions are sufficiently rigid to cumulatively support crimping loads of 25-30 lbs. Having the extensions take a tubular shape or I-beam geometry helps to prevent deflection of the extensions. The holder may also function to provide a rigid connection between the prosthetic valve device and the delivery system when the loops are tensioned, which allows for repositioning of the prosthetic valve by twisting or adjusting the vertical positioning of the delivery system. The legs could be metal, plastic, or any other material that is rigid or semi-rigid. An illustration of an I-beam holder extension 110 is depicted in FIG. 24. I-beam geometry should better resist torsional forces.

Figure 25:
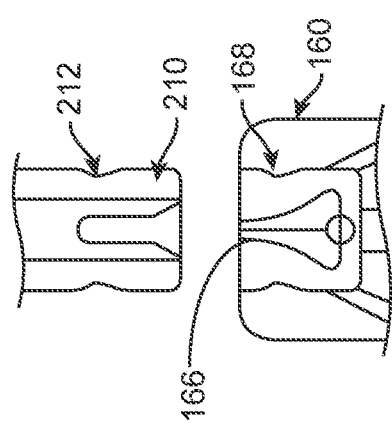
FIG. 25 is a schematic sectional view of an embodiment of a shaft of a delivery system and an embodiment of an adaptor of a holder.

In order to adjust the positioning of the prosthetic valve via the holder, the holder is preferably rigidly attached to the delivery system shaft. The connection with the holder to the shaft preferably resists both axial and torsional forces at the same time. One example of a holder-shaft connection is depicted in FIG. 25 in which snaps or indents 168 of adaptor 160 of holder cooperate with detents 212 of shaft 210 of delivery system. The adaptor 160 and shaft 210 may include an auto aligning key 168 for rotational stability. Of course any other suitable holder-shaft connection may be employed, such as other snap fits with detents, bayonets, threaded connections, ball bearing airline fitting, shoe horn connections requiring connection then 90° rotations, and the like. Some examples of such connections are shown in FIGS. A9-A12 of U.S. Patent Provisional Application No. 61/819,488, entitled SURGICAL HEART VALVES AND ASSOCIATED APPARATUSES, SYSTEMS AND METHODS, filed on May 3, 2013, which as indicated above is incorporated herein by reference to the extent that it does not conflict with the disclosure presented herein.

Additional Description

Provided below is additional discussion of tripod holder and ratcheting delivery system embodiments. Some embodiments presented below may the same as or similar to those described above.

The embodiments of holders and delivery systems described in this section, among other things, provide a solution to inaccurate placement and insufficient visibility with sutureless valve delivery systems.

Preferably, the prosthetic valve would come packaged with a holder. The surgeon would first size the native valve annulus and then choose the proper valve with holder. The holder/valve would then be removed from their packaging and placed in an ice bath. The holder/valve would then be coupled or connected to the delivery system shaft. The valve would then be crimped using either a disposable crimper or the built-in sutures. The crimped valve would then be lowered into a patient to the level of the native valve annulus to be replaced and warm saline would be sprayed on the valve. The prosthetic valve would be rotated so the tabs align with the native leaflet commissures and the ratchet on the handle would be actuated in the deployment mode. Following prosthetic valve expansion, if the positioning were not right, the surgeon would switch the ratchet to crimp mode and the valve would be crimped and repositioned. After the repositioning is complete, the valve would be ratcheted out again in deployment mode and the positioning would be confirmed. To remove the holder from the prosthetic valve, a button would be depressed on the handle to sever the sutures. The handle with holder would be removed from the patient. The three suture remnants would then individually be plucked from the prosthetic valve to complete the implantation.

Inaccurate placement is accounted for by having a three pronged holder fixed to the valve by three removable sutures. The holder allows for easy rotation and repositioning of the prosthetic valve in the native valve annulus through its rigid attachment at three locations. The attachment locations could be on the upper inflow cuff on the outside of the leaflets and/or on the lower inflow cuff with the three prongs going through the inner orifice of the leaflets. The three sutures affixed to the prosthetic valve can be used to reduce the valve diameter through pulling them tight with a ratcheting mechanism in the handle. The prosthetic valve may be deployed by warming the valve and releasing the tension on the sutures (reverse ratcheting). If one wanted to control both the upper and lower inflow, an additional suture could be lassoed through the end of the inflow opposite the holder. By having three sutures crimp the valve at 120 degrees, uniform reduction of the valve has been demonstrated. A cutting mechanism in the handle may be used to sever the sutures and allow for them to be pulled out after deployment.

Because this embodiment uses just three small tubes to attach to the valve, visibility of the inflow cuff and anatomy is unencumbered by any bulky cones or other delivery tool components. Confirmation that the prosthetic valve is seated on the native valve annulus may be achieved by simply ratcheting the upper inflow of the prosthetic valve in until the native valve annulus is seen.

The handle mechanism may have a single pushbutton that actuates a gear which retracts the three sutures linearly. Achieving this linear travel could be achieved by spooling a wire around the gear, using a worm-gear to translate the rotational to linear travel, or simply using linkages to achieve the desired linear travel. The pushbutton could be in the surgeon's dominant hand or could be attached to the handle by a tether, which could then be operated by the surgeon's non-dominant hand or an assistant. Alternative to a purely mechanical suture tightening mechanism, a servo motor could be used to tighten and loosen the sutures. The advantage of using a motor is that the surgeon would have greater stability while operating the tool (similar to the difference in performance of using a hand cranked drill which requires two hands for stability vs a hand held power drill which can easily be operated with one hand). In any case, this embodiment assumes the valve crimping mechanism can be both ratcheted in two directions, crimp and deployment modes. A prawl or pulley mechanism may be used to prevent backwards motion. Crimp and deployment modes could be achieved either through two ratchet buttons or through one button with a crimp/deployment switch. Alternatively, a threaded handle could be used.

The following are deployment steps that may be performed (post-sizing): (1) Rinse Valve; (2) Chill Valve; (3) Transfer Valve/Holder to Disposable Crimper; (4) Crimp Valve with Disposable Crimper; (5) Attach Valve/Holder to Delivery Tool Shaft; (6) Actuate crimping ratchet to tighten Holder; (7) Remove Valve from Crimper; (8) Remove Disk from Holder; (9) Position Valve within Annulus; (10) Warm Valve w/warm saline; (11) Unratchet Valve into position; (12) Reratchet and reposition/redeploy as necessary; (13) Actuate Holder Removal Button to sever three gathering Sutures and unlock flexible rear Shaft; (14) Pull flexible rear Shaft from back of Delivery Tool to remove gathering Sutures; and (15) Remove Delivery Tool/Holder.

Other Embodiments

Versions of holders other than the tripod are contemplated, including one that attaches to the outflow rail or tabs using many extensions and another that cinches the outflow rail and tabs with a plastic sleeve or band. Examples are shown in FIGS. A16-A17 of U.S. Patent Provisional Application No. 61/819,488, entitled SURGICAL HEART VALVES AND ASSOCIATED APPARATUSES, SYSTEMS AND METHODS, filed on May 3, 2013, which as indicated above is incorporated herein by reference to the extent that it does not conflict with the disclosure presented herein.

Implant Process

For purposes of example, a procedure will now be described for implanting a prosthetic valve device, such as Medtronic, Inc.'s Enable II valve, that may be used employing a variety of embodiments of a holder and delivery system described herein. Following removal of the patient's native leaflets and debridement of the native annulus, a surgeon typically sizes the native annulus and selects the proper replacement valve system. The replacement valve system with holder and cord are then removed from their packaging and placed in an ice bath. The holder/valve are then typically coupled or connected to a delivery system shaft. The prosthetic valve would then be crimped using either a disposable crimper or built in sutures. Alternatively, the prosthetic valve could be crimped prior to attachment to the delivery system. The crimped prosthetic valve would then be positioned within a patient and lowered to the level of the native valve annulus and warm saline would be sprayed on the prosthetic valve. The upper inflow of the prosthetic valve would remain crimped due to circumferential loops that are under tension. The prosthetic valve would be rotated so the tabs align with the native leaflet commissures and a delivery system actuation element would be actuated to release tension on the loops. The surgeon would then slide the delivery system and holder out of the surgical cavity to check positioning of the prosthetic valve. If the positioning were not right, the surgeon would slide the delivery system back to the prosthetic valve, actuating an actuation element on the delivery system, and the prosthetic valve would be crimped via the tensioned loops and could be repositioned. After the repositioning is complete, the prosthetic valve would be deployed again via the deployment system and the positioning would be confirmed. To complete the prosthetic valve deployment process, cords would be cut when the delivery system is pulled out of the surgical cavity. The suture remnants (typically three) would then individually be plucked from the prosthetic valve to complete the implantation.

If initial deployment of the prosthetic valve is above the native valve annulus, re-tensioning of loops around the upper inflow portion of the prosthetic valve frame will only reduce the upper inflow cuff and therefore won't allow for the expanded lower inflow cuff to pass below the native valve annulus. Accordingly, one or more loops may be positioned around the lower portion of the inflow cuff or the prosthetic valve may be removed from the surgical cavity and recrimped. To recrimp the prosthetic valve, first the prosthetic valve may be warmed to return it to its native shape if the frame, or components thereof, is formed from, for example, shape memory material such as Nitinol. Next the prosthetic valve may be chilled and a funnel, such as a clamshell funnel, may be placed on the delivery system shaft proximal to the prosthetic valve. A guide may be used to guide the prosthetic valve through the funnel, crimping the entire prosthetic valve. The clamshell funnel may be opened, the prosthetic valve may be removed from the prosthetic valve guide, and any residual cord slack may be collected by actuating an actuation element.

Delivery System Tether Engagement Methods

In some embodiments, a delivery system performs at least three functions. First, it is able to connect with the adaptor and cords of a holder. Second, it is able to crimp at least a portion of a prosthetic valve, such as the upper inflow cuff of the prosthetic valve, by tensioning the cord in an axial direction. Third, it is able to release all, or substantially all, tension on the cord allowing for the portion of the prosthetic valve to expand and for the holder to slide back from the valve.

A cord may be connected to a delivery tool tensioning mechanism in any suitable manner, and a delivery tool may have any suitable tensioning mechanism. An example of a connection and tensioning mechanism is a cord comprising a wire, which can be wrapped around a coiling wheel. The coiling wheel could be positioned parallel with the center plane of the tool or at any other orientation with the center line of the tool. The coiling wheel could have magnets in it that allow for easy connection of a metal tether coupling to the wheel for the initial setup. In another embodiment, the cord may be pulled directly through a hole in the coiling wheel and after a few wheel revolutions the cord is firmly attached to the wheel.

Figure 26:
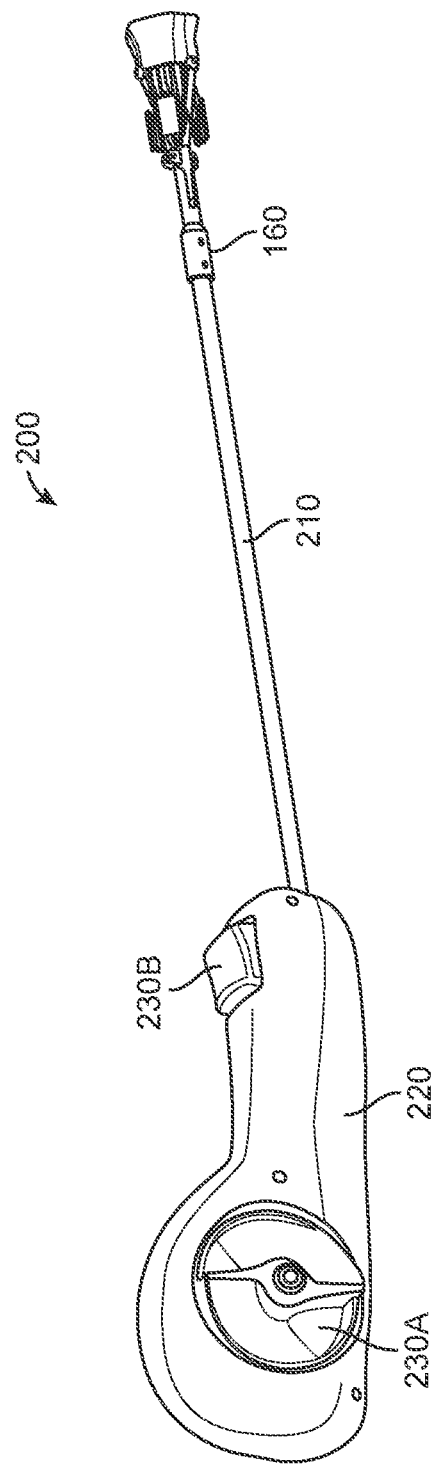
FIG. 26 is a schematic perspective view of an embodiment of a delivery system.
Figure 27:
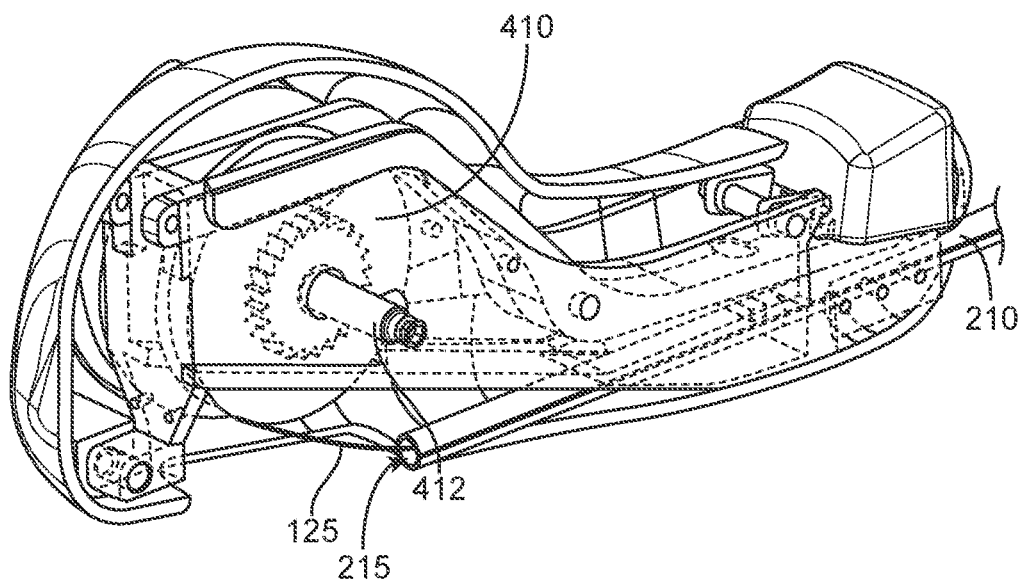
FIG. 27 is a schematic sectional view of an embodiment of a handle of a delivery system illustrating some components of an embodiment of a tensioning apparatus.

Embodiments of a delivery tool 200 comprising a coiling wheel as a tensioning mechanism are shown in FIGS. 26-27. As depicted in FIG. 26, a delivery tool 200 has a shaft 210 connected to an adapter of a holder 160. One or more cords (not shown in FIG. 26) extend through one or more conduits of shaft 210 and connect to tensioning mechanism housed within handle 220. The handle includes actuation mechanisms 230A, 230B, in this case as crank 230A and tension release button 230B. The crank 230A may be turned to increase or decrease tension on the cord. The tension release button 230B may be depressed to release all or substantially all of the tension on the cord.

FIG. 27 shows an embodiment of the tensioning mechanism of the delivery tool 200 depicted in FIG. 26. As shown, the shaft 210 has a lumen 215 that forms a conduit for cord 125, which is coupled to tensioning wheel 410. The tensioning wheel 410 may be rotated about shaft 412 to adjust tension on cord 125.

One example of a method that may be used for implanting a prosthetic valve with a delivery tool and holder, where the deliver tool has a tensioning mechanism and release mechanism (e.g., the embodiment depicted in FIG. 26), includes (1) snare and pull a cord to the delivery tool tensioning mechanism; (2) connect cord to tensioning mechanism; (3) actuate tensioning mechanism to constrict or crimp prosthetic valve; (4) crimp prosthetic valve with crimping device if needed or desired; (5) position prosthetic valve within surgical cavity of patient; (6) warm valve; (7) press release button of tensioning mechanism to allow expansion of prosthetic valve; (8) actuate tensioning mechanism to re-cinch/reposition prosthetic valve, if necessary; (9) pull tool/holder out of surgical cavity of patient while holding release button of tensioning mechanism; (10) confirm correct implant position of prosthetic valve; (11) cut cord and remove from around prosthetic valve.

Figure 28:
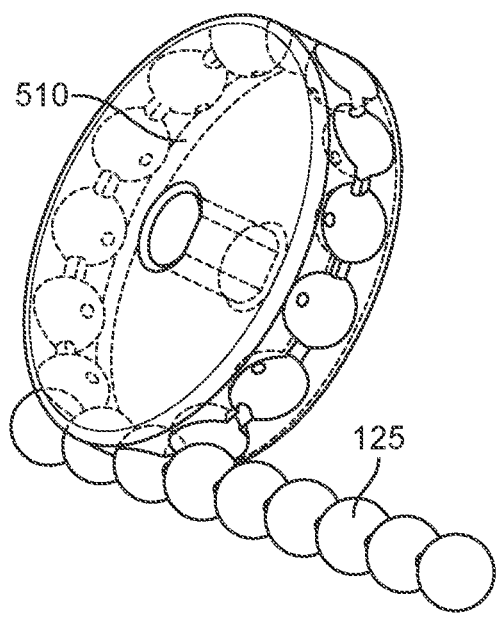
FIG. 28 is a schematic drawing of a perspective view of some components of an embodiment of a cord and an embodiment of a tensioning apparatus.

In some embodiments, the cord comprises a rack, beaded chain, belt and/or 3D pulley and the tensioning mechanism comprises a spur gear sprocket, screw and/or worm gear that engages with the cord. For example, FIG. 28 illustrates a cord 125 having a beaded chain and a sprocket 510 configured to engage the beaded chain. Rotation of the sprocket 510 can increase or decrease tension on the cord 125.

One way of advancing a belt with minimal components would be to use an indexing binding mechanism. One could use binding slotted components that grip when traveling in the proximal direction and are loose when traveling in the distal direction. This could be achieved by changing the angle from perpendicular with the belt in the non-grip direction and at a slight angle in the grip direction.

In addition to, or as an alternative to, using simple belts or flexible racks, unique geometries could be used such as a belt with a rough surface or a chain belt.

Examples of mechanisms for coupling cord to tension mechanism and for controlling tension mechanism are depicted in, and discussed with regard to, FIGS. A19-A40 of U.S. Patent Provisional Application No. 61/819,488, entitled SURGICAL HEART VALVES AND ASSOCIATED APPARATUSES, SYSTEMS AND METHODS, filed on May 3, 2013, which as indicated above is incorporated herein by reference to the extent that it does not conflict with the disclosure presented herein.

A tether adapter may form a part of a cord so that the cord may mate with a tensioning mechanism. The distal portion of the cord (e.g., a suture) may be potted into the adapter. Of course any other suitable mechanism, such as tying, adhesive, crimping, or the like, may be used to couple a distal portion of a cord with an adapter configured to mate with a tensioning mechanism. The adapter may have any suitable feature to mate with a tensioning mechanism such as a rack, beaded chain, belt, 3D pulley and/or the like. If cords are to be dependently controlled, such cords may together be coupled to a given tether adapter.

Figure 29:
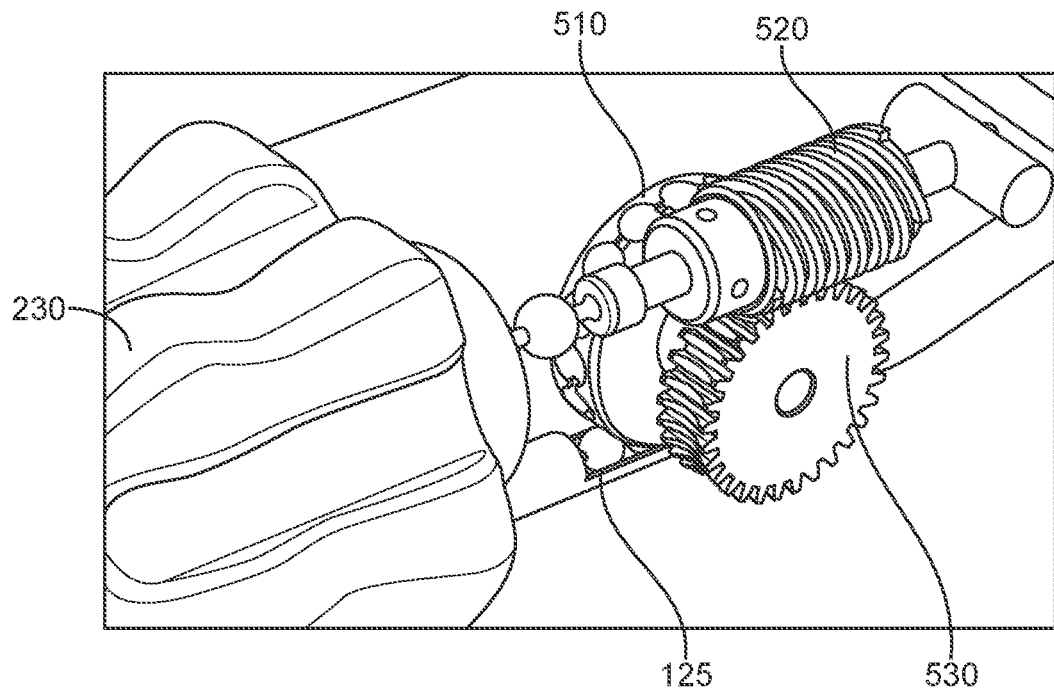
FIG. 29 is a schematic partial cut away view of an embodiment of a handle of a delivery system illustrating an embodiment of a tensioning apparatus.

An example of a delivery tool having a sprocket tension mechanism is shown in FIG. 29. In the depicted embodiment, the sprocket 510 engages a beaded chain of cord 125. The sprocket 510 is coupled to a spur gear 530 that engages gear 520. Rotational movement of actuation element 230 (in this case a rotatable knob) rotates gear 520, which causes spur gear 530 and sprocket 510 to rotate, thereby adjusting tension on cord 125.

One or more actuation elements may be placed at any suitable location of the handle of a delivery device. As shown in FIG. 26, actuation elements may be placed on a side (e.g., top, bottom, or side) of the handle. As shown in FIG. 29, an actuation element may be placed at the back of the handle. In some embodiments, the actuation mechanism is a button, switch, knob, lever, and/or the like, coupled to a motor and suitable control electronics. Accordingly, the tethering mechanism may be powered by a motor rather than manually actuating (e.g., ratcheting, turning, cranking, etc.) the mechanism.

Figure 30:
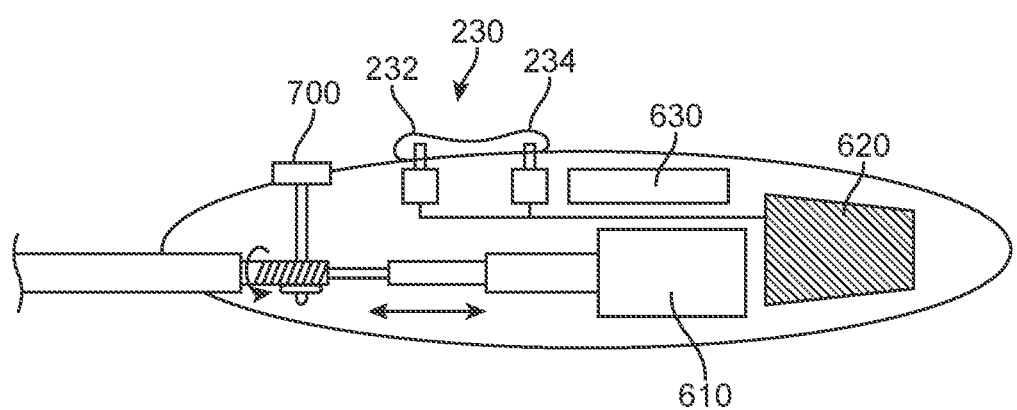
FIG. 30 is a schematic sectional view of an embodiment of a handle of a delivery system illustrating an embodiment of a tensioning apparatus.

An example of the tether tensioning function being accomplished with an electromechanical delivery system is shown in FIG. 30. In the housing of the handle of the delivery tool are disposed a motor 610, such as a linear servo motor or rotary motor with, for example, a spur rack interface, a power supply 630, control electronics 620, such as a circuit board, and appropriate connections to actuation elements 230, 270 disposed on handle. The power supply 630, control electronics 620, and motor 610 are operably coupled. The actuation elements 230, 270 may be actuated to control tension on a cord. By way of example, the front portion 232 of actuation element 230 may be depressed to increase tension, and the back portion 234 of element 230 may be depressed to decrease tension. A tension release button 700 may also be included.

Other mechanism or actuation elements that may be employed with powered delivery systems are shown in FIGS. A42-A47 of U.S. Patent Provisional Application No. 61/819,488, entitled SURGICAL HEART VALVES AND ASSOCIATED APPARATUSES, SYSTEMS AND METHODS, filed on May 3, 2013, which as indicated above is incorporated herein by reference to the extent that it does not conflict with the disclosure presented herein.

Remote Unit to Control Tension

In some embodiments, one or more actuation elements for controlling tension on one or more cords may be located away from the handle of the delivery tool. Such embodiments allow for the use of one hand to position the prosthetic valve and another to control constriction or expansion via tension on one or more cords or allow for two people to perform different aspects.

If the tension mechanism is powered, the tensioning mechanism may be disposed in the handle and the actuation mechanism may be a distance from the handle electrically or remotely coupled to the tensioning mechanism in the handle.

Figure 31:
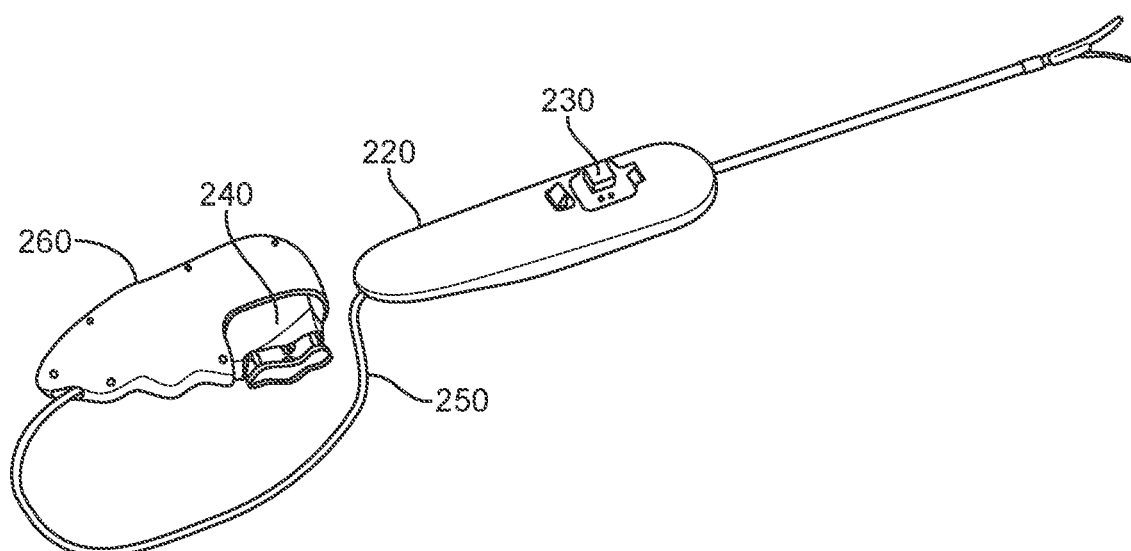
FIGS. 31-32 are schematic drawings of perspective views of embodiments of delivery systems.
Figure 32:
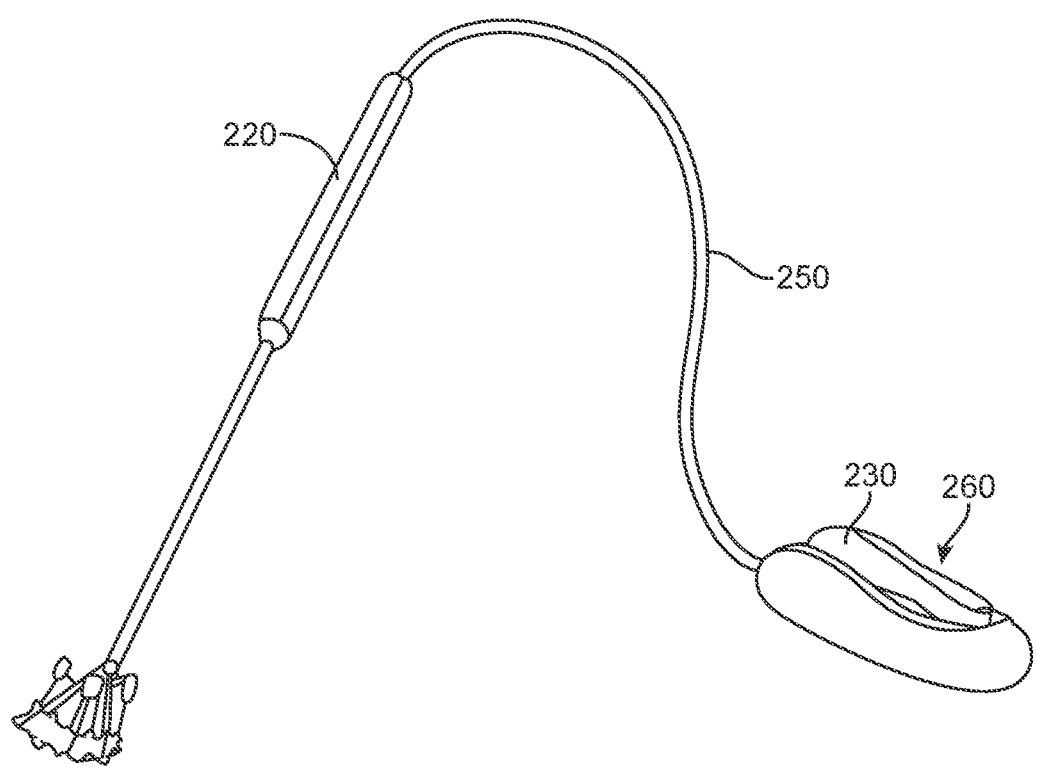

Examples of delivery systems with actuation elements away from a handle of a delivery tool are shown in FIGS. 31-32. In the embodiments depicted in FIG. 31, the handle 220 includes an actuation element 230 and remote unit 260 includes another actuation element 240 coupled to the handle 220 via flexible shaft 250. This allows a user (or two users) to employ one hand (or one user) to position the prosthetic valve via handle 220 and actuate element 230 and to use another hand (or another user) to actuate element 240 on remote unit. Actuation elements 230, 240 may be used to control tension of the same or different cords. If used to control the same cord, a user may choose which hand (or which user) to use. In some embodiments, actuation element 230 is a tension release actuation element and actuation element 240 is a tension control element.

In the embodiment depicted in FIG. 32, handle 220 does not include actuation elements, while remote unit 260 that is coupled to handle 220 via flexible shaft 250 includes one or more actuation elements (only one, 230, depicted).

Other embodiments are depicted in, and discussed with regard to, FIGS. A42-A43 of U.S. Patent Provisional Application No. 61/819,488, entitled SURGICAL HEART VALVES AND ASSOCIATED APPARATUSES, SYSTEMS AND METHODS, filed on May 3, 2013, which as indicated above is incorporated herein by reference to the extent that it does not conflict with the disclosure presented herein.

Adjustable Shaft Concept

Some surgeons may have different preferences on the shaft length of the handle depending on any given patient. Accordingly a shaft of a delivery tool described herein may have any suitable length or may be adjustable. Embodiments of adjustable length shafts using, for example a lock/unlock switch, are depicted in and discussed with regard to FIG. A51 of U.S. Patent Provisional Application No. 61/819,488, entitled SURGICAL HEART VALVES AND ASSOCIATED APPARATUSES, SYSTEMS AND METHODS, filed on May 3, 2013, which as indicated above is incorporated herein by reference to the extent that it does not conflict with the disclosure presented herein.

Cord Cutting Mechanisms

One way to cut a cord after the prosthetic valve is properly implanted is to have the user take scissors to cut the cord.

Another way is to have the cords automatically cut. This could occur in the delivery system handle, in the shaft, within the holder, etc. Some of the ideas contemplated herein include rotation of a sharp disk, the axial travel of sharp edges, or simply having a raised cut-point on the holder as is done on many surgical valves. In one version, one end of the cord (in embodiments where two arms are fed through a holder, shaft or delivery system) would remain fixed to the holder shaft, or delivery system, etc. allowing for the cords to be pulled out with the delivery system handle. A second contemplation would leave the cords about the valve after the delivery system has been removed, allowing for each of the cords to be pulled out individually. A third contemplation would have each of the cords automatically pulled from the valve incrementally by the delivery system.

Examples of cutting apparatuses incorporated into a delivery tool are shown in FIGS. A13-A14 and A48-A50 of U.S. Patent Provisional Application No. 61/819,488, entitled SURGICAL HEART VALVES AND ASSOCIATED APPARATUSES, SYSTEMS AND METHODS, filed on May 3, 2013, which as indicated above is incorporated herein by reference to the extent that it does not conflict with the disclosure presented herein. An example of a raised cut point for manual cutting or a cord is shown in FIG. A15 U.S. Patent Provisional Application No. 61/819,488.

In some embodiments, the cords are severed in the handle and the handle is disconnectable from the shaft. After the cord cutting element is actuated, the handle is disconnected from the shaft. The shaft may be held such that the holder remains in position (e.g., at the level of the upper inflow cuff) and the sutures may be pulled out one at a time. Because the sutures are being pulled radially from the prosthetic valve (due to holder being in place), not vertically, there is little or no risk of valve dislodgement from pulling the sutures from the valve.

In some embodiments, automatic cord removal occurs when the delivery tool handle is retracted. In such embodiments, it is desirable to maintain the holder in position relative to the prosthetic valve. Because the holder is at the level of the loops (e.g., valve inflow cuff), the forces are all radial and there is little to no risk of valve dislodgement from this process.

Embodiments with Offset Holder

The discussion provided in this section is generally directed to holders with extensions offset from the longitudinal axis of a prosthetic valve. However, it will be understood that some of the discussion presented in this section may be applicable to any holder or delivery system described herein (e.g., the discussion below regarding crimp limiters, quick connects, handle and actuation element configurations, implant procedure, etc.).

Figure 33:
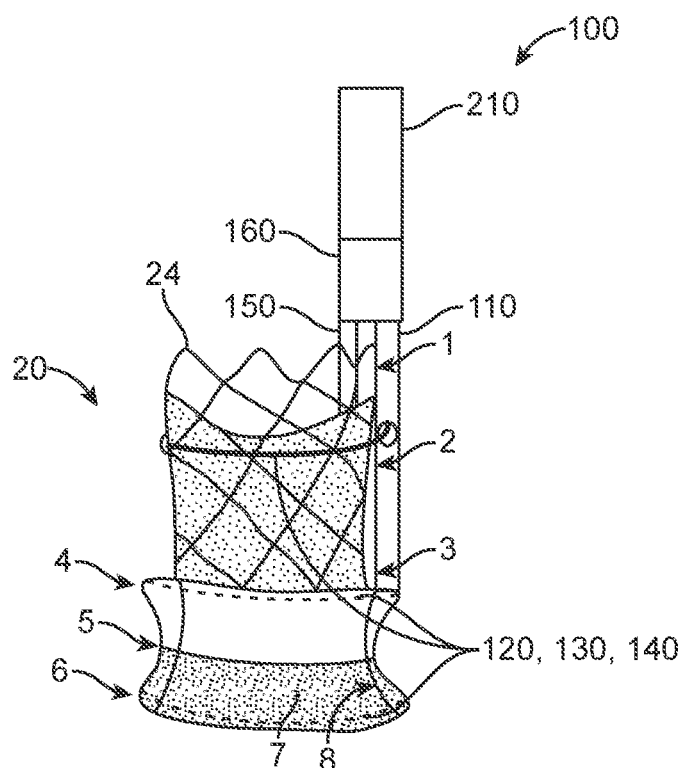
FIG. 33 is a schematic side view of an embodiment of a holder and an embodiment of a prosthetic valve.

In some embodiments, a holder and shaft of delivery device is offset from a longitudinal axis of a prosthetic valve to improve the physician's view during implant. One such embodiment is depicted in FIG. 33. As depicted, the holder 100 includes two extensions 110, 150 (but many contain any suitable number of extensions) and an adaptor 160 to retain relative positions of extensions and to manage cords (e.g., as discussed above with FIGS. 1-9). The adaptor 160 is configured to connect to shaft 210 of a delivery tool such that the shaft and holder are offset and generally parallel to the longitudinal axis of the prosthetic valve 20. In the depicted embodiment, extension 110 extends on the exterior of the valve 20 (i.e., not within a central opening of self-expanding frame 24) while extension 150 extends within a central opening of self-expanding frame 24.

In the embodiment depicted in FIG. 33, the prosthetic valve has an upper inflow region 4 at the top of the skirt, a lower inflow region 6 at the bottom of the skirt, and a skirt waist 5, as well as an upper outflow region 1, a middle outflow region 2, and a lower outflow region 3. When discussing a holder or delivery device in this section, a prosthetic valve as depicted in FIG. 33 will often be described. However, it will be understood that the holder and delivery systems described in this section may be used to deliver prosthetic valves with other configurations.

Still referring to FIG. 33, the holder 100 has three loops 120, 130, 140, with one loop being disposed about the upper inflow region 4 of the prosthetic valve 20, another being disposed about the lower inflow region 6, and the other being disposed about the middle 2 to upper 1 inflow region.

As shown in FIG. 33, a valve apparatus may include a skirt having an upper edge, a lower edge and a waist. The skirt may include a marking 7 to facilitate alignment with the patient's annulus, one or more markings 8 for alignment with commissures, or both markings 7, 8. Additional information regarding markings is described in U.S. Provisional Patent Application No. 61/819,486, entitled SURGICAL HEART VALVES AND ASSOCIATED APPARATUSES, SYSTEMS AND METHODS, filed on May 3, 2013, U.S. Provisional Patent Application No. 61/930,851, entitled SURGICAL HEART VALVES AND ASSOCIATED APPARATUSES, SYSTEMS AND METHODS, filed on Jan. 23, 2014 and in U.S. patent application Ser. No. 14/268,393, entitled MEDICAL DEVICES FOR IMPLANTING IN A VALVE AND ASSOCIATED METHODS, filed on the same day as the present nonprovisional application, which patent applications are hereby incorporated herein by reference to the extent that they do not conflict with the present disclosure.

Figure 34A:
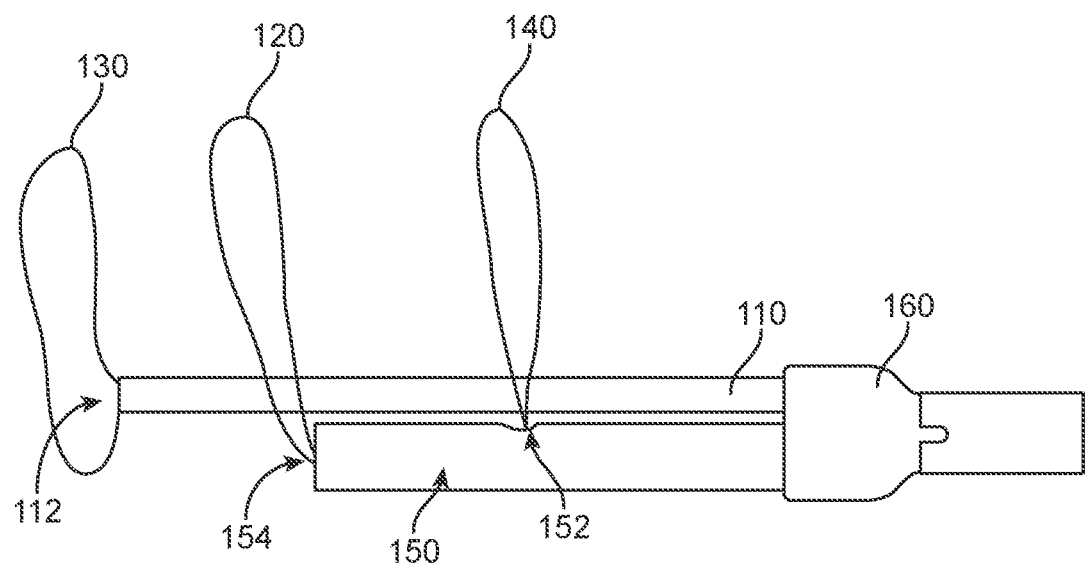
FIG. 34A-B are schematic diagrams of a side view (34A) and a sectional view (34B) of an embodiment of a holder.

Referring now to FIG. 34A, a schematic drawing of an embodiment of a holder depicted in FIG. 33 is shown without the captured prosthetic valve device 20. From an opening 112 in one extension 110 a loop 130 exits. From a first opening 154 of the other extension 150 a loop 110 exits, and from a second opening 152 of the extension 150 another loop 140 exits. A portion of the cords that form the loops 120, 130, 140 extend through conduits in the extensions 110, 150 and through adaptor 160. The extensions and adaptor may have any suitable number of conduits.

Figure 34B:
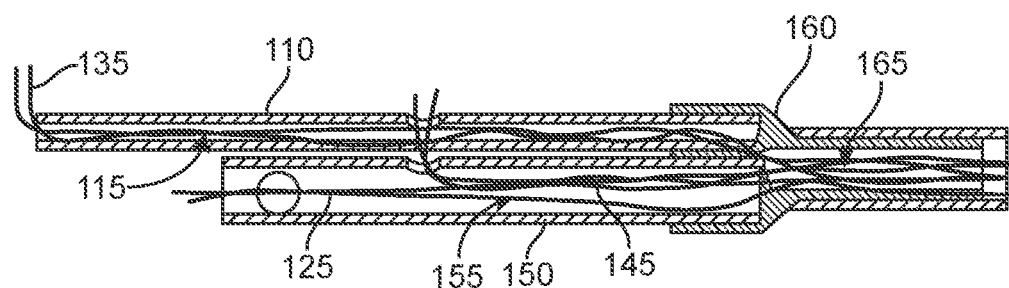

Referring now to FIG. 34B, an embodiment of a longitudinal section of the holder depicted in FIG. 34A is shown. In the depicted embodiment, the first extension 110 has a conduit 115 extending the length of the extension, the second extension 150 has a conduit 155 extending the length of the extension, and the adaptor 160 has a conduit 165 extending the length of the adaptor. The conduit 165 of the adaptor is in communication with the conduit 115 of the first extension and the conduit 155 of the second extension. A portion of the cord 125 forming a loop (not depicted in FIG. 34B) extends through the conduit 115 of the first extension and the conduit 165 of the adaptor; and portions of the cords 125, 145 forming loops (not depicted in FIG. 34B) extend through the conduit 155 of the second extension and the conduit 165 of the adaptor. While one conduit is depicted for each of the first extension, the second extension and the adaptor, it will be understood that a holder and its components may have any suitable number of conduits for managing the cords. End portions of the cords that extend beyond the adaptor (and delivery system shaft) may be operably coupled to one or more tensioning apparatus and actuation elements for controlling the tensioning apparatus (e.g., as discussed above). The loops may be controlled individually or as a group of two or more.

While the holder depicted in FIGS. 34A-B includes two extensions, it will be understood that a suitable holder may comprise any other suitable number of extensions. For example, if three loops are employed, the holder may reasonably have one, two or three extensions.

The holder, loops or handle may be configured to restrict or limit the amount that any one or more loops may be constricted to limit crimping of the valve apparatus, thereby preventing the valve from being over crimped. Any suitable crimp limiter may be employed. In embodiments, crimp limiting may be accomplished by assembling a bead to one of the loop lines and assembling a crimp sleeve behind the bead, which then limits the amount of travel that the loops can travel. Limiters may be placed on any one or more loop lines. Preferably, a limiter is placed on a loop that is configured to retain a valve apparatus in an outflow region, such as the upper skirt/lower outflow region.

In some embodiments, two or more loops may be actuated by the same mechanism. In such embodiments, a travel stop for one of the loops can effectively limit crimping of all of the loops controlled by the same mechanism.

In some embodiment, a crimp limiter is not employed for a loop at a lower inflow region. The lower inflow region presents less concern regarding damaging the valve or frame. Of course, a crimp limiter may be employed for a loop in this region.

A crimp limiter (e.g., travel stop described above) preferably can be manufactured in a consistent manner. For the embodiment described above, the travel stop relies on precise knot tying and loop line lengths to get low variability in crimp stop locations. To facilitate a low variability assembly process, manufacturing fixturing may be employed to an effective design. In embodiments, fixturing can involve posts to hold a valve apparatus in place and posts to set the suture length where the knots/crimp sleeves belong. By using crimp sleeves, the travel stops may be reproducibly placed. Crimp sleeves alone may not be strong enough for the forces seen with cinching the valve, so knots can be placed directly behind or in front of the crimp sleeve that prevent slipping of the travel stops.

An overview of an embodiment of a manufacturing process for operably coupling a holder to a valve apparatus includes assembling loops to commissures of a frame of a valve apparatus at three levels. Next a bead is assembled to one arm of a loop configured to retain the valve apparatus in the upper skirt region. Next the holder is assembled onto the three cinch loops. Next a crimp sleeve or quick connect component is added and excess loop material length is trimmed.

In embodiments, one or more loops are coupled to the valve apparatus (e.g., to the frame) to prevent the loops from slipping off of the valve apparatus. In embodiments, the loops are coupled via the commissures. In embodiments, the loops are coupled via sutures. Of course, the loops may be coupled in any suitable location and in any suitable manner. For example, the frame could have a curled pig tail that constrains the loop, the frame could flare outwards to prevent the suture from sliding off, etc.

Figure 35:
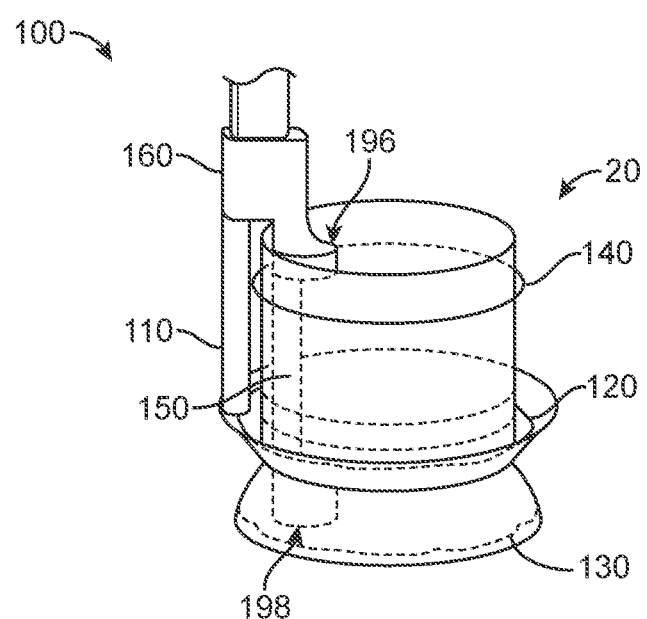
FIG. 35 is a schematic drawing of an embodiment of a holder having crimp limiting elements and an associated prosthetic valve.

Referring now to FIG. 35, an embodiment of a holder 100 having disc-shaped crimp limiting elements 196, 198 is shown. The holder 100 is positioned such that one extension 110 or leg is outside of prosthetic valve 20 and one extension 150 is positioned within a central opening of valve 20. The disc crimp limiters 196, 198 are formed as a part of, or are attached to, extension 150 configured to be positioned within the prosthetic valve 20. Crimp limiting elements 196, 198 limit the amount that a frame of device 20 can be crimped, because the frame will engage the limiting elements 196, 198 and constrict no further, even if further tension is applied to loops 120, 130, 140. In the embodiment depicted in FIG. 35, loops 120 and 140 may be controlled together. Accordingly, crimp limiting element 196 can serve to prevent further crimping by both loops 120, 140 because stopping further crimping of one loop will stop further crimping of the other loop if the loops are dependently controlled. Crimp limiting element 198 can serve to limit crimping by independently controlled loop 130 positioned around the inflow region of the valve 20.

A holder may include any suitable number of crimp limiting disc-shaped elements. In some embodiments, a holder includes one disc-shaped crimp limiting element for each loop or group of loops that surrounds a portion of a valve. In some embodiments, a holder includes one disc-shaped crimp limiting element for each loop or set of loops that are independently controllable. In some embodiments, a disc-shaped crimp limiter is a cylinder. A cylinder can effectively limit crimping of a plurality of independently controllable loops.

Referring now to FIGS. 36A-B, a prototype of an embodiment of a holder depicted in FIG. 35 is shown positioned within an embodiment of a valve. The schematic drawings in FIGS. 36A-B are bottom-up views, showing crimp limiting element 198, loop 130 and lower inflow region 6 of prosthetic valve. FIG. 36A shows the valve in an expanded configuration. FIG. 36B shows the valve in a constricted configuration, where crimping is limited by crimp limiting element 198.

In embodiments, where the holder is a side mounted holder (e.g., the embodiments described above in this section), a seam is preferably at a commissure location where the holder is or will be attached to facilitate uniform crimping.

In embodiments, the valve apparatus is configured to flare at the skirt at the lower inflow region. When the valve is implanted using a tool as described herein, the skirt may be allowed to flare at the lower inflow region while the outflow and upper inflow remain crimped (e.g., through the use of more than one loop—e.g., loops 110 and 140 as described above). FIG. 37 presents a schematic drawing of a flared skirt at the lower outflow region 6 and crimped upper inflow 4 and outflow 1, 2, 3 regions. The skirt waist is properly aligned with the annulus 14 of the native valve in the drawing shown in FIG. 37.

Preferably, a delivery tool described herein allows for rapid connection of a handle to the apparatus for controlling the diameter of the loops. With embodiments of systems as described herein, the loading process can take seconds as opposed to minutes with previously available systems.

To facilitate rapid loading, a quick connect system may be employed. In embodiments, quick connection can be achieved by having two cords or sets of cords on the valve, one for the outflow and one for the inflow, which quickly connect with the delivery handle actuators via arms that engage a bead. By allowing the surgeon to quickly disconnect and reconnect, they may set the tool aside during positioning confirmation, and reconnect if necessary to reposition the valve.

Figure 38:
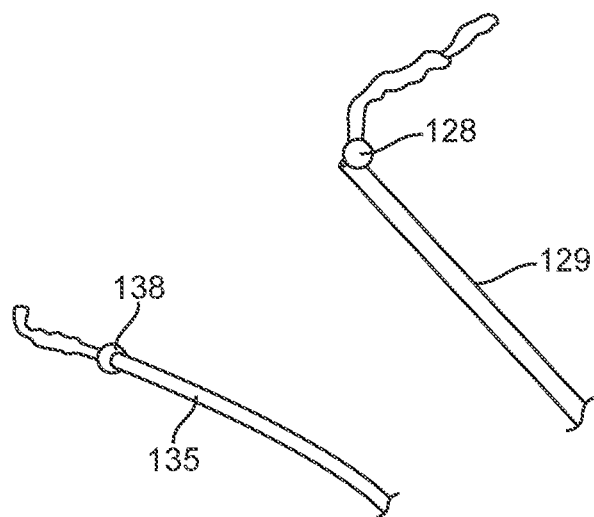
FIG. 38 is a schematic drawing of embodiments of cords having capture features.

An example is depicted in FIG. 38, where a first cord 129 includes a first quick connect mechanism, such as the ball 128 depicted; and second cord 135 includes a first quick connect mechanism, such as the ball 138 depicted. One or both of the first and second cords may include more than one cord. For example, cord 129 may include cord 125 and cord 145 as depicted in FIG. 34B, because in some embodiments constriction and expansion of loops of such cords may be dependently controlled.

Figure 39A:
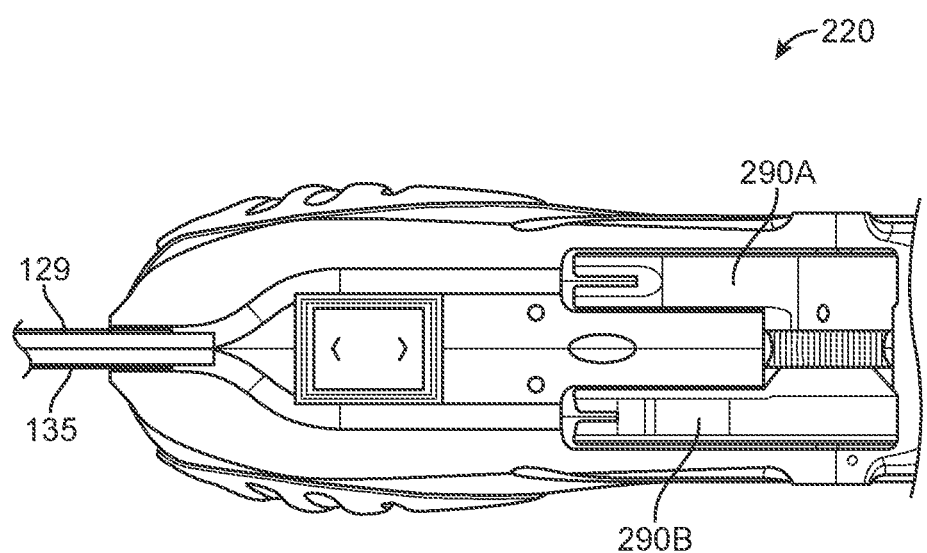
FIG. 39A is a schematic bottom view of an embodiment of a handle of a delivery system.
Figure 39B:
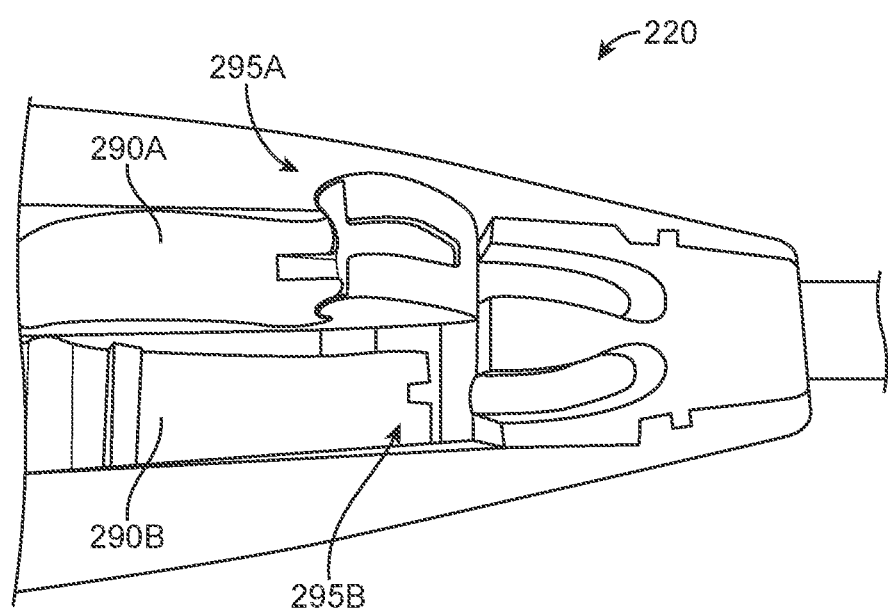
FIG. 39B is schematic drawing of a bottom of an embodiment of a handle of a delivery system.

Referring now to FIGS. 39A-B, handles 220 of a delivery system having quick connect mechanism configured to cooperate with quick connect tether adapters (e.g., as shown in and discussed above with regard to FIG. 38) are shown. In FIG. 39A, a schematic drawing is shown. In FIG. 39B, schematic drawing of a prototype is shown. As depicted, the handle 220 includes channels or conduits through which one or more cords 129, 135 may run. Handle includes swinging arms 290A, 290B that are configured to capture or release tether adapters of cords 129, 135. The arms 290A, 290B include curved ends 295A, 295B with slots for receiving the cords. The width of slots sufficient large to receive a portion of the cord distal to a capture feature (e.g., balls 128, 138 depicted in FIG. 38) but less than the width or diameter of the capture feature. For example, the capture feature (e.g. bead or ball) may be snagged by swinging arms. When unactuated a plunger (or other suitable element) may push the capture feature (e.g., bead or ball) out of the actuator arms.

Figure 40A:
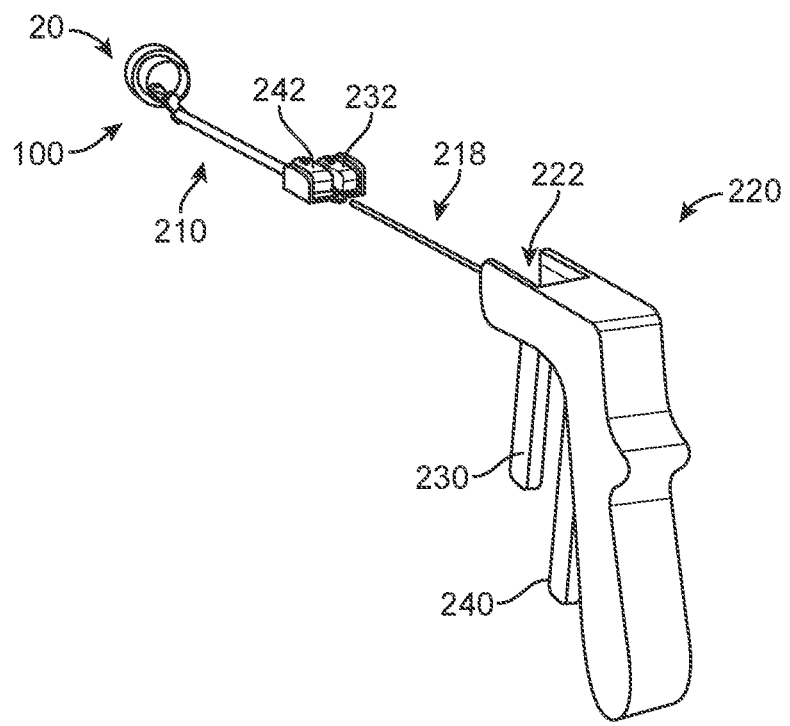
FIGS. 40A-C are schematic perspective views of an embodiment of a handle and holder of a delivery system.
Figure 40B:
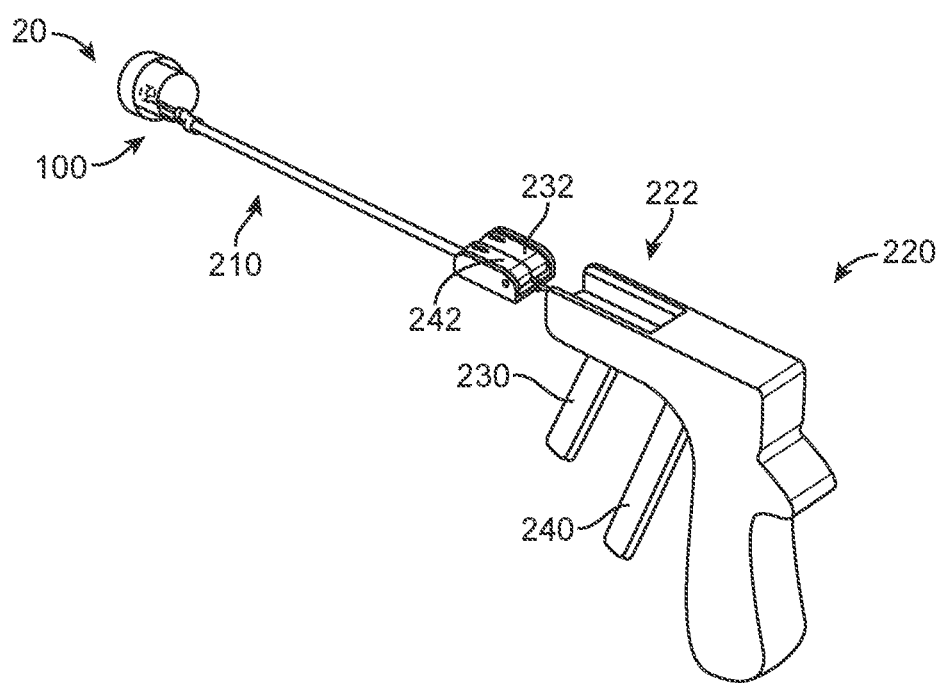
Figure 40C:
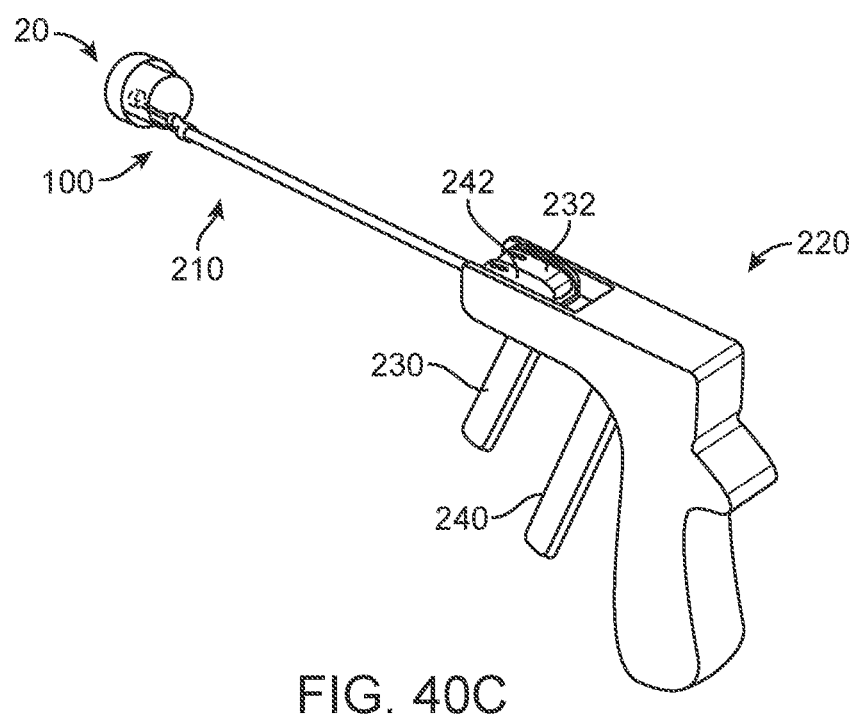
Figure 41:
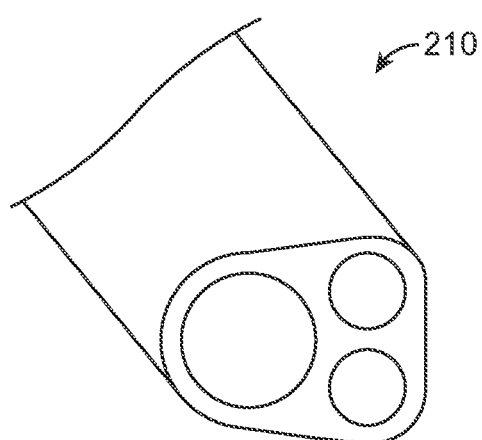
FIG. 41 is a schematic perspective view of a portion of an embodiment of a shaft of a delivery system.

Referring now to FIGS. 40-41, a delivery system having quick connect elements is depicted. The system includes a holder 100 (e.g., any holder as described above), a shaft 210 through which cords may run, and a handle 220. The handle includes two actuation elements 230, 240, in this case triggers, and a recess for receiving a actuation elements 232, 242. Actuation elements 232, 242 are coupled to cords that control loops that control constriction and expansion of prosthetic valve 20. Actuation elements 232, 242 can include gears coupled to tether elements of the cords. Handle 220 can include cooperating gears that are operably coupled to actuation elements 230, 240. When actuation elements 232, 242 are received by recess 222 of handle, gears within the handle can engage gears within actuation elements 232, 242 such that triggers 230, 240 may be actuated to increase or decrease tension on the cords to control constriction or expansion of prosthetic valve 20.

As shown in FIGS. 40A-C, handle may include rod 218 to facilitate proper coupling of handle 220 with actuation elements 232, 242. Rod 218 of handle 220 may be inserted into a lumen of shaft 210 to align handle 220 relative to shaft 210. Shaft 210 may be advanced over rod 218 until actuation elements 232, 242 are properly received into recess 222 of handle 220.

Referring now to FIG. 41, a schematic view is shown of a portion of an embodiment of a shaft 210 that may be used with a system depicted in FIGS. 40A-C. Shaft 210 includes lumens 212, 214 through which cords may run. Each lumen 212, 214 may receive one or more cords. In some embodiments, lumen 212 receives one cord which is coupled to a first actuation element on shaft, and lumen 214 received two cords with are both coupled to a second actuation element on shaft. Shaft 210 also includes lumen 216 configured to receive rod of handle.

A handle may take any suitable form and have any suitable actuation element to control the diameter of a loop. For example, the handle may be in one of the following form factors: pistol, bike break, pen style (with appropriate motor), transcatheter delivery system (rotary knobs), syringe, thumb wheel, or the like. Examples of such handles and actuation elements are depicted in, and discussed with regard to FIGS. 11-20 of U.S. Provisional Patent Application No. 61/930,905, entitled VALVE DELIVERY TOOL, filed on Jan. 23, 2014, which as indicated above is incorporated herein by reference to the extent that it does not conflict with the present disclosure.

Figure 42:
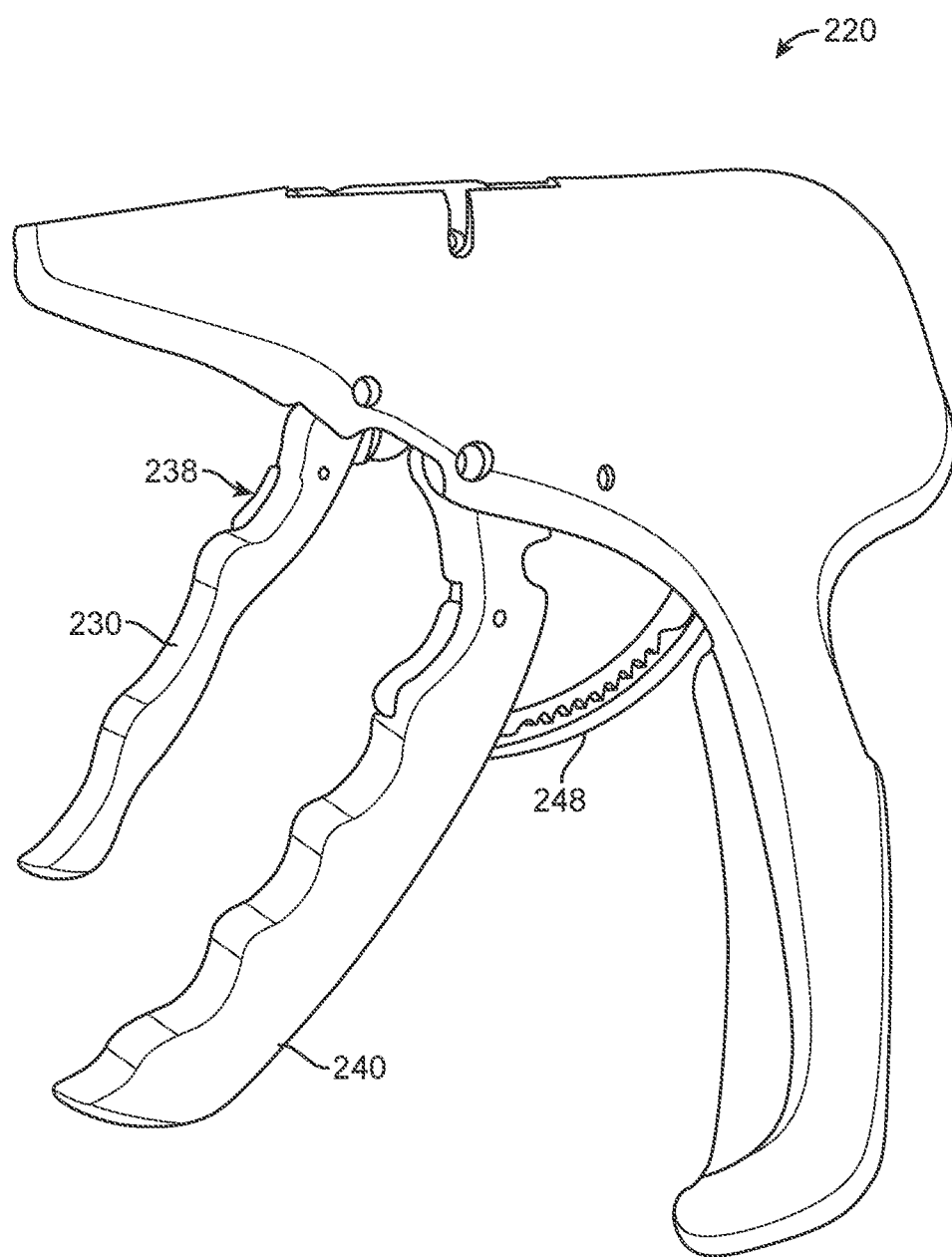
FIG. 42 is a schematic side view of an embodiment of a handle of a delivery system.
Figure 43:
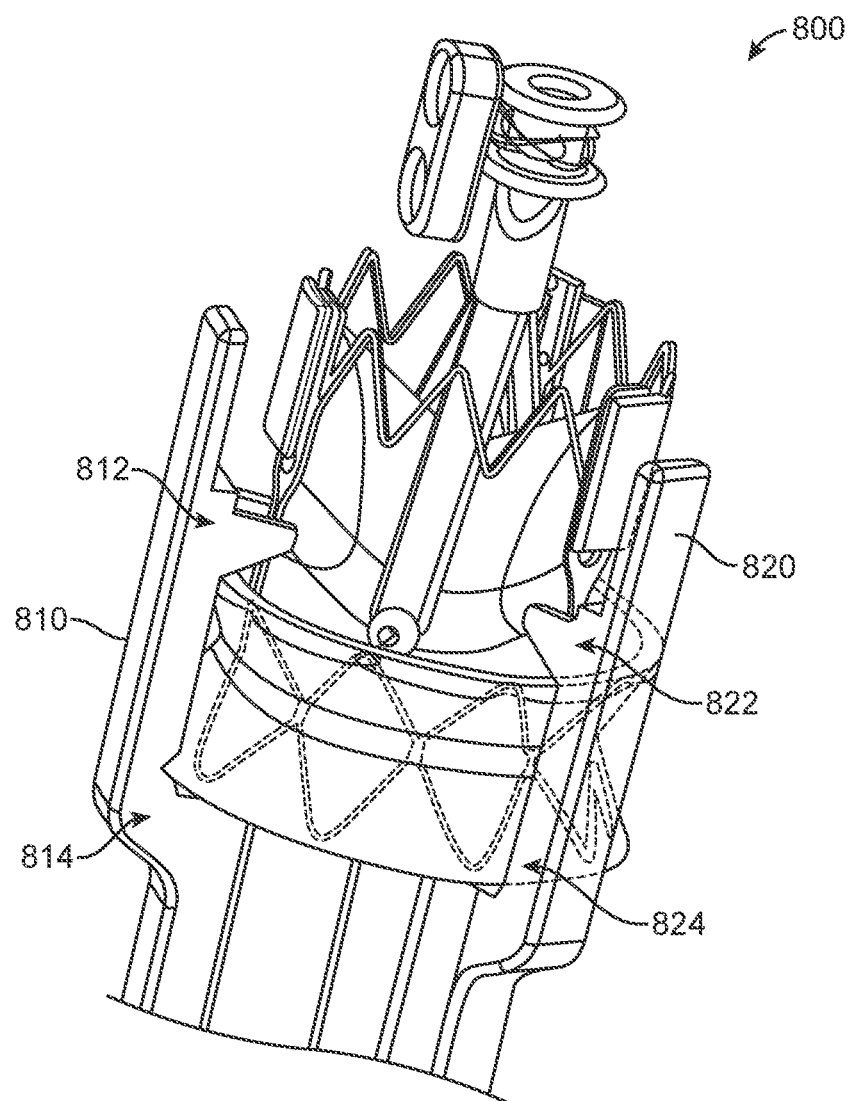
FIG. 43 is a schematic perspective view of an embodiment of a crimping guide and an embodiment of a prosthetic valve.
Figure 44A:
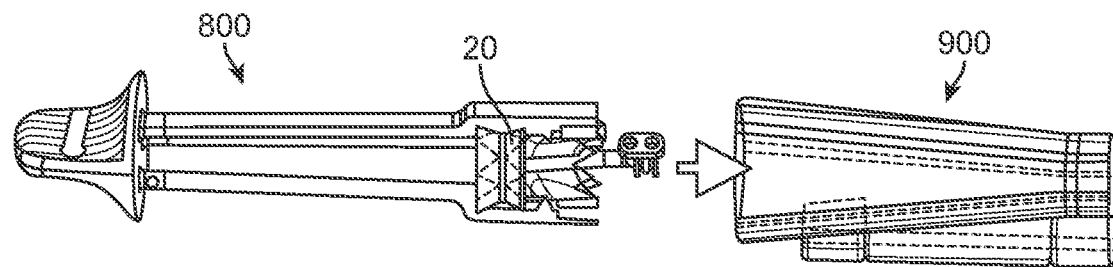
FIGS. 44A-B are schematic side views of embodiment of a crimping guide, an embodiment of a prosthetic valve, and an embodiment of a crimping funnel.
Figure 44B:
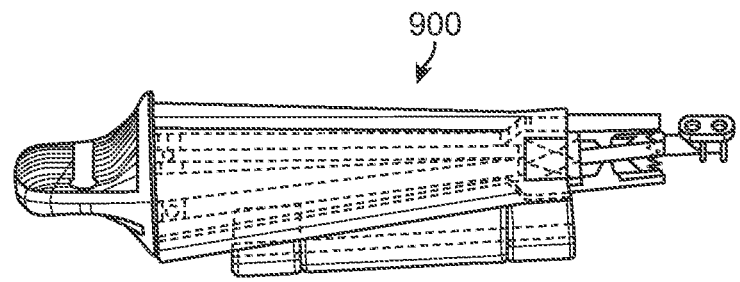

For example and with reference to FIG. 42, a handle 220 having trigger-like actuation mechanisms 230, 240 is shown. In the depicted embodiments, the handle 220 includes locking elements 238, 248. Locking elements 238, 248 are configured to lock trigger 230, 240 position. Locking elements 238, 248 are releasable one way locking elements. As triggers 238, 248 are squeezed, locking elements 238, 248 lock trigger at predefined intervals (e.g., at intervals defined by teeth). Such locking mechanisms may be advantageous when manual actuation elements 230, 240 are employed (as opposed to motorized elements), otherwise human force may need to be maintained on triggers to retain a prosthetic valve in a crimped position. Maintenance of force for extended periods of time (e.g., several seconds or more) can be difficult, particularly while the prosthetic valve is being positioned. Such locking mechanisms may also be advantageous when a medical assistant crimps the prosthetic valve and retains a crimped configuration of the valve with a delivery system, and then hands the delivery system to a surgeon for implanting. It will be understood that the locking mechanisms depicted in FIG. 42 are shown for purposes of example and that other suitable locking mechanisms are contemplated herein.

In some embodiments, a delivery system includes a crimp lockout mechanism to prevent an excessive number of crimping and uncramping events. Typically, prosthetic valves can be crimped only a few times (e.g., three times) before their use is no longer advised. Any suitable crimp lockout mechanism can be used. For example, if actuation mechanisms of the delivery system is motorized and the delivery system includes control electronics, the number of crimping and uncramping events may be counted electronically until a maximum number or crimping and uncramping events is reached. Further crimping may be prevented to cause a new prosthetic valve to be used. If the actuation mechanisms are manual, the crimp lock out mechanism may be, for example, a geared dial with a peg that advances a set number of times before the peg advances to a position that prevents further crimping. Of course, any other suitable lockout mechanism may be employed.

An overview of an embodiment of a method of implanting a surgical replacement valve apparatus using an embodiment of a delivery tool described herein presented below. The holder includes one or more loops to control the extent which the valve frame is expanded or collapsed. In a first step, a handle is operably coupled to the holder such that the handle may be used by a surgeon to control the extent to which the loops contract or allow expansion of the frame. Next, the valve is collapsed (i.e., crimped) by reducing the diameter of the one or more loops by manipulation of one or more actuation elements on the handle. Next, the valve is positioned in the crimped state. Next, the lower skirt is allowed to expand by increasing the diameter of a loop previously constricting the skirt by manipulation of an actuation element on the handle. Next, the outflow portion of the frame is expanded by increasing the diameter of one or more loops previously constricting the outflow portion of the frame by manipulating one or more actuation elements of the handle. Next, the handle may be removed and the position of the valve verified. If the position is determined to be improper, the handle may be recoupled to the holder and the valve may be repositioned. Preferably, the valve is not crimped and released more than two or three times before proper positioning is achieved. If positioning is determined to be proper, the loops or an extension thereof may be cut and removed. In embodiments, the loops may be formed of suture wire or thread. Of course, any other suitable biocompatible material may be employed.

Sheath Delivery System

Embodiments of delivery systems described in this section may reduce the valve to a diameter no greater than 14 mm. The valve is connected to the delivery tool via a threaded holder; however, a snap fit and/or other mechanisms are also contemplated. A clamshell funnel is then assembled onto the end of the delivery tool's sheath, and the sheath is advanced over the prosthetic valve (valve is stationary). This is achieved via a thumb wheel on a rack. Various gear ratios and orientations of such wheels/knobs have been prototyped. Prior to pulling the skirt into the sheath, the sheath may be spun to align the sheath commissure markers with the valve skirt's commissure markers. After the valve is fully sheathed, the funnel is pulled off of the delivery tool. The valve may be chilled prior to loading, however depending on the valve it may not necessary.

The valve may then be heated via syringe or luer port on the handle, and the prosthetic valve is placed within the surgical cavity of the patient and lowered to a level just below the native valve annulus using the delivery tool. The user then retracks the sheath via the thumb wheel interface, and allows the skirt to expand into a flared geometry. The user then observes the commissure markings and waist markings, and clocks the commissure markings with the native commissures and pulls the valve up against the native valve annulus, such that the waist marking correlates closely to the native valve annulus. The user then fully deploys the prosthetic valve and confirms positioning.

If the user is not satisfied with the positioning, they may advance the sheath over the valve to reposition it. While the inflow skirt may not be able to be pulled into the sheath, enough reduction may be derived from the crimping of the rest of the valve to allow the valve to be repositioned.

After the user is satisfied with the positioning, they cut the sutures, for example at a single cutpoint on the valve holder, and remove the delivery tool & holder from the surgical cavity. By using flexible sutures between the holder and the valve, the user may easily move the delivery tool out of the way while confirming valve positioning. Additionally, a user can tug on the valve without dislodging it to confirm sufficient engagement force. Because the sutures are loosely secured to the valve, a single rigid leg is necessary to push the valve out of the sheath during deployment. If the rigid leg were not present, the valve may only advance after the slack of the suture was removed and then the valve may uncontrollably shoot out of the sheath after the tension between the skirt and the sheath is reduced.

Sheath delivery tool embodiments are depicted in and discussed with regard to FIGS. A72-A78 of U.S. Patent Provisional Application No. 61/819,488, entitled SURGICAL HEART VALVES AND ASSOCIATED APPARATUSES, SYSTEMS AND METHODS, filed on May 3, 2013, which as indicated above is incorporated herein by reference to the extent that it does not conflict with the disclosure presented herein.

A motorized sheath delivery system is depicted in and described with regard to FIGS. B1-B4 of U.S. Patent Provisional Application No. 61/819,490, entitled SURGICAL HEART VALVES AND ASSOCIATED APPARATUSES, SYSTEMS AND METHODS, filed on May 3, 2013, as indicated above is incorporated herein by reference to the extent that it does not conflict with the disclosure presented herein. As indicated in the previously filed provisional patent application, surgeons have indicated a preference for a handle configuration that encompasses a pen like grip and that requires minimal force in deploying sutureless prosthetic valves. Preferably, this force is imparted from either their thumb or index finger. Due to the large forces involved in crimping a super elastic prosthetic valve, it can be difficult to maintain control during prosthetic valve deployment when the surgical instrument is purely mechanical. To overcome this challenge, an electronic handle has been developed that allows for the user to use a pen-like grip while imparting very little force with their fingers, allowing for maximal control of prosthetic valve deployment.

Several types of motors may be used to control deployment of a sutureless valve. Both stepper and servo motors may be used. However, the lack of sufficient torque achievable in a small motor may result. Therefore, a DC motor combined with a high gear ratio may be used to achieve a sufficient torque to control deployment of a sutureless prosthetic valve.

An advantage to a DC motor is that a circuit board is not necessary to control the DC motor. For example, an H-bridge circuit may be simulated using two push buttons. However, this may present difficulties with regard to controlling the speed of the motor. The speed would always be the maximum allowed by the chosen battery/motor. It is preferred that the user be able to control the speed with which the valve deploys or is recaptured. In some embodiments there are two push buttons, one for forward and one for reverse. If this configuration were used, the motor may go forward at a slow speed for a few seconds, but when the button is held for longer periods of time the speed may ramp up to maximum speed. This would allow the user to rapidly get the sheath back, as would be desired after the inflow of the valve has been deployed. Another button configuration would involve a rocker switch with a potentiometer, where the further forward the switch is rocked, the greater the speed. If the switch were rocked only slightly forward, there would be a very slow velocity of deployment.

For turning the device on, the device could have an on/off switch, or a circuit board that has a "shake-awake" feature.

The delivery handle may have a motor interfacing with a rack via a pinion; however, other versions could also be used, such as a worm with a worm-rack, allowing the motor and rack to be parallel. Additionally, the motor could spool a cable or suture.

Another feature that can be added is a light source, such as an LED light, in the delivery tool shaft or sheath. This would allow illumination of the surgical cavity, providing the surgeon with better visibility of the valve while confirming valve deployment position. The LED could be placed entirely within the sheath, on the outside of the sheath, or partially in and out of the sheath. Multiple LEDs could be used to provide additional illumination. Preferably, the light would turn on when the user moves the handle or depresses the deployment button and remain on for a set period of time, such as 10 seconds.

IV. Accessory Devices to Facilitate Implanting Prosthetic Heart Valves

Crimping

An objective of the initial crimp of the valve is to reduce the valve in its entirety to a diameter small enough to easily translate down to the native valve such as an aortic valve and still allow user visibility. This critical crimp diameter is typically 4 mm smaller than the native valve annulus size. So for a 19 mm valve, the valve should be crimped to minimally to about 15 mm. If the valve has components formed of Nitinol, the valve should be chilled prior to crimping so the valve can retain the reduced diametric geometry. The crimping of the valve could occur while the valve is either attached or detached from the delivery system. If the valve is attached to the delivery system, a guide may not be necessary to push the valve through a crimping funnel, for example, as the funnel could simply be pulled over the prosthetic valve; however, the guide serves the purpose of keeping crimping uniform.

Embodiments of crimping guides 800 and crimping funnels 900 are depicted in FIGS. 43-46. Referring now to FIG. 36 a crimping guide 800 has three arms (only two 810 820 are shown) 120° apart, which ensures the tabs of the valve are 120° apart during crimping. Extensions 812, 822 of arms form slots for receiving commissure posts of a prosthetic valve. The arms also include shoulders 814, 824 that are configured to abut with lower inflow portion of the prosthetic valve to retain prosthetic valve at a reproducible depth in the guide 800.

FIGS. 344A-B show a hinged funnel 900 being slid over guide 800 and prosthetic valve 20 to crimp the valve 20.

Figure 45:
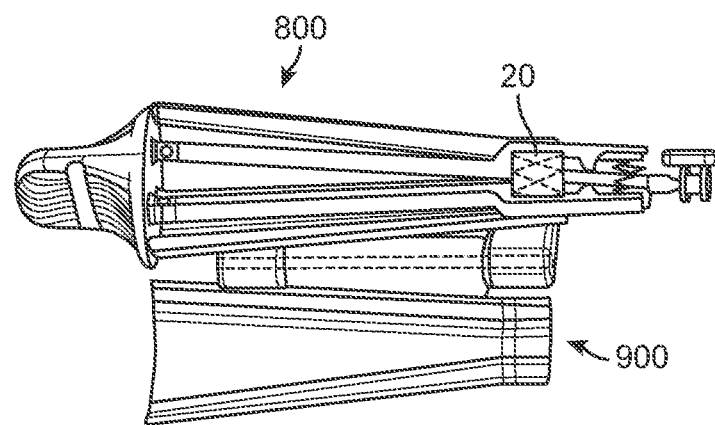
FIG. 45 is a schematic side view of embodiment of a crimping guide, an embodiment of a prosthetic valve, and an embodiment of a crimping funnel.

FIG. 45 shows an opened hinged funnel 900 containing guide 800 and crimped prosthetic valve 20.

Figure 46:
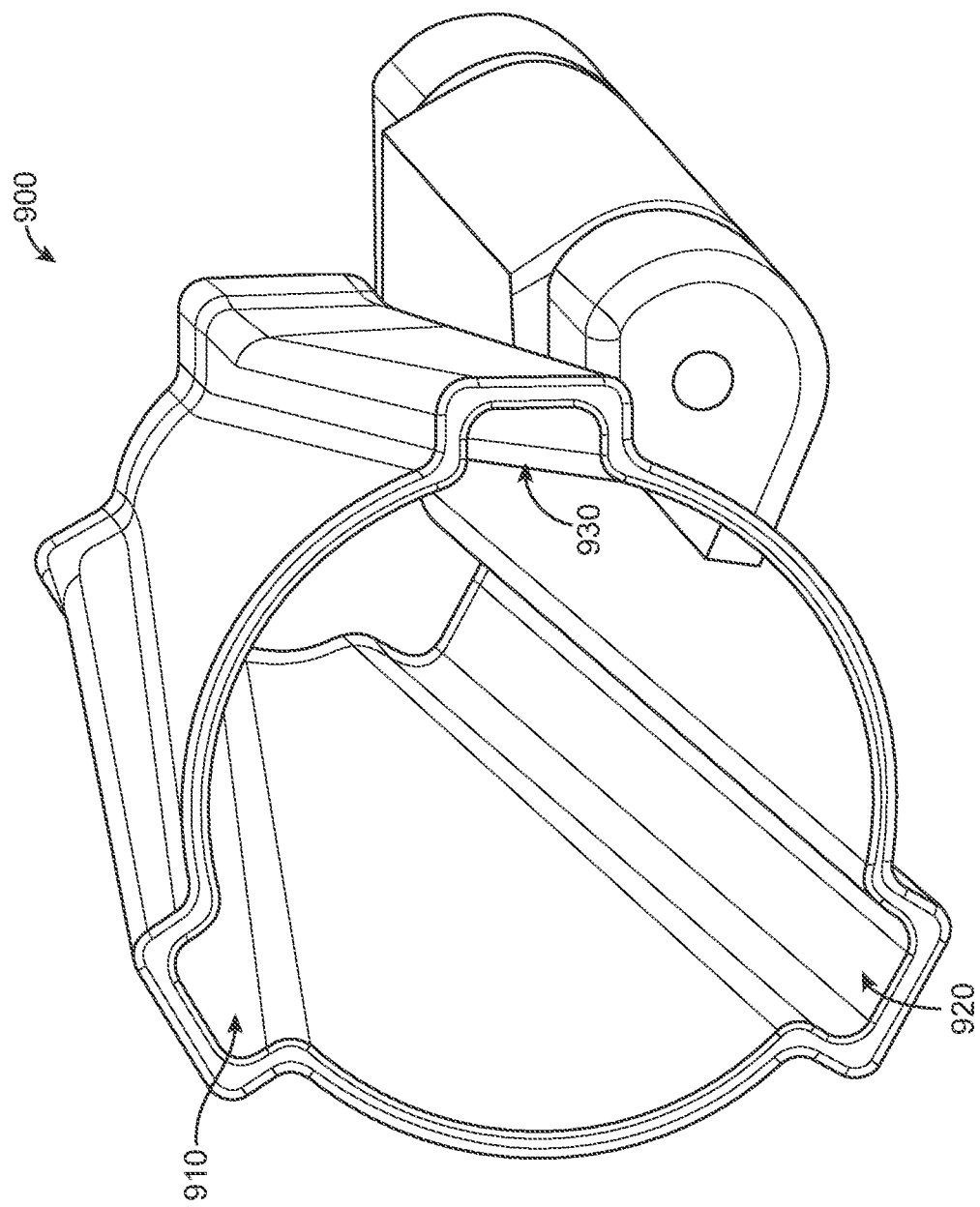
FIG. 46 is a perspective view of an embodiment of a crimping funnel.
Figures 47A, 47B, 47C, 47D, 47E:
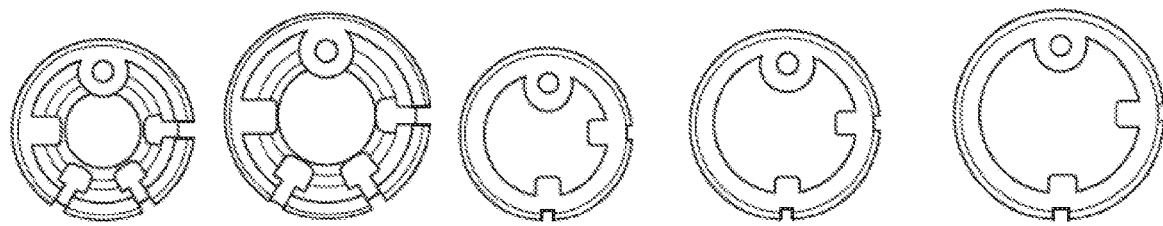
FIGS. 47A-47J, 48A-C, and 49-52 are schematic drawings of embodiments of sizers.
Figures 47F, 47G, 47H, 47I, 47J:
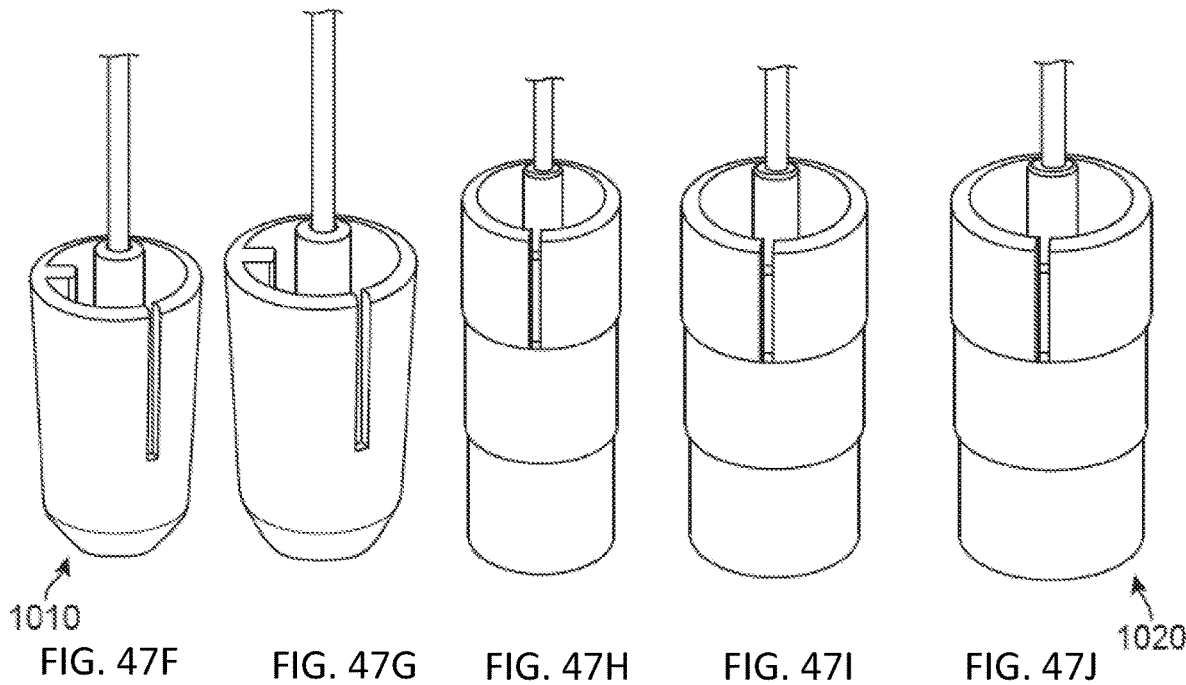

FIG. 46 illustrates an embodiment of a hinged funnel 900 that includes channels 910, 920, 930 for receiving arms of a crimping guide to ensure uniform and reproducible crimping results.

A similar crimping apparatus is shown in, and discussed with regard to, FIG. A93 of U.S. Provisional Patent Application No. 61/819,488, entitled SURGICAL HEART VALVES AND ASSOCIATED APPARATUSES, SYSTEMS AND METHODS, filed on May 3, 2013, which as indicated above is incorporated herein by reference to the extent that it does not conflict with the disclosure presented herein, is an alternative crimper contemplated herein.

An embodiment of a process for crimping is now described. The method includes the steps that follow. Of course other steps, variations, or omissions are contemplated. Drawings are shown, as indicated, to illustrate some of the steps. FIGS. A82-A92 of U.S. Provisional Patent Application No. 61/819,488 illustrate some of the steps of the method described below.
1) Rinse valve in separate sterile saline baths 3× (30 seconds each);
2) Chill valve in approx. 5° C. sterile saline ice bath (30 seconds);
3) Collect gathering suture with snare and pull gather suture through the rear of the delivery system handle;
4) Place valve in the conical reducer, aligning valve tabs with the reducer slots;
5) Place valve driver in the conical reducer, aligning the three driver prongs with the reducer slots;
6) Collect excess gathering suture (In embodiments, it may be important to NOT pull the valve into the conical reducer with the gather suture);
7) Advance valve until valve driver has advanced fully;
8) Collect excess gathering suture and press lock button on delivery system handle;
9) Remove valve driver from conical reducer;
10) Open the conical reducer's door and remove the delivery system with valve in the delivery system cone;
11) Manually seat the valve in the delivery system cone; and
12) Press the unlock button on the delivery system handle and collect excess gathering suture, and press the lock button on the delivery system handle when complete.

An embodiment of a process for re-crimping is now described. Recrimping prosthetic valve fully may be performed on the valve if the valve has not been deployed into the patient. If the valve has been deployed in the patient, recrimping fully is preferably not performed and the valve may be discarded. The method includes the following steps (Of course other steps, variations, or omissions are contemplated):
1) Place valve in warm saline bath (approx. 37° C.) for 10 seconds to expand the valve;
2) Place delivery system's delivery cone in the conical reducer and close the door; and confirm the latch is engaged;
3) Chill valve in approx. 5° C. sterile saline ice bath (30 seconds);
4) Collect gathering suture with snare and pull gather suture through the rear of the delivery system handle;
5) Place valve in the conical reducer, aligning valve tabs with the reducer slots;
6) Place valve driver in the conical reducer, aligning the three driver prongs with the reducer slots;
7) Collect excess gathering suture (In embodiments it may be important to NOT pull the valve into the conical reducer with the gather suture);
8) Advance valve until valve driver has advanced fully;
9) Collect excess gathering suture and press lock button on delivery system handle;
10) Remove valve driver from conical reducer;
11) Open the conical reducer's door and remove the delivery system with valve in the delivery system cone;
12) Manually seat the valve in the delivery system cone; and
13) Press the unlock button on the delivery system handle and collect excess gathering suture, and press the lock button on the delivery system handle when complete.

Other crimping apparatus are contemplated herein. For example, the iris crimper illustrated in FIG. A60 of U.S. Provisional Patent Application No. 61/819,488.

Sizers

Various aortic valve sizer instruments that facilitate accurate valve size determination for sutureless aortic valve implantation procedures are disclosed herein.

Shown below in FIGS. 47A-J are sizer concepts that features multiple diameters on a single sizer head. One configuration 1010 has a constant taper with a marker at each 1 mm diameter increment, while another 1020 has vertical walls with a step at each diameter transition. The later configuration provides tactile feel between each size. Markers are placed within the sizer at the level of the transition, allowing one to know the diameter based on the depth of the sizer. The markings face the user. This configuration has just three sizes, but less or more sizes could be placed on each sizer head.

Figures 48A, 48B, 48C:
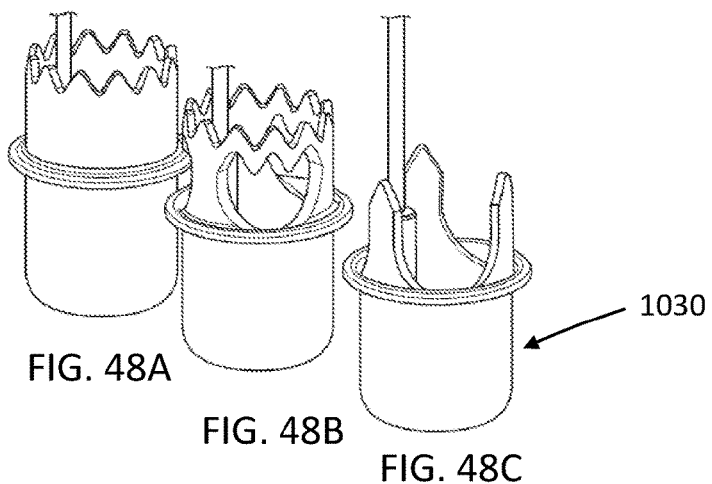

Shown in FIGS. 48A-C are various sizer heads that encompass geometry that replicates or approximates key features of the prosthesis to aid a surgeon in selecting the appropriate sized prosthesis. In the depicted embodiments, a flange is present which mimics the geometry of the prosthesis inflow cuff. The top portion of the cuff is mimicked as the insertion of the sizer into the aortic valve annulus generally would not be possible if the bottom flange were also present. The actual geometry of replica cuff would attempt to mimic the geometry of the prosthesis cuff as it would be in the actual anatomy, which may be angled in slightly due to the elastic properties of nitinol. Additionally, some interference may be designed into the cuff geometry or lower barrel on the sizer to simulate the radial force that the valve would have on the annulus.

The outflow portion of the replica sizer head mimics or approximates the height and geometric features of the prosthesis. Gaps could be placed between the leaflet commissures on the sizer head to illustrate the area that is accessible via catheter for coronary stent procedures (the only area inaccessible to a catheter for coronary stent procedure may be at the valve commissures). Alternatively, lines could be printed on the outflow portion of the sizer indicating the stent and leaflet geometry (not shown). Bullet tips are shown below, though a standard cylinder at the inflow end of the sizer is also considered.

Go/No-Go Sizer Head

Figure 49:
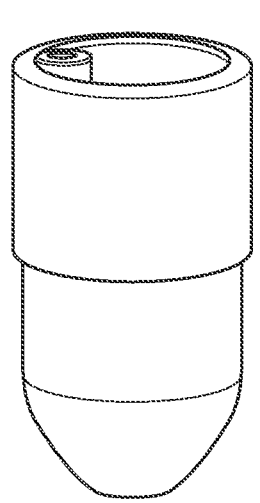

A go/no-go sizer 1040 FIG. 49, has been contemplated that allows a surgeon to select a prosthesis size by process of elimination. The sizer has a distal end portion of a diameter smaller than the sizer and a proximal end portion the size of the sizer. By way of example and for a size 23 mm sizer, the distal end of the sizer may have a diameter of 22 mm and the proximal end may have a diameter of 23 mm. Likewise, for a 25 mm sizer, the distal end of the sizer may have a diameter of 24 mm and the proximal end may have a diameter of 26 mm.

When using the sizer, the surgeon would insert sequentially larger sizers until the proximal end of the sizer does not comfortably pass through the aortic valve annulus. The appropriate prosthesis would then be equal to the smallest sizer with the proximal end that would not pass.

Figure 50:
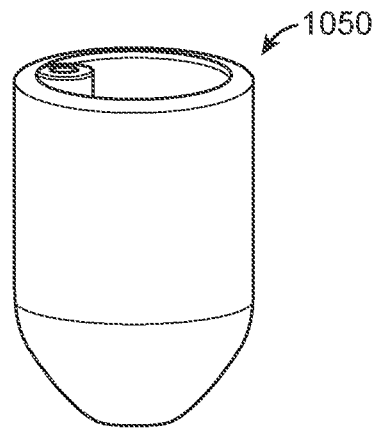

Another version of this go/no-go sizer 1050, FIG. 50, could have a continuous taper rather than a step between the two diameters on the sizer head.

To facilitate easier insertion of the sizer head into the annulus a bullet tipped sizer head is contemplated herein, where the geometry is designed to mimic hegar sizers. The difference between a hegar sizer and this aortic valve sizer is that this sizer will have transparent walls and will be shorter in overall length.

A self-expanding sizer has also been contemplated herein in. To give the user a feel for what the self-expanding prosthesis would actually feel like, an elastic replica component is contemplated that would deploy into the annulus and provide identical force representation of the actual valve prosthesis. This component could simply be a duplicate of the valve frame or could be of a less expensive alternative material such as plastic or spring steel.

Figure 51:
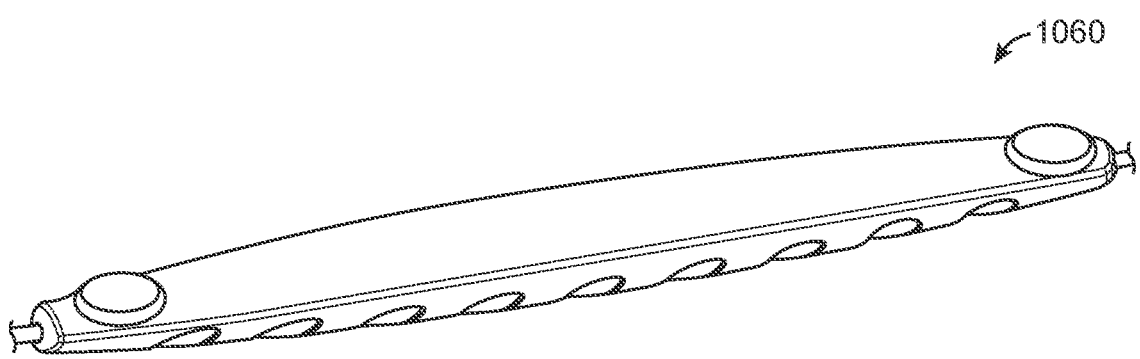
Figure 52:
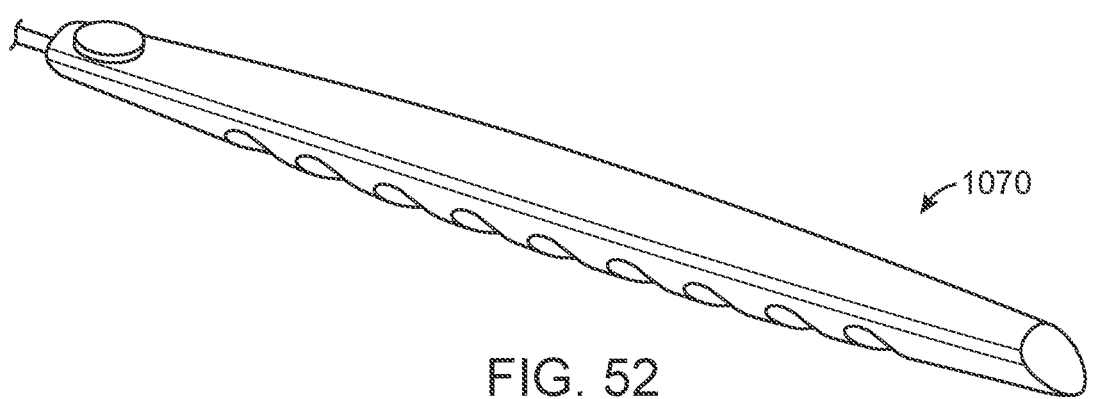

Double ended sizer handle 1060, FIG. 51, and single ended sizer handle 1070, FIG. 52, are also contemplated herein. For a single ended sizer handle, by having the size etched on the end facing the user, the user may much more easily see the size of the sizer during sizing (FIGS. 51-52). Similarly, a ramp like feature could be added to the double ended sizer to achieve the same affect (not shown).

Additional Delivery Systems

Some additional embodiments of delivery systems that may be used to deliver prosthetic valves are provided below.

In some embodiments a delivery tool includes a rotary shaft. The delivery tool preferably allows a prosthetic valve to be delivered, deployed, recaptured, and repeated as necessary. In various embodiments the delivery tools have a rotatable shaft that controls constriction and expansion of a self-expanding prosthetic valve. Turning in one direction constricts the prosthetic valve, while turning in the other direction allows for controlled expansion of the prosthetic valve.

Figure 53:
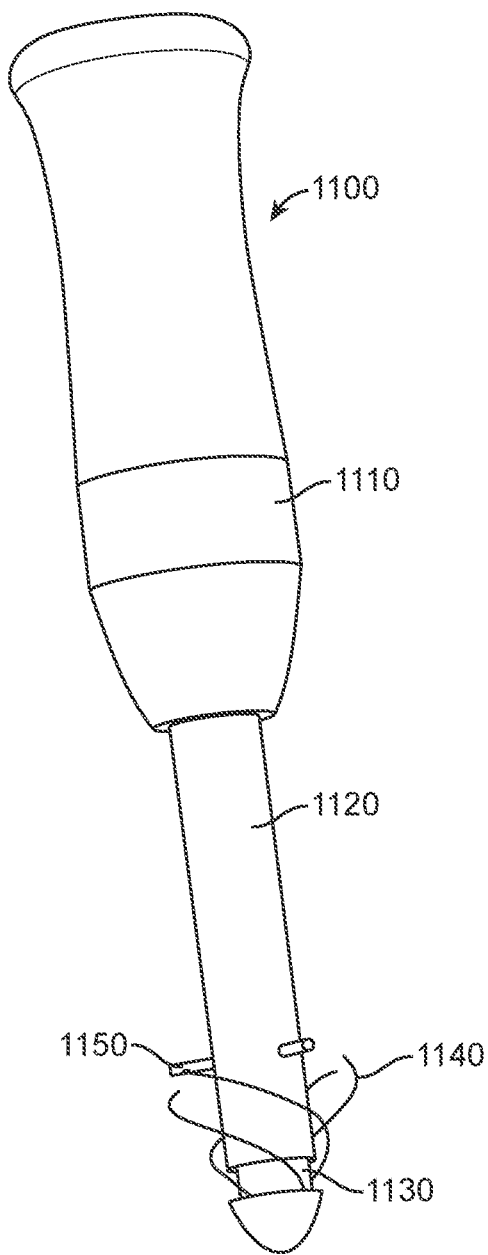
FIGS. 53-73 and 74A-B are schematic drawings illustrating some embodiments of prosthesis delivery systems.

Referring now to FIG. 53, an embodiment of a delivery tool having a rotary shaft is depicted. The tool has a handle 1100 and stationary shaft 1120. The handle includes a rotatable ring actuator 1110 that is coupled to a rotary shaft 130 disposed within at least a portion of stationary shaft 1100. The ring 1100 can be turned clockwise or counter-clockwise to cause rotary shaft 1130 to rotate clockwise or counterclockwise. Posts 1150 may be connected to stationary shaft 1120. Posts 1150 are positioned and configured to retain a prosthetic valve and prevent the valve from rotating when the tool is used to constrict or expand the valve. The tool further includes coil arms 1140 configured to be attached to the prosthetic valve. The coil arms 1140 are coupled to the rotary shaft 1130.

The tool depicted in FIG. 53 can be used as follows. A prosthetic valve (not shown in FIG. 53) may be slid over the distal end of the tool. The coil arms 1140 can then be hooked onto the valve. The valve may be held in place as the actuator ring 1100 is twisted to allow the prosthetic valve drop into posts 1150, which constrain the valve from rotational movement and lets the arms 1140 pull the valve inward as they twist and pull tight. The actuator ring 1110 can continued to be turned, causing the rotary shaft 1130 to twists coil arms 1140. Arms 1140 are hooked on the valve, and the valve is not able to move due to post 1150. Twisting will cause arms 1140 to pull tight, compressing the valve to a loaded position.

The delivery system can then be placed into the patient. A safety unlock may be pressed while turning the actuator ring 1110 to release the valve. The position of the valve may be checked. If the position is unacceptable, the valve may be recaptured recapture by twisting actuator ring 1110 to tighten the coils 1140. If the position of the valve is acceptable, the coils 1140 can then be freed from the valve by disengaging the hook manually.

Figure 54A:
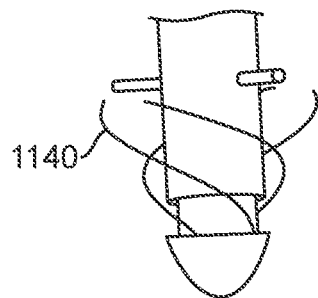
Figure 54B:
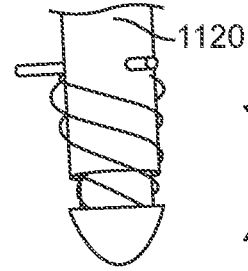
Figure 54C:
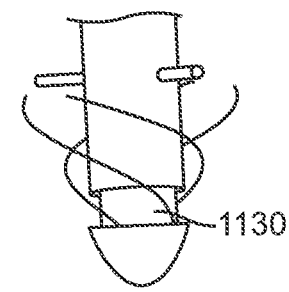

FIGS. 54A-C show a sequence of rotating to tighten (FIG. 54A to FIG. 54B) and loosen (FIG. 54B to FIG. 54C) coil arms (valve not shown).

Figure 55:
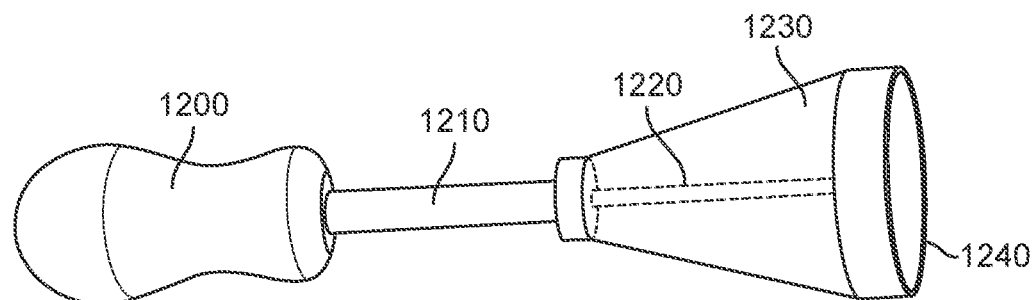

In some embodiments, a delivery tool includes a jubilee clip type that can be expanded and collapsed by rotating a handle. Referring now to FIG. 55 an embodiment of such a tool is shown. The tool includes a handle 1200, stationary shaft 1210, rotary shaft 1220, cone 1230 and band 1240. When the handle 1200 is turned, rotatable shaft 1220 turns causing cone 1230 to expand or constrict band 1240. A valve may be placed within band 1240.

Figure 56:
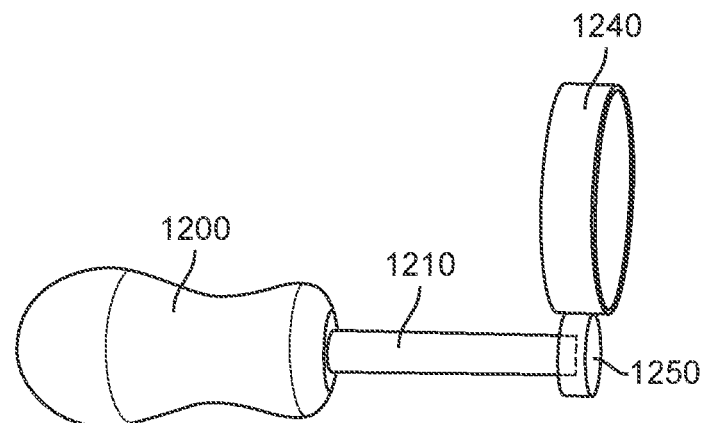

Referring now to FIG. 56, another embodiment of a jubilee clip type device is shown. The device includes a handle 1200, shaft 1210, screw mechanism 1250, and band 1240. Turning handle 1200 causes shaft 1210 to turn, thereby actuating screw mechanism 1250 to constrict or expand band 1240.

Figure 57:
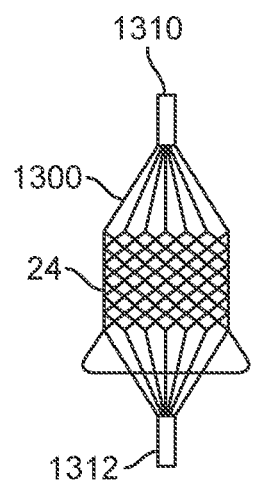
Figure 58:
Figure 59:
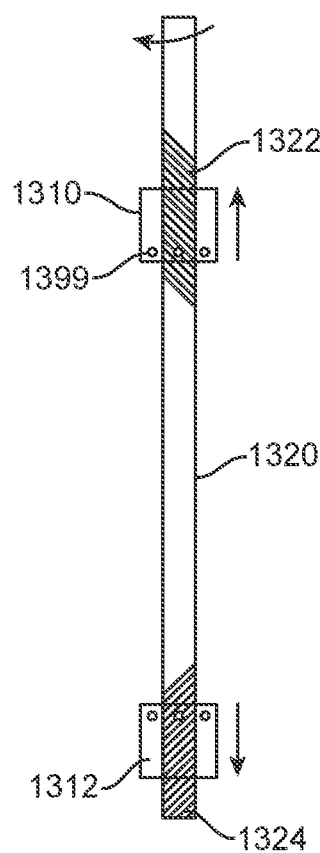
Figure 60:
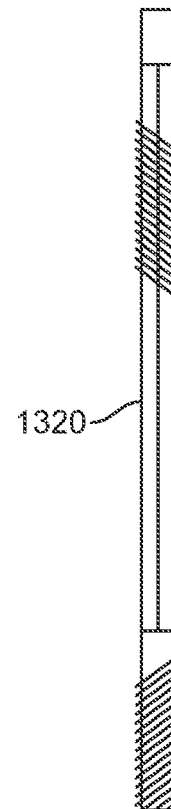
Figure 61:
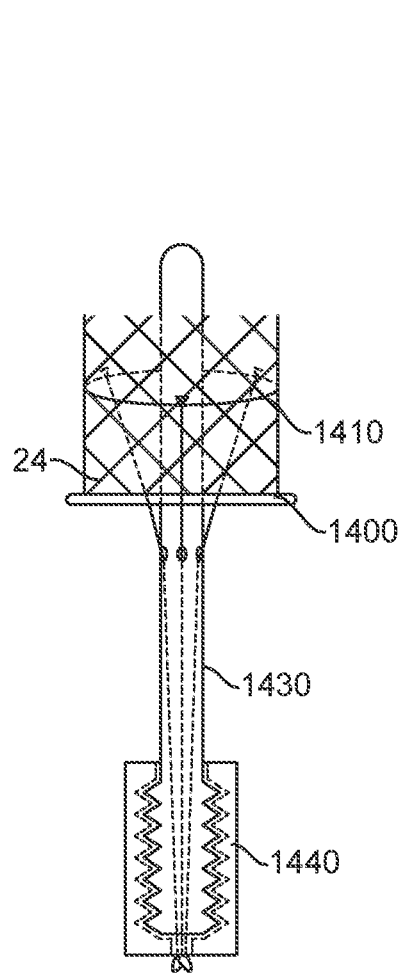
Figure 62:
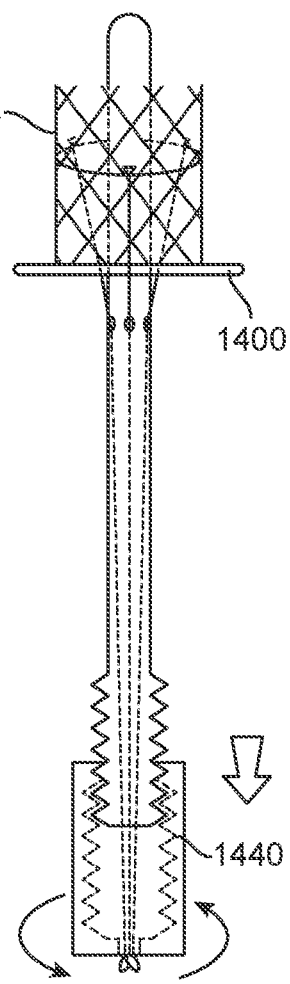
Figure 63:
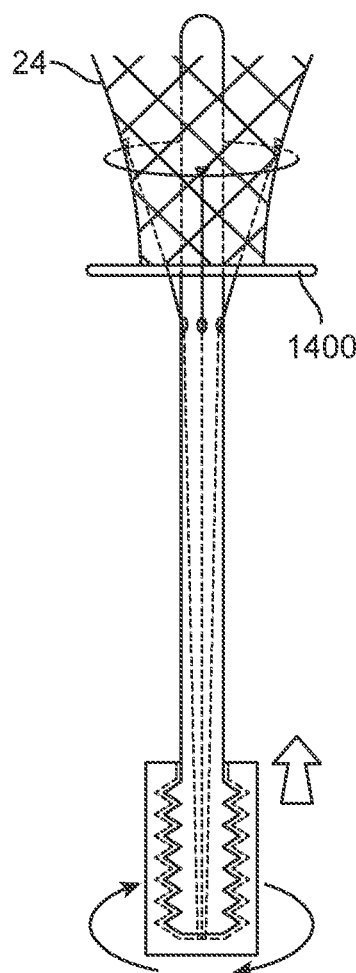
Figure 64:
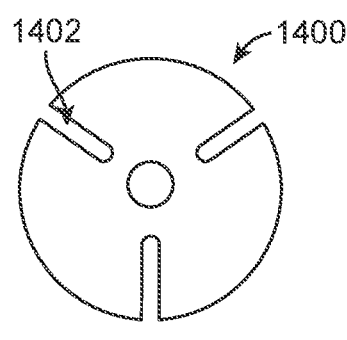

In some embodiments, a shaft of s delivery tool lengthens or shortens to increase or decrease tension on a frame of a prosthetic valve to constrict or expand the prosthetic valve. Referring now to FIGS. 57-59, an embodiment of such a tool is shown. The tool includes tethers 1300 attached to frame 24 of device at inflow and outflow ends. The tethers 1300 are connected to internally threaded elements 1310, 1312. Element 1310 is threaded in the opposite direction as element 1312. A shaft 1320 has first threads 1322 and second threads 1324 spaced apart from the first threads 1322. The threads 1322, 1324 are configured to engage internally threaded elements 1310, 1312 such that rotation of shaft caused the distance between elements 1310, 1312 to increase or decrease depending on the direction that the shaft is rotated. As depicted in FIG. 59, internally threaded elements 1310, 1320 may include fixation bars 1399 to ensure movement of the threaded elements and prevent them from rotating with the shaft. The fixation bars 1399 can extend and collapse with the movement of the threaded features. FIG. 60 shows and embodiment with two movements with two shafts.

Figure 65:
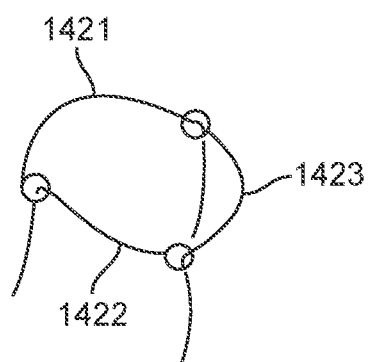

In some embodiments, a delivery tool includes a rotatable element to which sutures are connected. The sutures may be connected to a frame a prosthetic valve. When the element is rotated, the sutures tighten or loosen around the frame to control constriction and expansion of the prosthetic valve. An example such a system is depicted in FIGS. 61-64. The device includes a collar 1400 on which the prosthesis may sit. The collar may be clear or could be removable. One or more sutures 1410 may be placed around at least a portion of frame 24 of device. Sutures 1410 may pass through slots 1402 in collar 1400 and down through handle 1430 and connected to rotatable actuator element 1440. Rotatable actuator element 1440 and at least a portion of handle 1430 are complementarily threaded. Rotation of element 1440 in one direction causes the distance between element 1440 and prosthesis to increase and causes frame 24 to constrict. Rotation of element 1440 in the opposite direction causes the distance between element 1440 and prosthesis to decrease and allows frame 24 to expand. FIG. 65 shows interconnected sutures that 1421, 1422, 1423 that may be employed with a system depicted in FIGS. 61-64.

In some embodiments, a control arms delivery system is employed to deliver a self-expanding prosthetic device. Preferably, the system allows for deployment, recapture and repeat, as necessary. In some embodiments, a user controls a sliding sheath to cause control arms to mover radially in or out, which causes the prosthesis to constrict or expand. In some embodiments, the delivery system includes hooks, which may be triangular, that clasp into a frame of a prosthesis naturally when in tension and can be released by pushing forward when the prosthesis is expanded. In some embodiments, a delivery has two shafts that control the inflow and outflow of a prosthetic valve separately, so that a user can deploy the inflow to check the seating. After visibly checking the positioning, the user can recollapse and reposition if needed or actuate the second shaft to fully expand the valve and push forward to disengage.

Figure 66:
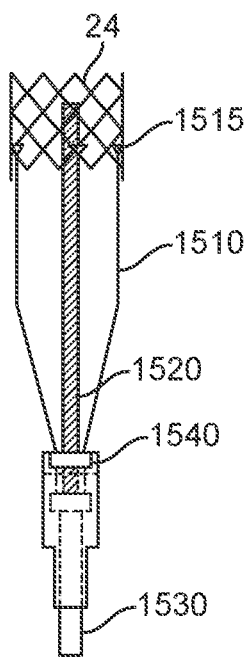
Figure 67:
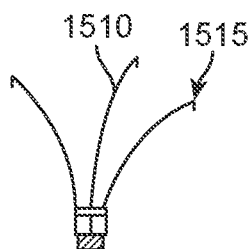
Figure 68:
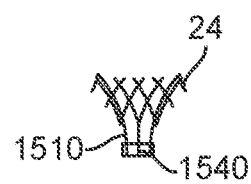
Figure 69:
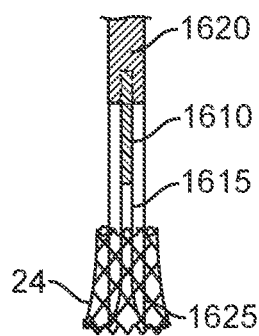
Figure 70:
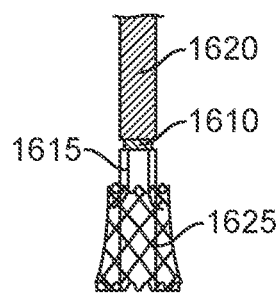
Figure 71:
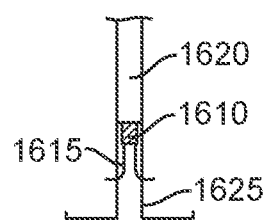
Figure 72:
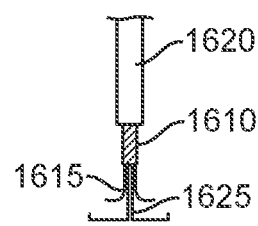

Referring now to FIGS. 66-68, an embodiment of a control arm delivery system is depicted. The system includes a handle 1530, a slide ring 1540, control arms 1510 coupled to handle 1530, and shaft 1520 connected to handle 1530. Control arms 1510 include hooks 1515 that may be triangular and interact with frame 24 of prosthesis. Control arms 1510 are naturally flared outward and are shaped such that sliding of ring 1540 upward cause arms 1510 to move inwardly, thereby constricting frame 24.

Referring now to FIGS. 69-72, an embodiment of a control arm delivery system is depicted in which an inflow and outflow of a frame 24 of a prosthetic valve may be independently controllable. The delivery system includes an outer shaft 1620 advanceable over outer control arms 1625, which may be control arms as described above with regard to FIGS. 66-68. The delivery system further includes an inner shaft 1610 advanceable over inner control arms 1615, which may be control arms as described above with regard to FIGS. 66-68. Control arms 1625 may be connected to an inflow portion of frame 24. Control arms 1615 may be connected to an outflow portion of frame 24. The inner shaft 1610 may be pushed down over control arms 1615 to cause the arms to move inwardly, causing the outflow portion of frame 24 to constrict. The outer shaft 1620 may be pushed down over control arms 1625 to cause the arms to move inwardly, causing the inflow portion of frame 24 to constrict.

Figure 73:
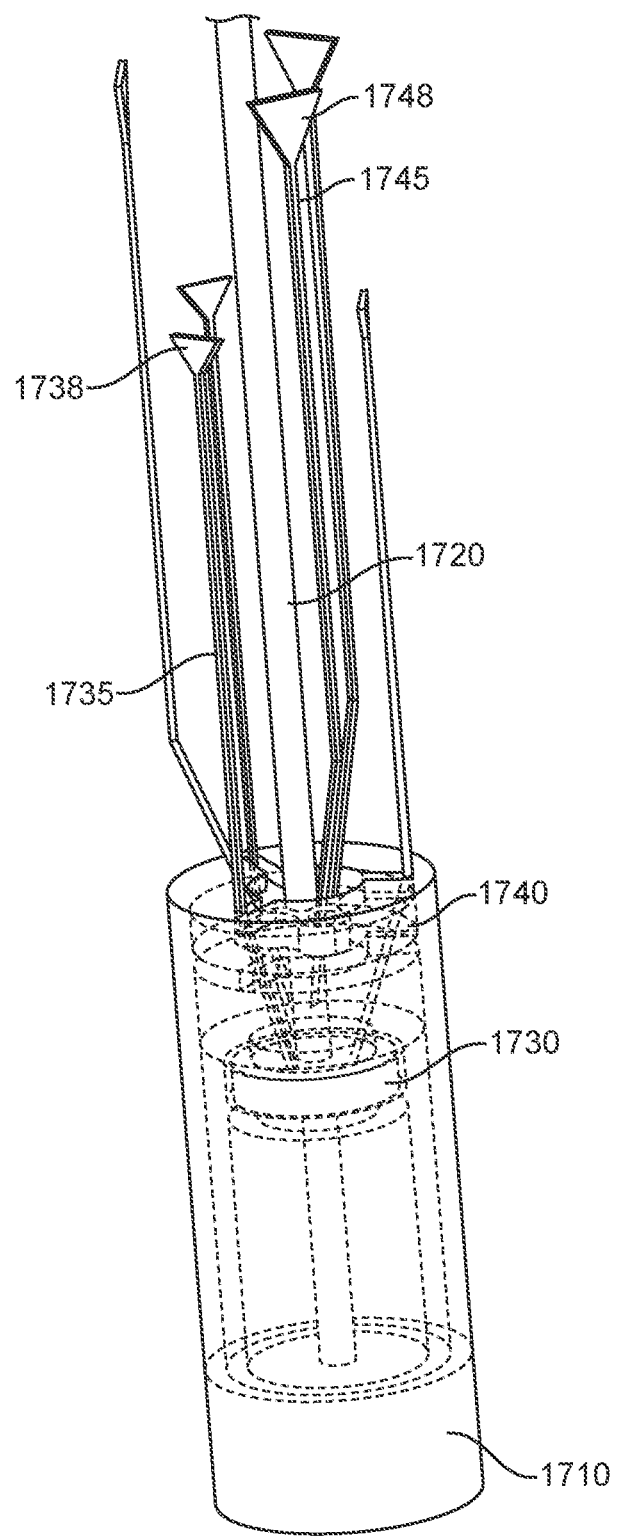

Referring now to FIG. 73 an embodiment of a control arm delivery system is depicted. The delivery system includes a stationary handle 1710 and rod 1720 attached to handle 1710, an inner outflow control arm actuator 1730 (such as a sliding ring) and an outer inflow control arm actuator 1740 (such as sliding ring) and outflow 1735 and inflow 1745 control arms. Outflow control arms 1735 include hooks 1738, and inflow control arms 1745 include hooks 1748. Hooks 1738, 1748 are triangular and lock naturally into a frame of a prosthetic valve. Hooks 1738, 1748 stay locked when the frame is collapsed, but when the frame is expanded and the delivery system is pushed forward the hooks will naturally pop out. When the inflow actuator 1740 is fully retracted (closer to handle 1710), the inflow portion of frame is expanded. When the inflow actuator 1740 is fully advances (further from handle 1710), the inflow portion of frame is constricted. When the outflow actuator 1730 is fully retracted (closer to handle 1710), the outflow portion of frame is expanded. When the outflow actuator 1730 is fully advances (further from handle 1710), the outflow portion of frame is constricted. The inflow and outflow portions of a frame of a prosthetic valve may be independently controlled.

Figure 74A:
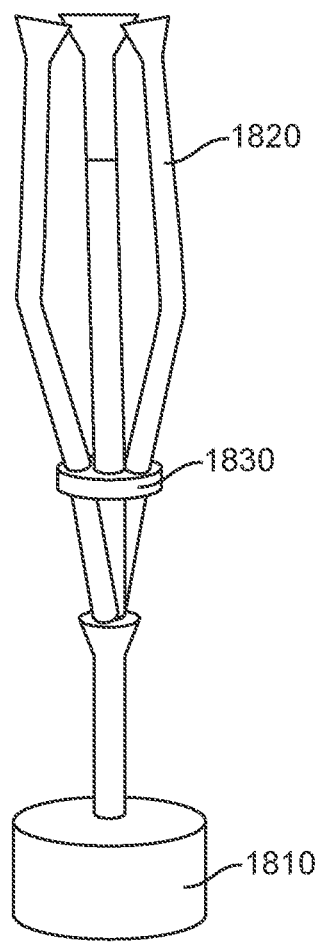
Figure 74B:
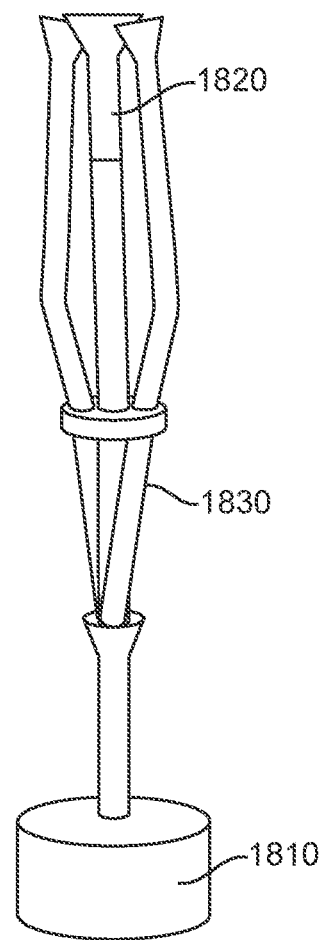

Referring now to FIGS. 74A-B, drawings of an embodiment of a prototype control arm delivery system is shown. The delivery system includes a handle 1810, control arms 1820 and actuation ring 1830. As ring 1830 is advanced over arms 1830, arms 1840 move inwardly (compare FIG. 74A to FIG. 74B).

Definitions

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like.

Summary of Some Select Embodiments

A number of embodiments of devices, systems, and methods are described herein. A summary of some aspects of some embodiments described above are presented below.

In a first aspect, a system includes a medical device for implanting in a valve of a subject. The implantable medical device has a self-expanding frame (such as a prosthetic heart valve frame), and a holder configured to retain the frame of the implantable medical device in a constricted configuration and to control expansion of the frame. The holder comprises a first controllably constrictable and expandable loop, wherein the first loop is disposed about at least a portion of the self-expanding frame such that constriction or expansion of the first loop controls constriction or expansion of the frame.

A second aspect is a system according to the first aspect wherein the frame comprises an inflow region, wherein the inflow region comprises an upper portion and a lower portion, and wherein the first loop is disposed about at least a portion of the upper portion of the inflow region of the frame such that constriction or expansion of the first loop controls constriction or expansion of the upper portion of the inflow region of the frame.

A third aspect is a system according to the second aspect wherein the holder comprises a second controllably constrictable and expandable loop, wherein the second loop is disposed about at least a portion of the lower portion of the inflow region of the frame such that constriction or expansion of the second loop controls constriction or expansion of the lower portion of the inflow region of the frame.

A fourth aspect is a system according the third aspect wherein the first and second loop are independently controllably constrictable and expandable.

A fifth aspect is a system according the third aspect, wherein the frame comprises an outflow region and wherein the holder comprises a third controllably constrictable and expandable loop, wherein the third loop is disposed about at least a portion of the outflow region of the frame such that constriction or expansion of the third loop controls constriction or expansion of at least a portion of the outflow region of the frame.

A sixth aspect is a system according to the fifth aspect, wherein the first loop is independently controllably constrictable and expandable relative to the second and third loops.

A seventh aspect is a system according to the sixth aspect, wherein the second and third loops are together controllably constrictable and expandable.

An eighth aspect is a system according to the sixth aspect wherein the first loop is a portion of a first cord, wherein the second loop is a portion of a second cord, wherein the third loop is a portion of a third cord, wherein the holder comprises a first extension member having a first opening, a second opening and a conduit between the first and second openings, wherein the holder comprises a second extension member having a first opening, a second opening and a conduit between the first and second openings, wherein a portion of the first cord extends through the conduit of the first extension member, and wherein a portion of the second and third cords extend through the conduit of the second extension member.

A ninth aspect is a system according to the eighth aspect, wherein the frame has a longitudinal axis and wherein the holder is configured such that the first and second extension members are offset from the longitudinal axis of the frame and are substantially parallel to the longitudinal axis of the frame when the holder constricts the frame or retains the frame in a constricted configuration.

A tenth aspect is a system according to the ninth aspect, wherein the first and second extension members are positioned external to the frame when the holder constricts the frame or retains the frame in a constricted configuration.

An eleventh aspect is a system according to the eighth aspect, wherein the first cord comprises a suture forming the first loop and a tether attached to an end of the suture, wherein the second cord comprises a suture forming the second loop and a tether attached to an end of the suture, and wherein the third cord comprises a suture forming the third loop and a tether attached to an end of the suture.

A twelfth aspect is a system according to the eighth aspect, wherein the holder comprises an adapter configured to cooperatively mate with a shaft, where the adaptor comprises first and second lumens extending through the adaptor, and wherein a portion of the first cord extends through the first lumen such that an end of the first cord extends beyond the adaptor and wherein a portion of the second cord extends through the second lumen such that an end of the second cord extends beyond the adaptor.

A thirteenth aspect is a system according to the twelfth aspect, further comprising the shaft, wherein the shaft defines one or more lumens through the shaft, wherein the shaft is configured to couple to the adaptor of the holder, and wherein a portion of the first cord extends through one of the one or more lumens of the shaft such that an end of the first cord extends beyond the shaft and wherein a portion of the second cord extends through one of the one or more lumens of the shaft such that an end of the second cord extends beyond the adaptor, wherein the portions of the first and second cords extend through the same lumen or different lumens of the shaft.

A fourteenth aspect is a system according to the thirteenth aspect, further comprising a handle operably coupled to, or operably couplable to, the shaft.

A fifteenth aspect is a system according to the fourteenth aspect, wherein the handle comprises a first actuation element operably couplable to the end of the first cord such that constriction and expansion of the first loop is controllable via the first actuation element.

A sixteenth aspect is a system according to the fifteenth aspect, wherein the handle comprises a second actuation element operably couplable to the end of the second cord such that constriction and expansion of the second loop is controllable via the second actuation element.

A seventeenth aspect is a system according to the sixteenth aspect, wherein the second actuation element is operably couplable to the end of the third cord such that constriction and expansion of the third loop is controllable via the second actuation element.

An eighteenth aspect is a system according to the fifteenth aspect, further comprises a control unit tethered to the handle, wherein the control until comprises an actuation element operably couplable to the end of the second cord such that constriction and expansion of the second loop is controllable via the control unit actuation element.

A nineteenth aspect is a system according to the fourteenth aspect, further comprising a control unit operably coupled to the handle, wherein the control unit comprises a first actuation element operably couplable to the end of the first cord such that constriction and expansion of the first loop is controllable via the first actuation element.

A twentieth aspect is a system according to the nineteenth aspect, wherein the control unit comprises a second actuation element operably couplable to the end of the second cord such that constriction and expansion of the second loop is controllable via the second actuation element.

A twenty-first aspect is a system according to the twentieth aspect, wherein the second actuation element is operably couplable to the end of the third cord such that constriction and expansion of the third loop is controllable via the second actuation element.

A twenty-second aspect is a system according to the first aspect, wherein the holder further comprises a second controllably constrictable and expandable loop, wherein the second loop is disposed about at least a portion of the self-expanding frame such that constriction or expansion of the first loop controls constriction or expansion of the frame.

A twenty-third aspect is a system according to the twenty-second, wherein the holder further comprises a third controllably constrictable and expandable loop, wherein the third loop is disposed about at least a portion of the self-expanding frame such that constriction or expansion of the first loop controls constriction or expansion of the frame.

A twenty-fourth aspect is a system according to the twenty-third aspect, wherein the first, second, and third loops together are disposed about a circumference of the frame.

A twenty-fifth aspect is a system according to the twenty-third aspect, wherein constriction and expansion of the first, second and third loops are independently controllable.

A twenty-sixth aspect is a system according to the twenty-third aspect, wherein constriction and expansion of the first loop is independently controllable relative to the second and third loops, wherein constriction and expansion of the second and third loops are controlled together.

A $27^{th}$ aspect is a system according to the $22^{nd}$ aspect, wherein the first loop is a portion of a first cord, wherein the second loop is a portion of a second cord, and wherein the holder comprises a first extension member having a first opening, a second opening and a conduit between the first and second openings, wherein the holder comprises a second extension member having a first opening, a second opening and a conduit between the first and second openings, wherein a portion of the first cord extends through the conduit of the first extension member, and wherein a portion of the second cord extend through the conduit of second extension member.

A $28^{th}$ aspect is a system according to the $27^{th}$ aspect, wherein the frame has a longitudinal axis and wherein the holder is configured such that the first and second extension members are offset from the longitudinal axis of the frame and are substantially parallel to the longitudinal axis of the frame when the holder constricts the frame or retains the frame in a constricted configuration.

A $29^{th}$ aspect is a system according to the $28^{th}$ aspect, wherein the first and second extension members are positioned external to the frame when the holder constricts the frame or retains the frame in a constricted configuration.

A $30^{th}$ aspect is a system according to the $23^{rd}$ aspect, wherein the first loop is a portion of a first cord, wherein the second loop is a portion of a second cord, wherein the third loop is a portion of a third cord, wherein the holder comprises a first extension member having a first opening, a second opening, and a conduit between the first and second openings, wherein the holder comprises a second extension member having a first opening, a second opening, and a conduit between the first and second openings, wherein the holder comprises a third extension member having a first opening, a second opening, and a conduit between the first opening and the second opening, and wherein a portion of the first cord extends through the conduit of the first extension member, a portion of the second cord extends through the conduit of the second extension member, and a portion of the third cord extend through the conduit of third extension member.

A $31^{st}$ aspect is a system according to the $30^{th}$ aspect, wherein the frame has a longitudinal axis and wherein the holder is configured such that the first, second, and third members extend into a central opening of the frame at an angle relative to the longitudinal axis of the frame when the frame is expanded.

A $32^{nd}$ aspect is a system according to the $1^{st}$ aspect, wherein the frame has a longitudinal axis, wherein the holder further comprises an extension member having a first opening, a second opening, and a conduit between the first and second openings, wherein the first loop is part of a first cord and wherein a portion of the first cord extends through the conduit of the extension member, and wherein the holder is configured such that the extension member is offset from the longitudinal axis of the frame and is substantially parallel to the longitudinal axis of the frame when the holder constricts the frame or retains the frame in a constricted configuration.

A $33^{rd}$ aspect is a system according to the $32^{nd}$ aspect, wherein the holder is configured such that the extension member is positioned external to the frame when the holder constricts the frame or retains the frame in a constricted configuration.

A $34^{th}$ aspect is a delivery system for implanting a medical device having a self-expanding frame in a valve sinus of a subject. The delivery system includes a holder configured to retain the frame of the implantable medical device in a constricted configuration and to control expansion of the frame. The holder comprises a first controllably constrictable and expandable loop configured to be disposed about at least a portion of the self-expanding frame such that constriction or expansion of the first loop controls constriction or expansion of the frame.

A $35^{th}$ aspect is a system according to the $34^{th}$ aspect, wherein the holder comprises a second controllably constrictable and expandable loop configured to be disposed about at least a portion of the self-expanding frame such that constriction or expansion of the second loop controls constriction or expansion of the lower portion of the inflow region of the frame.

A $36^{th}$ aspect is a system according to the $35^{th}$ aspect, wherein the first and second loop are independently controllably constrictable and expandable.

A $37^{th}$ aspect is a system according to the $35^{th}$ aspect, wherein the first loop is a portion of a first cord, wherein the second loop is a portion of a second cord, wherein the holder comprises a first extension member having a first opening, a second opening, and a conduit between the first and second openings, wherein the holder comprises a second extension member having a first opening, a second opening, and a conduit between the first and second openings, wherein a portion of the first cord extends through the conduit of the first extension member and wherein a portion of the second and third cords extend through the conduit of the second extension member.

A $38^{th}$ aspect is a system according to the $37^{th}$ aspect, wherein the first and second extension members are configured to be offset from a longitudinal axis of the frame and are configured to be substantially parallel to the longitudinal axis of the frame when the holder constricts the frame or retains the frame in a constricted configuration.

A $39^{th}$ aspect is a system according to the $38^{th}$ aspect, wherein the first and second extension members are positioned external to the frame when the holder constricts the frame or retains the frame in a constricted configuration.

A $40^{th}$ aspect is a system according to the $37^{th}$ aspect, wherein the holder is configured such that first, second, and third members are configured to extend into a central opening of the frame at an angle relative to a longitudinal axis of the frame when the frame is expanded.

A $41^{st}$ aspect is a system according to the $37^{th}$ aspect, wherein the holder comprises an adapter configured to cooperatively mate with a shaft, where the adaptor comprises first and second lumens extending through the adaptor, and wherein a portion of the first cord extends through the first lumen such that an end of the first cord extends beyond the adaptor and wherein a portion of the second cord extends through the second lumen such that an end of the second cord extends beyond the adaptor.

A $42^{nd}$ aspect is a system according to the $41^{st}$ aspect, further comprising the shaft, wherein the shaft defines one or more lumens through the shaft, wherein the shaft is configured to couple to the adaptor of the holder, and wherein a portion of the first cord extends through one of the one or more lumens of the shaft such that an end of the first cord extends beyond the shaft and wherein a portion of the second cord extends through one of the one or more lumens of the shaft such that an end of the second cord extends beyond the adaptor, wherein the portions of the first and second cords extend through the same lumen or different lumens of the shaft.

A $43^{rd}$ aspect is a system according to the $42^{nd}$ aspect, further comprising a handle operably coupled to, or operably couplable to, the shaft.

A $44^{th}$ aspect is a system according to the $43^{rd}$ aspect, wherein the handle comprises a first actuation element operably couplable to the end of the first cord such that constriction and expansion of the first loop is controllable via the first actuation element.

A $45^{th}$ aspect is a system according to the $44^{th}$ aspect, wherein the handle comprises a second actuation element operably couplable to the end of the second cord such that constriction and expansion of the second loop is controllable via the second actuation element.

A $46^{th}$ aspect is a system according to the $43^{rd}$ aspect, further comprising a control unit operably coupled to the handle, wherein the control unit comprises a first actuation element operably couplable to the end of the first cord such that constriction and expansion of the first loop is controllable via the first actuation element.

A $47^{th}$ aspect is a system according to the $34^{th}$ aspect, wherein the holder further comprises an extension member having a first opening, a second opening, and a conduit between the first and second openings, wherein the first loop is part of a first cord and wherein a portion of the first cord extends through the conduit of the extension member, and wherein the holder is configured such that the extension member is offset from a longitudinal axis of the frame and is substantially parallel to the longitudinal axis of the frame when the holder constricts the frame or retains the frame in a constricted configuration.

A $48^{th}$ aspect is a system according to the $47^{th}$ aspect, wherein the holder is configured such that the extension member is positioned external to the frame when the holder constricts the frame or retains the frame in a constricted configuration.

A $49^{th}$ aspect is a method for implanting a medical device having a self-expanding frame in a valve of a patient. The method includes inserting the device into the valve annulus of the patient, wherein the frame is in a constricted configuration; and expanding a loop disposed around at least a portion of the frame to allow the frame to expand to cause at least a portion of the device to engage at least a portion of the native valve annulus.

A $50^{th}$ aspect is a method according to the $49^{th}$ aspect, wherein the device is a prosthetic heart valve and wherein the self-expandable frame comprises an inflow region of the prosthetic heart valve, wherein the inflow region comprises an upper portion and a lower portion, and wherein the loop is disposed about at least a portion of the upper portion of the inflow region of the frame such that expansion of the loop allows the upper portion of the inflow region of the frame to expand.

A $51^{st}$ aspect is a method according to the $49^{th}$ aspect, wherein the loop is in the form of a cinch suture.

Thus, embodiments of VALVE DELIVERY TOOL are disclosed. One skilled in the art will appreciate that the heart valves and associated apparatuses, systems and methods described herein can be practiced with embodiments other than those disclosed. The disclosed embodiments are presented for purposes of illustration and not limitation.

What is claimed is:

1. A prosthetic heart valve delivery device comprising:
   a holder configured to retain a self-expanding prosthetic heart valve, the holder comprising:
      a first loop configured to be circumferentially disposed about at least a portion of an inflow region of the prosthetic heart valve such that constriction or expansion of the first loop controls constriction or expansion of at least a portion of the inflow region of the prosthetic heart valve;
      a second loop configured to be circumferentially disposed about at least a portion of an outflow region of the prosthetic heart valve such that constriction or expansion of the second loop controls constriction or expansion of at least a portion of the outflow region of the prosthetic heart valve; and
      a third loop configured to be circumferentially disposed about at least a portion of a middle region between the inflow region and the outflow region of the prosthetic heart valve such that constriction or expansion of the third loop controls constriction or expansion of at least a portion of the middle region of the prosthetic heart valve.

2. The device of claim 1, wherein each loop is independently constrictable and expandable.

3. The device of claim 1, wherein at least one loop is independently constrictable and expandable relative to at least one other loop.

4. The device of claim 1, wherein at least two loops are dependently constrictable and expandable.

5. The device of claim 1, wherein the first loop is a portion of a first cord extending from the holder, the second loop is a portion of a second cord extending from the holder, and the third loop is a portion of a third cord extending from the holder.

6. The device of claim 1, wherein the prosthetic heart valve has a longitudinal axis and wherein the holder is configured to align with the longitudinal axis of the prosthetic heart valve.

7. The device of claim 1, wherein the prosthetic heart valve has a longitudinal axis and wherein the holder is configured to be offset from the longitudinal axis of the prosthetic heart valve.

8. The device of claim 1, wherein the holder is positioned external to the prosthetic heart valve when the holder retains the heart valve in a constricted configuration.

9. The device of claim 1, wherein at least a portion of the holder is positioned within at least a portion of the prosthetic heart valve when the holder retains the heart valve in a constricted configuration.

10. The device of claim 1, wherein at least one loop is a portion of a chord extending from at least one extension of the holder.

11. The device of claim 1, wherein the holder comprises at least one extension for each loop.

12. The device of claim 1, wherein at least one loop comprises a suture.

13. The device of claim 1, further comprising a shaft coupled to the holder.

14. The device of claim 1, wherein the holder comprises an adapter configured to cooperatively mate with a shaft.

15. The device of claim 1, further comprising a shaft having a lumen coupled to the holder and a chord extending through the lumen such that at least one end of the cord extends beyond the shaft.

16. The device of claim 1, wherein the first loop is a portion of a first cord, wherein the second loop is a portion of a second cord, wherein the third loop is a portion of a third cord, wherein the holder comprises a first extension member having a first opening, a second opening and a conduit between the first and second openings, wherein the holder comprises a second extension member having a first opening, a second opening and a conduit between the first and second openings, wherein a portion of the first cord extends through the conduit of the first extension member, and wherein a portion of the second and third cords extend through the conduit of the second extension member.

17. The device of claim 1, further comprising one or more actuation elements coupled to one or more of the first, second, and third loops such that constriction and expansion of the one or more loops is controllable via the one or more actuation elements.

18. A prosthetic heart valve delivery device comprising:
   a holder configured to retain a self-expanding prosthetic heart valve, the holder comprising:
      a first chord forming a first loop extending from the holder, the first loop configured to be circumferentially disposed about at least a portion of an inflow region of the prosthetic heart valve such that constriction or expansion of the first loop controls constriction or expansion of at least a portion of the inflow region of the prosthetic heart valve;
      a second chord forming a second loop extending from the holder, the second loop configured to be circumferentially disposed about at least a portion of an outflow region of the prosthetic heart valve such that constriction or expansion of the second loop controls constriction or expansion of at least a portion of the outflow region of the prosthetic heart valve; and
      a third chord forming a third loop extending from the holder, the third loop configured to be circumferentially disposed about at least a portion of a middle region of the prosthetic heart valve such that constriction or expansion of the third loop controls constriction or expansion of at least a portion of the middle region of the prosthetic heart valve; and
   a shaft having a proximal end and a distal end, the distal end of the shaft coupled to the holder; and
   a handle coupled to the proximal end of the shaft, the handle comprising one or more actuation elements coupled to at least one end of one or more of the first, second, and third chords, wherein the one or more chords extend from the holder and through the shaft such that constriction and expansion of one or more of the first, second, and third loops is controllable via one or more actuation elements.

19. The device of claim 18, wherein the handle further comprises a first actuation element coupled to the first chord such that constriction and expansion of the first loop is controllable via the first actuation element, a second actuation element coupled to the second chord such that constriction and expansion of the second loop is controllable via the second actuation element, and a third actuation element coupled to the third chord such that constriction and expansion of the third loop is controllable via the third actuation element.

20. The device of claim 18, wherein one or more actuation elements are motorized.

* * * * *